United States Patent
Bonneau et al.

(10) Patent No.: US 8,637,496 B2
(45) Date of Patent: *Jan. 28, 2014

(54) COMPOUNDS HAVING A MONOGALACTOSYLDIACYLGLYCEROL SYNTHASE INHIBITORY ACTIVITY AS HERBICIDE OR ALGAECIDE, HERBICIDE AND ALGAECIDE COMPOSITIONS

(75) Inventors: Anne-Laure Bonneau, Paris (FR); Cyrille Botte, Grenoble (FR); Michael Deligny, Rhode Saint Genese (BE); Nadia Saidani, Nantes (FR); Hélène Hardre, Châteauvillain (FR); Bernard Rousseau, Levallois-Perret (FR); Roman Lopez, Issy les Moulineaux (FR); Eric Marechal, Grenoble (FR)

(73) Assignees: Commissariat a l'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 455 days.

This patent is subject to a terminal disclaimer.

(21) Appl. No.: 12/601,746

(22) PCT Filed: Jun. 2, 2008

(86) PCT No.: PCT/IB2008/002487
§ 371 (c)(1),
(2), (4) Date: Jul. 9, 2010

(87) PCT Pub. No.: WO2008/146174
PCT Pub. Date: Dec. 4, 2008

(65) Prior Publication Data
US 2010/0273653 A1   Oct. 28, 2010

(30) Foreign Application Priority Data
Jun. 1, 2007   (EP) .................................... 07290684

(51) Int. Cl.
| | | |
|---|---|---|
| A01N 55/02 | (2006.01) |
| A61K 31/555 | (2006.01) |
| A01N 43/42 | (2006.01) |
| A61K 31/44 | (2006.01) |
| A01N 25/00 | (2006.01) |
| C07C 229/00 | (2006.01) |
| C07C 69/76 | (2006.01) |
| C07D 205/12 | (2006.01) |
| C07D 237/28 | (2006.01) |
| C07D 409/00 | (2006.01) |
| C07F 5/02 | (2006.01) |

(52) U.S. Cl.
USPC ........ 514/183; 424/405; 504/116.1; 504/189; 504/223; 504/227; 504/235; 504/244; 504/286; 504/292; 504/299; 504/354; 514/210.01; 514/212.01; 514/247; 514/249; 514/252.12; 514/256; 514/258.1; 514/263.1; 514/277; 514/299; 514/307; 514/317; 514/360; 514/374; 514/393; 514/397; 514/438; 514/461; 514/506; 514/762; 540/203; 540/205; 540/484; 546/79; 546/101; 546/184; 546/256; 546/246; 548/100; 548/170; 548/240; 548/315.1; 548/400; 549/49; 549/200; 549/414; 549/429; 549/472; 560/9; 560/19; 560/55; 560/100; 560/102; 562/400; 564/4; 564/74; 585/16; 585/24; 585/25; 585/26; 585/27; 544/224; 544/238; 544/253; 544/264; 544/336

(58) Field of Classification Search
USPC .............. 504/116.1, 189, 223, 227, 235, 244, 504/286, 292, 299, 348, 354; 514/183, 514/210.01, 212.01, 247, 248, 249, 252.12, 514/256, 258.1, 263.1, 277, 299, 300, 307, 514/311, 315, 317, 336, 359, 360, 365, 372, 514/374, 378, 385, 393, 396, 397, 406, 408, 514/415, 422, 427, 438, 461, 506, 762; 540/203, 205, 484; 544/1, 224, 235, 544/238, 242, 253, 264, 336; 546/1, 79, 546/101, 184, 256, 246; 548/100, 146, 152, 548/170, 180, 181, 182, 206, 207, 215, 240, 548/300.1, 302.7, 304.4, 304.7, 311.1, 548/315.1, 364.1, 373.1, 400; 549/29, 49, 549/58, 200, 396, 398, 414, 429, 469, 472;

560/1, 8, 9, 19, 55, 100, 102; 562/400; 564/4, 74; 570/101; 585/16, 24, 25, 26, 585/27

See application file for complete search history.

(56) References Cited

U.S. PATENT DOCUMENTS

| | | | |
|---|---|---|---|
| 3,989,707 A | | 11/1976 | Janssen et al. |
| 2004/0116294 A1 | * | 6/2004 | Feucht et al. ............ 504/139 |
| 2006/0189629 A1 | * | 8/2006 | Bolger et al. ............ 514/254.06 |

FOREIGN PATENT DOCUMENTS

| | | | |
|---|---|---|---|
| JP | 11035409 A | * | 2/1999 |
| WO | WO 01/05770 | | 1/2001 |

OTHER PUBLICATIONS

Vogel,G., Parasites Shed Light on Cellular Evolution, Science (1997), 275(5305): 1422 [online], Mar. 7, 1997 [retrieved Mar. 11, 2012]. Retrieved from the Internet: <URL: http://www.sciencemag.org/content/275/5305/>.*

*Primary Examiner* — Jane C Oswecki

(74) *Attorney, Agent, or Firm* — Morgan, Lewis & Bockius LLP

(57) ABSTRACT

The invention relates to the use of compounds having a monogalactosyldiacylglycerol (MGDG) synthase inhibitory activity as herbicide or algaecide, and to herbicide and algaecide compositions containing at least one of these compounds.

15 Claims, 4 Drawing Sheets

A. Herbicide controls:

Glyphosate

Triclosan

B. Assay of herbicidal effect:

Compound (17)

Compound (13)

Compound (16)

Compound (23)

0   1   10   25   50   100   200

Concentration of molecules in μM

A. Control growth after 3 days:

Control: DMSO

B. Effect on *Chlamydomonas* after 3 days, at 50 µM

Compound (11)

Compound (20)

Compound (13)

Compound (16)

COMPOUNDS HAVING A MONOGALACTOSYLDIACYLGLYCEROL SYNTHASE INHIBITORY ACTIVITY AS HERBICIDE OR ALGAECIDE, HERBICIDE AND ALGAECIDE COMPOSITIONS

The present application is a U.S. National Phase Application of International Application No. PCT/IB2008/002487 (filed Jun. 2, 2008), which claims priority to European Patent Application EP 07290684.5 (filed Jun. 1, 2007), all of which are hereby incorporated by reference in its entirety.

The invention relates to the field of herbicide/algaecide compositions which are highly suitable for use against a harmful plants in crops or useful plants. More particularly, the invention relates to the use of compounds having a monogalactosyldiacylglycerol (MGDG) synthase inhibitory activity as herbicide or algaecide, and to herbicide and algaecide compositions containing at least one of these compounds.

Plastids, and particularly chloroplasts, are specific and vital organelles of eukaryotic plant and algal cells. All plastids trace back to a single evolutionary event of endosymbiosis (Delwiche, C. F. et al., 1997, Origin of Algae and their Plastids, D. Bhattacharia (Ed.), Springer Verlag, Vienna, 53; Douglas, S., Curr. Opin. Genet. Dev., 1998, 8, 655). In this endosymbiotic event, a cyanobacteria was engulfed inside a eukaryotic cell and remained there, evolving into plastids. The two membranes that surround the plastid, namely the envelope, derive from the two limiting membranes of the cyanobacterial ancestor. The vast majority of plastids are involved in light capture and energy conversion in a process known as photosynthesis. Based on photosynthetic pigments, three lineages are currently considered as distinct evolutionarily-related clusters of taxa:

- The green lineage of primary endosymbionts (Viridiplantae), in which chlorophyll a is associated to chlorophyll b, contains the "green algae" (Chlorophyta), such as *Chlamydomonas reinhardtii*, and the so-called "plants" (Streptophyta), such as *Arabidopsis thaliana*;
- The red lineage of primary endosymbionts, in which chlorophyll a is energetically coupled to phycobiline, contains the "red algae" (Rhodophyta) such as *Cyanidioschyzon merolae*;
- The blue lineage of primary endosymbionts, in which chlorophyll a is associated to phycocyanin and allophycocyanin, is a small group of unicellular organisms (Glaucocystophytes), such as *Cyanophora paradoxa*, in which the chloroplast still contains a peptidoglycan cell wall.

Membranes of all plant and algal plastids have a unique lipid composition. Whereas phospholipids are the major polar lipids of cellular membranes, plastids contain up to 80% galactosylglycerolipids, i.e. 1,2-diacyl-3-O-(β-D-galactopyranosyl)-sn-glycerol (called monogalactosyldiacylglycerol or MGDG) and 1,2-diacyl-3-O-(α-D-galactopyranosyl-1→6-β-D-galactopyranosyl)-sn-glycerol (called digalactosyldiacylglycerol or DGDG) (Douce, R. et al., Biol. Chem., 248, 7215-7222; Joyard J. et al., (1993) in Lipid Metabolism in Plants (Moore, T. S., ed.) pp. 231-257, CRC Press, Boca Raton, Fla. MGDG (monogalactosyldiacylglycerol) and DGDG (digalactosyldiacylglycerol) have respectively the following formula:

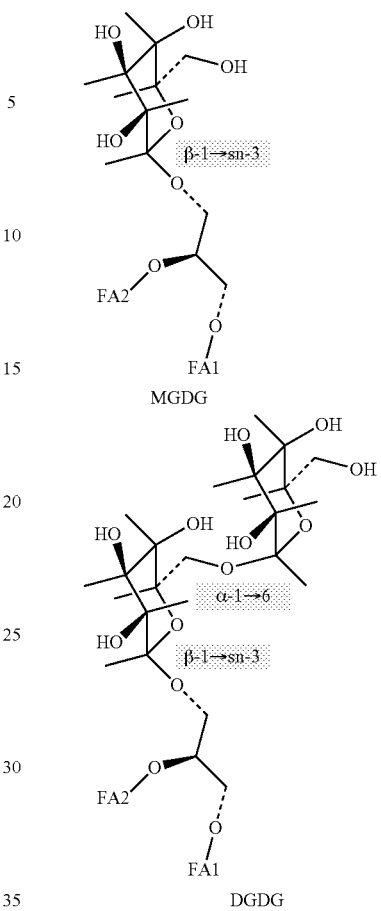

These two lipids are made by assembly of a glycerol backbone, esterified at positions sn-1 and sn-2 by fatty acids (shown as FA1 and FA2) and by one or two galactose residues at position sn-3

Synthesis of MGDG occurs in the membranes that surround plastids, named the plastid envelope. Synthesis of MGDG is a key process for the biogenesis of plastid membranes, particularly for thylakoid expansion (Miège, C. et al., Eur. J. Biochem., 1999, 265, 990-1001; Awai, K. et al., Proc. Natl. Acad. Sci. U. S. A., 2001, 98, 10960-10965; Maréchal, E. et al., Biochem. Soc. Trans., 2000, 28, 732-738). MGDG is also involved in the functional integrity of the photosynthetic machinery. *Arabidopsis* mutants containing half the normal MGDG amount are consistently severely affected, with defects in chloroplast development, impairment of photosynthesis and an overall chlorotic phenotype. MGDG is the substrate for another essential lipid, DGDG, which is exported to plasma membrane and mitochondria under phosphate deprivation, likely to replace missing phosphatidylcholine. In addition to plastid membranes, MGDG synthesis is therefore essential for the biogenesis of most cell membranes. Taken together, the roles played by MGDG are vital and imply that MGD enzymes are targets for herbicide screening, supporting the claims in Patent application EP 1 163 364 and in European Patent EP 1 330 537, that inhibitors of galactolipid synthesis and particularly of MGDG are expected to have herbicidal properties.

MGDG is generated by transfer of a β-galactosyl moiety from a water-soluble UDP-α-D-galactose (UDP-Gal) donor onto sn-3 position of the hydrophobic 1,2-diacyl-sn-glycerol (DAG) acceptor (Ferrari R. et al., Arch. Biochem. Biophys., 1961, 93, 185-192; Neufeld E. F. et al., Biochem. Biophys. Res. Commun, 1965, 14, 503-508). This reaction is catalyzed by a UDP-α-D-galactose:1,2-diacyl-sn-glycerol 3-β-D-galactosyltransferase or MGDG synthase, according to the following reaction:

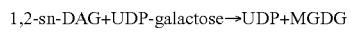

1,2-sn-DAG+UDP-galactose→UDP+MGDG

A collection of MGDG synthase (MGD) genes is now well established in Angiosperms, molecularly characterized in spinach (*Spinacia oleracea*) (Miège, C. et al., Eur. J. Biochem., 1999, 265, 990-1001), thale cress (*Arabidopsis thaliana*) (Awai, K. et al., Proc. Natl. Acad. Sci. U. S. A., 2001, 98, 10960-10965) and rice (*Oriza sativa*) (Qi, Y. H. et al., Planta, 2004, 219, 450-458).

MGD proteins were found to be in the same superfamily of glycosyltransferases as bacterial MURG proteins (Shimojima M. et al., Proc. Natl. Acad. Sci. U. S. A., 1997, 94, 333-337), with whom they are classified in the GT-28 family of the CAZy systematics (CAZy classification is available at http://afmb.cnrs-mrs.fr/CAZY/). MURG catalyzes the last intracellular step in bacterial and cyanobacterial peptidoglycan biosynthesis, i.e. transfer of an N-acetyl-β-D-glucosaminyl from a UDP-α-D-N-acetyl-glucosamine (UDP-GlcNAc) donor onto lipid 1.

MGD orthologs have been identified in the moss *Physcomitrella patens*, the green algae *Chlamydomonas reinhardtii* (crMGD, accessed with the number jgi|Chlre3|113664|e_gwW.2.330.1 in the ChlamyDB website http://www.chlamy.org/chlamydb.html, as of February 2007), and *Prototheca wickerhamii* (pwMGD, with accession number AAV65358 in the National Center for Biotechnology Information (NCBI) web site http://www.ncbi.nlm.nih.gov/), and the red alga *Cyanidioschyzon merolae* (Bone, C. et al., J Biol Chem., 2005, 280, 34691-34701). Based on available genomic sequence information, MGD orthologs could be also found in a Heterokont which cells contain a plastid, the diatom *Thalassiosira pseudonana* (see FIG. 1 which represents the phylogeny of MGD and MURG).

Based on the evolutionary distribution of MGDG synthase genes among plants and algae, and based on the key importance of MGDG for the membrane composition of plastids in all these organisms, inhibitors of MGDG synthesis are expected to be herbicides and algaecides, with a broad spectrum of activity in plants and algae.

In the classification of herbicides according to mode of action (http://www.plantprotection.org/HRAC/Bindex.cfm?doc=moa2002.htm) designed by the Herbicide Resistance Action Committee (HRAC), approximately one third of the herbicides used for agronomic purposes target the plant lipid metabolism. One example is triclosan that targets the fatty acid biosynthesis. Wakabayashi, K. et al., (Pest Manag Sci., 2004, 58, 1149-54) further argue that lipid metabolism appears as a good general target for searching for new herbicides. However, no herbicide has been described to date with a mode of action that would target galactolipid synthesis, and particularly on the synthesis of monogalactosyldiacylglycerol.

Among the different synthetic herbicides already on the market as well as several combinations, one can mention for example the triazine family, like Azatrine, substituted ureas like Diuron and the Glyphosate and several other preparations. For instance Glyphosate, a weak organic acid, is used as its diisopropylamine salt for increasing solubility (Roundup®) and also with some surfactants agents like polyoxyethylene amine.

The intensive use of synthetic herbicides during the past 50 years has brought different problems mainly connected to environmental impact and weed resistance to herbicides. In the context of an increasing demand for high-quality feeding products and environmental concerns, it is important to discover new phytotoxic agents useful in agriculture. These new compounds should be active at low-dose, with little environmental impact, higher selectivity, and alternative modes of action, and decisively contribute to solve the problems associated with chemical weed control.

Concerning the environmental issue, lots of herbicides like triazines or triclosan are chlorinated and their dechlorination is one of the major environmental damage reported so far.

As mentioned earlier, an inevitable problem associated with the use of herbicides is the occurrence of herbicide-resistant weeds. For example, the widespread use of herbicides such as triazines or diphenylether families has caused herbicide resistance in many weeds. Therefore, it is necessary to develop efficient herbicides with novel structures and modes of action to overcome this resistance.

Herbicides have the same mode of entry into the human body as other pesticides, i.e. through skin (dermal), by swallowing (oral) and breathing (inhalation). Herbicides can therefore accumulate in the body and be toxic when a certain concentration is reached. It is well reported that the triazine family may contribute to prostate human cancers with no restriction of its use.

Most efforts are currently focussed on modifications of existing families of herbicides or on new formulation of old compounds like the new glyphosate preparation as proposed in US patent application US 2007/0021304 or to synergistic preparations as reported in US patent application US 2007/0010398. The continued use of the same herbicide or chemically similar herbicides does not avoid the development of herbicide-resistant weeds.

Currently, about two-thirds of the volume of pesticides used in agricultural production are herbicides. The potential for undesirable environmental contamination from herbicides is relatively high, and there is a need for environmentally safe herbicides that are equally or more effective and selective than currently available herbicides. On the other hand, the increasing incidence of herbicide resistance is creating a demand for new herbicides with unexploited mechanism of action. Thus, the need for new herbicides becomes obvious to solve the dilemma of the continued demand for herbicides while older herbicides are removed from the production fields for environmental, toxicological or economical purposes.

A wide range of established products can no longer meet the increasing demands to control resistant weeds, newly emerging weed species, and the increasing demand for environmental sustainability.

The inventors have developed the subject of the invention in order to remedy these problems.

Figure 1:
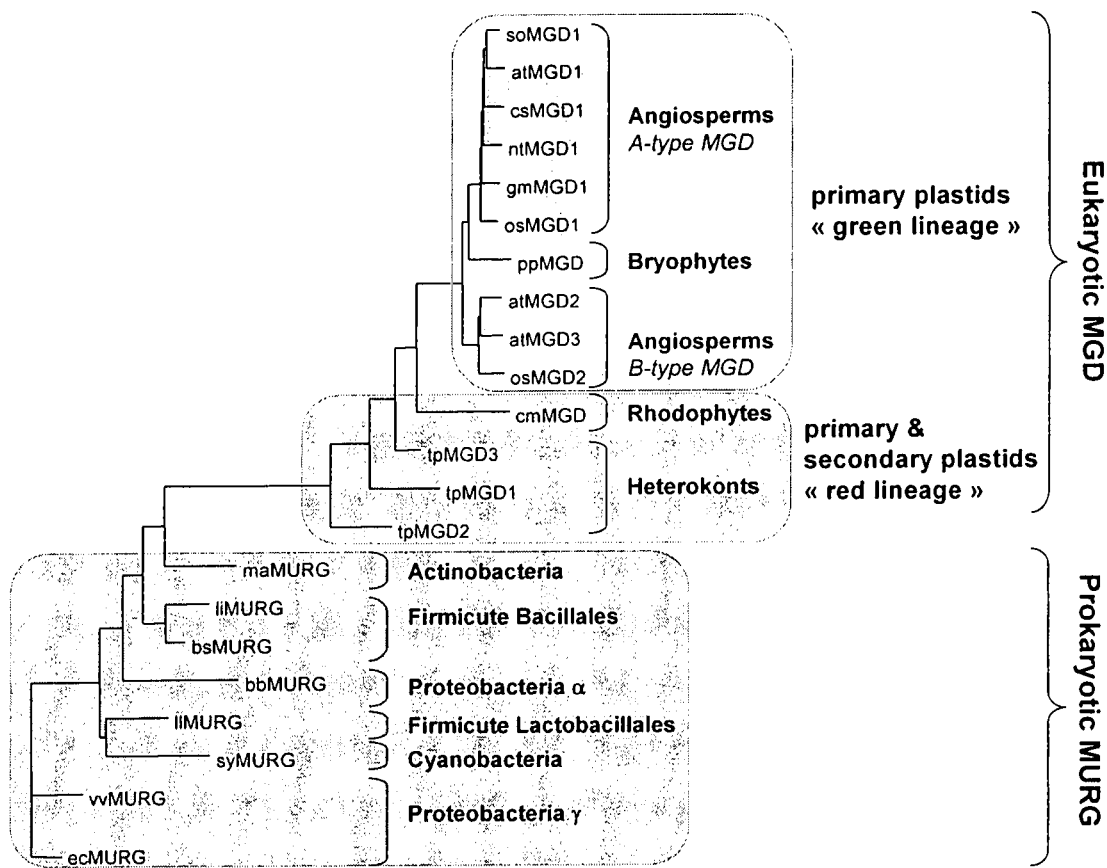
FIG. 1 illustrates the phylogeny of MGD and MURG.

A first subject of the Invention is therefore the use of at least one compound of formula (I) below, as herbicide and/or algaecide:

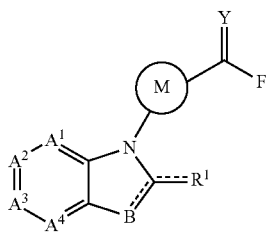
(I)

or an acid addition salt thereof, wherein:

$R^1$ represents a hydrogen atom, an oxygen atom or a sulphur atom;

$A^1$, $A^2$, $A^3$ and $A^4$, identical or different, represent N, —CH— or —$CR^2$— wherein $R^2$ represents a halogen atom or a group selected from alkoxy, alkyl, alkenyl, alkynyl, cycloalkyl, aryl, arylalkyl, heteroaryl and heteroalkyl groups, wherein said groups designated for $R^2$ are optionnaly substituted with one or more groups independently selected from halogen, trifluoromethyl, difluoromethyl, azido, alkyl, alkoxy, cyano and nitro. In addition, and when two adjacent cyclic atoms $A^1$, $A^2$, $A^3$ and $A^4$ represent —$CR^2$— or N, said two adjacent cyclic atoms may also form, together, a fused cyclic structure (cycloalkyl, aryl or heteroaryl);

B represents —N—, —$NR^3$—, —S— or —O—, wherein $R^3$ represents hydrogen, an alkyl group or a group —$COR^4$ wherein $R^4$ represents an aryl or a heteroaryl group, said groups designated for $R^4$ being optionally substituted with one or more groups independently selected from halogen, trifluoromethyl, difluoromethyl, azido, alkyl, alkoxy, cyano and nitro;

the circled M represents a ring selected from the group consisting of the rings of following formula ($M_1$) to ($M_5$):

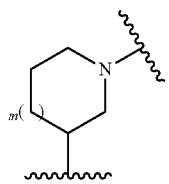
$M_1$

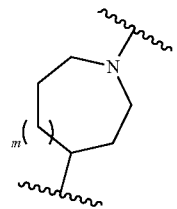
$M_2$

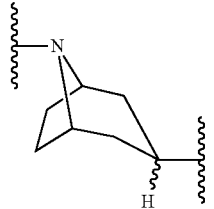
$M_3$

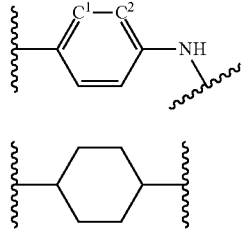
$M_4$

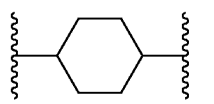
$M_5$ in which m is an integer equal to 0 or 1 and —$C^1$— and —$C^2$—, identical or different, represent a nitrogen atom or —$CR^5$— wherein $R^5$ represents hydrogen, halogen or a group selected from alkoxy, alkyl, alkenyl, alkynyl, cycloalkyl, aryl, arylalkyl heteroaryl and heteroalkyl groups, wherein said groups designated for $R^5$ are optionnaly substituted with one or more groups independently selected from halogen, trifluoromethyl, difluoromethyl, azido, alkyl, alkoxy, cyano and nitro. In addition, and when the two adjacent cyclic atoms —$C^1$ and —$C^2$ represent —$CR^5$, they may also form, together, a fused cyclic structure (cycloalkyl, aryl or heteroaryl);

Y represents an oxygen or a sulphur atom;

F represents one of the following substructures of formula (F-1) to (F-3):

i)

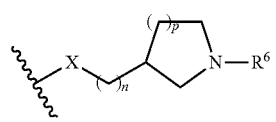
F-1 in which:

n and p can be equal or different and are integers equal to 0, 1, 2 or 3;

X represents an oxygen or a sulphur atom, —NH—, $NR^7$ or —$CHR^7$— in which $R^7$ represents hydrogen, or an alkyl, alkenyl, aryl or heteroaryl group wherein said group designated for $R^7$ is optionnaly substituted with one or more groups independently selected from halogen, trifluoromethyl, difluoromethyl, azido, alkyl, alkoxy, cyano and nitro;

$R^6$ represents an alkyl, alkenyl, alkynyl, cycloalkyl, aryl, arylalkyl, heteroaryl or heteroalkyl group, wherein said group designated for $R^6$ is optionnaly substituted with one or more groups independently selected from halogen, trifluoromethyl, difluoromethyl, azido, alkyl, alkoxy, cyano and nitro:

ii)

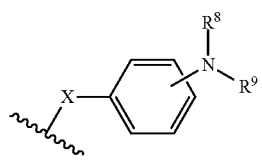

F-2 in which

X has the same definition as the one given for F-1 above;

$R^8$ and $R^9$, identical or different, independently represent hydrogen or an alkyl, alkenyl, alkynyl, cycloalkyl, aryl, arylalkyl, heteroaryl or heteroalkyl group, wherein said groups designated for $R^8$ and $R^9$ may be optionnaly substituted with one or more groups independently selected from halogen, trifluoromethyl, difluoromethyl, azido, alkyl, alkoxy, cyano and nitro;

iii)

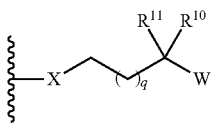

F-3 in which:

X has the same definition as the one given for F-1 above;

q is an integer equal to 0, 1, 2 or 3;

$R^{10}$ and $R^{11}$, identical or different, independently represent hydrogen or an alkyl, alkyloxyalkyl, alkylthioalkyl, alkyloxyaryl, alkylthioaryl, alkenyl, alkynyl, cycloalkyl, aryl, arylalkyl, heteroaryl and heteroalkyl, wherein said groups designated for $R^{10}$ and $R^{11}$ may be optionnaly substituted with one or more groups independently selected from halogen, trifluoromethyl, difluoromethyl, azido, alkyl, alkoxy, aryloxy, thioalkyl, thiaryl, cyano and nitro;

W represents hydrogen or a radical $R^{12}$, $OR^{12}$, $SR^{12}$ or $NR^{12}R^{13}$ wherein $R^{12}$ and $R^{13}$, identical or different, independently represent an alkyl, alkenyl, alkynyl, cycloalkyl, aryl, arylalkyl, heteroaryl or heteroalkyl group, wherein said groups defined for $R^{12}$ and $R^{13}$ may be optionnaly substituted with one or more groups independently selected from halogen, trifluoromethyl, difluoromethyl, azido, alkyl, alkoxy, cyano and nitro; W may also represents a moiety selected in the group consisting of moieties of formula ($W_1$) to ($W_3$) below:

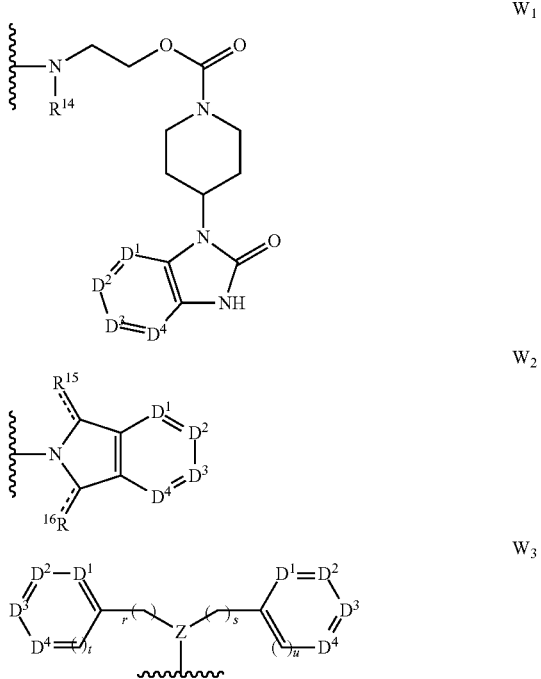

in which:

$R^{14}$ represents hydrogen, an alkyl, alkenyl, alkynyl, cycloalkyl, aryl, arylalkyl, heteroaryl or heteroalkyl group, wherein said groups designated for $R^{14}$ may be optionnaly substituted with one or more groups independently selected from halogen, trifluoromethyl, difluoromethyl, azido, alkyl, alkoxy, cyano and nitro;

$R^{15}$ and $R^{16}$, identical or different, represent a hydrogen or oxygen atom, Z represents a nitrogen atom or a CH group;

r and s, identical or different, are integers equal to 0, 1 or 2;

t and u, identical or different, are integers equal to 0 or 1;

$D^1$, $D^2$, $D^3$ and $D^4$, identical or different, represent a nitrogen atom or C—$R^{17}$, wherein $R^{17}$ represents hydrogen, halogen or an alkoxy, alkyl, alkenyl, alkynyl, cycloalkyl, aryl, arylalkyl, heteroaryl or heteroalkyl group, wherein said groups designated for $R^{17}$ may be optionnaly substituted with one or more groups independently selected from halogen, trifluoromethyl, difluoromethyl, azido, alkyl, alkoxy, cyano and nitro. In addition, and when two adjacent cyclic atoms $D^1$, $D^2$, $D^3$ and $D^4$ represent —$CR^{17}$, said two adjacent cyclic atoms may also form, together, a fused cyclic structure (cycloalkyl, aryl or heteroaryl); it being understood that in compounds of formula (I) in which W represents a moiety of formula ($W_3$), when t or u=0, $D^1$, $D^2$, $D^3$ and $D^4$ can also represent O, S or N—$R^{17}$ groups in which $R^{17}$ has the same definition as in —C—$R^{17}$.

In the sense of the present Invention, alkyl groups (main or auxiliary) mentioned in the present specification preferably correspond to linear or branched ($C_1$-$C_4$)alkyl groups which may for example be chosen among methyl, ethyl, n-propyl, isopropyl, n-butyl, tert-butyl and isobutyl radicals. In the same manner, alkoxy groups (main or auxiliary) mentioned in the present specification are chosen among linear and branched ($C_1$-$C_4$)alkoxy groups such as methyloxy, ethyloxy, n-propyloxy, iso-propyloxy, tert-butyloxy and isobutyloxy radicals Also in the sense of the present Invention, halogen atoms are preferably chosen among chlorine, fluorine, bromine and iodine.

According to the Invention, aryl and heteroaryl groups refer to any functional group or substituent derived from at least one simple aromatic ring; an aromatic ring corresponding to any planar cyclic compound having a delocalized π system in which each atom of the ring comprises a p-orbital, said p-orbitals overlapping themselves. Among heteroaryl groups, one can mention furan, pyridine, pyrrole, thiophene, imidazole, pyrazole, oxazole, isoxazole, thiazole, benzene, pyridine, pyrazine, pyrimidine, pyridazine, benzylcyclobutene, pentalene, benzofurane, isobenzofurane, indole, isoindole, benzothiophene, benzo[c]thiophene, benzimidazole, indazole, benzoxazole, benzisoxazole, benzothiazole, naphthalene, quinoline, isoquinoline, quinoxaline, quinazoline, cinnoline, purine, anthracene and acridine.

According to a preferred embodiment of the present invention, compounds of formula (I) are chosen among compounds in which $A^1=A^2=A^3=A^4=$a carbon atom or $A^1=A^2=A^3=$a carbon atom and $A^4=$a nitrogen atom.

According to another preferred embodiment of the present Invention, compounds of formula (I) are chosen among compounds in which $C^1=C^2=$a carbon atom or $C^1=$a carbon atom and $C^2=$a nitrogen atom or $C^1$ and $C^2$ form together a fused arylic or heteroarylic moiety.

According to still another embodiment of the invention, compounds of formula (I) in which B represents —$NR^3$— with $R^3=$a hydrogen atom are preferred.

A large number of the compounds of formula (I) as above-defined possesses an asymmetric carbon. In this case, they can have the (R) or the (S) configuration. The present Invention encompasses both configurations and mixtures thereof, in particular racemate mixtures.

According to a preferred embodiment of the present invention, said at least one compounds of formula (I) as above-defined, is selected from the group consisting of:

(S)-2-(dibenzylamino)propyl 4-(1,2-dihydro-2-oxobenzo[d] imidazol-3-yl)piperidine-1-carboxylate;
(S)-2-(dibenzylamino)-3-phenylpropyl 4-(1,2-dihydro-2-oxobenzo[d]imidazol-3-yl)piperidine-1-carboxylate;
2-(dibenzylamino)ethyl 4-(1,2-dihydro-2-oxobenzo[d]imidazol-3-yl)piperidine-1-carboxylate;
3-(dibenzylamino)propyl 4-(1,2-dihydro-2-oxobenzo[d]imidazol-3-yl)piperidine-1-carboxylate;
2-(N-benzyl-N-methylamino)ethyl 4-(1,2-dihydro-2-oxobenzo[d]imidazol-3-yl)piperidine-1-carboxylate;
(S)-2-(dibenzylamino)propyl 4-(1,2-dihydro-2-thioxobenzo[d]imidazol-3-yl)piperidine-1-carboxylate;
(S)-2-(dibenzylamino)propyl 4-(1H-benzo[d]imidazol-1-yl)piperidine-1-carboxylate;
O-2-(dibenzylamino)ethyl 4-(1,2-dihydro-2-oxobenzo[d]imidazol-3-yl)piperidine-1-carbothioate;
O-2-(benzyloxy)ethyl 4-(1,2-dihydro-2-oxobenzo[d]imidazol-3-yl)piperidine-1-carbothioate;
(S)-2-(dibenzylamino)propyl 4-(2,3-dihydro-2-oxoimidazo[4,5-b]pyridin-1-yl)piperidine-1-carboxylate;
(S)-2-(dibenzylamino)propyl 4-(1,2-dihydro-2-oxo-1-(benzoyl)benzo[d]imidazol-3-yl)piperidine-1-carboxylate;
(S)-2-(dibenzylamino)propyl 4-(1,2-dihydro-2-oxobenzo[d]imidazol-3-yl)azepane-1-carboxylate;
1-benzhydrylazetidin-3-yl 4-(1,2-dihydro-2-oxobenzo[d]imidazol-3-yl)piperidine-1-carboxylate;
3-(dimethylamino)phenyl 4-(1,2-dihydro-2-oxobenzo[d]imidazol-3-yl)piperidine-1-carboxylate;
2-(1,3-dioxoisoindolin-2-yl)ethyl 4-(1,2-dihydro-2-oxobenzo[d]imidazol-3-yl)piperidine-1-carboxylate;
2-(ethyl(phenyl)amino)ethyl 4-(2-oxo-2,3-dihydro-1H-benzo[d]imidazol-1-yl)piperidine-1-carboxylate;
3,3-diphenylpropyl 4-(1,2-dihydro-2-oxobenzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
(S)-2-(dibenzylamino)propyl 3-(2-oxo-2,3-dihydro-1H-benzo[d]imidazol-1-yl)-8-azabicyclo[3.2.1]octane-8-carboxylate;
1-[1-(4-dibenzylamino-butyryl)-piperidin-4-yl]-1,3-dihydro-benzoimidazol-2-one;
(S)-2-(dibenzylamino)-3-phenylpropyl 4-(1,2-dihydro-1-methyl-2-oxobenzo[d]imidazol-3-yl)piperidine-1-carboxylate;
N—((S)-2-(dibenzylamino)propyl)-4-(1,2-dihydro-2-oxobenzo[d]imidazol-3-yl)piperidine-1-carbothioamide;
N—((S)-2-(dibenzylamino)propyl)-4-(1,2-dihydro-2-oxobenzo[d]imidazol-3-yl)cyclohexanecarboxamide;
2,2-diphenylethyl 4-(1,2-dihydro-2-oxobenzo[d]imidazol-3-yl)piperidine-1-carboxylate;
2-(N-(4-nitrobenzyl)-N-benzylamino)ethyl 4-(1,2-dihydro-2-oxobenzo[d]imidazol-3-yl)piperidine-1-carboxylate;
2-(dibenzylamino)propyl 4-(1,2-dihydro-2-oxobenzo[d]imidazol-3-yl)phenylcarbamate;
(S)-2-(dibenzylamino)-3-methylbutyl 4-(1,2-dihydro-2-oxobenzo[d]imidazol-3-yl)piperidine-1-carboxylate;
(S)-2-(dibenzylamino)-4-methylpentyl 4-(2-oxo-2,3-dihydro-1H-benzo[d]imidazol-1-yl)piperidine-1-carboxylate;
2-(dibenzylamino)-3,3-dimethylbutyl 4-(1,2-dihydro-2-oxobenzo[d]imidazol-3-yl)piperidine-1-carboxylate;
3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
(S)-2-(dibenzylamino)-2-phenylethyl 4-(1,2-dihydro-2-oxobenzo[d]imidazol-3-yl)piperidine-1-carboxylate;
2-(N-benzyl-N-phenylamino)ethyl 4-(1,2-dihydro-2-oxobenzo[d]imidazol-3-yl)piperidine-1-carboxylate;
(S)-2-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-nitrobenzyl)amino)propyl 4-(2-oxo-2,3-dihydro-1H-benzo[d]imidazol-1-yl)piperidine-1-carboxylate
3-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-methoxybenzyl)amino)propyl 4-(2-oxo-2,3-dihydro-1H-benzo[d]imidazol-1-yl)piperidine-1-carboxylate;
2-(benzyl(4-bromobenzyl)amino)ethyl 4-(2-oxo-2,3-dihydro-1H-benzo[d]imidazol-1-yl)piperidine-1-carboxylate;
(S)-2-(benzyl(4-bromobenzyl)amino)propyl 4-(2-oxo-2,3-dihydro-1H-benzo[d]imidazol-1-yl)piperidine-1-carboxylate;
3-(benzyl(4-methoxybenzyl)amino)propyl 4-(2-oxo-2,3-dihydro-1H-benzo[d]imidazol-1-yl)piperidine-1-carboxylate;
(R)-2-(dibenzylamino)-3-phenylpropyl 4-(1,2-dihydro-2-oxobenzo[d]imidazol-3-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;

2-(benzyl(4-methoxybenzyl)amino)ethyl 4-(2-oxo-2,3-dihydro-1H-benzo[d]imidazol-1-yl)piperidine-1-carboxylate;
2-(benzyl(3-methoxybenzyl)amino)ethyl 4-(2-oxo-2,3-dihydro-1H-benzo[d]imidazol-1-yl)piperidine-1-carboxylate;
2-(benzyl(3-phenoxybenzyl)amino)ethyl 4-(2-oxo-2,3-dihydro-1H-benzo[d]imidazol-1-yl)piperidine-1-carboxylate;
2-(benzyl(3-chlorobenzyl)amino)ethyl 4-(2-oxo-2,3-dihydro-1H-benzo[d]imidazol-1-yl)piperidine-1-carboxylate;
(S)-2-(benzyl(4-fluorobenzyl)amino)propyl 4-(2-oxo-2,3-dihydro-1H-benzo[d]imidazol-1-yl)piperidine-1-carboxylate;
(S)-2-(benzyl(3-phenylpropyl)amino)propyl 4-(2-oxo-2,3-dihydro-1H-benzo[d]imidazol-1-yl)piperidine-1-carboxylate;
(S)-2-(benzyl(quinolin-4-ylmethyl)amino)propyl 4-(2-oxo-2,3-dihydro-1H-benzo[d]imidazol-1-yl)piperidine-1-carboxylate;
(S)-2-(benzyl(3-methoxybenzyl)amino)propyl 4-(2-oxo-2,3-dihydro-1H-benzo[d]imidazol-1-yl)piperidine-1-carboxylate;
(S)-2-(benzyl(3-phenoxybenzyl)amino)propyl 4-(2-oxo-2,3-dihydro-1H-benzo[d]imidazol-1-yl)piperidine-1-carboxylate;
(S)-2-(benzyl(3-chlorobenzyl)amino)propyl 4-(2-oxo-2,3-dihydro-1H-benzo[d]imidazol-1-yl)piperidine-1-carboxylate;
2-(benzyl(quinolin-4-ylmethyl)amino)ethyl 4-(2-oxo-2,3-dihydro-1H-benzo[d]imidazol-1-yl)piperidine-1-carboxylate;
3-(benzyl(pyridin-3-ylmethyl)amino)propyl 4-(2-oxo-2,3-dihydro-1H-benzo[d]imidazol-1-yl)piperidine-1-carboxylate;
3-(benzyl(pyridin-2-ylmethyl)amino)propyl 4-(2-oxo-2,3-dihydro-1H-benzo[d]imidazol-1-yl)piperidine-1-carboxylate;
(S)-2-(benzyl(3-(benzyloxy)benzyl)amino)propyl 4-(2-oxo-2,3-dihydro-1H-benzo[d]imidazol-1-yl)piperidine-1-carboxylate;
(S)-2-(benzyl(phenanthren-9-ylmethyl)amino)propyl 4-(2-oxo-2,3-dihydro-1H-benzo[d]imidazol-1-yl)piperidine-1-carboxylate;
(S)-2-(benzyl(naphthalen-1-ylmethyl)amino)propyl 4-(2-oxo-2,3-dihydro-1H-benzo[d]imidazol-1-yl)piperidine-1-carboxylate;
(S)-2-(benzyl(thiophen-2-ylmethyl)amino)propyl 4-(2-oxo-2,3-dihydro-1H-benzo[d]imidazol-1-yl)piperidine-1-carboxylate;
(S)-2-(benzyl(pyridin-2-ylmethyl)amino)propyl 4-(2-oxo-2,3-dihydro-1H-benzo[d]imidazol-1-yl)piperidine-1-carboxylate;
2-(benzyl(tert-butoxycarbonyl)amino)ethyl 4-(2-oxo-2,3-dihydro-1H-benzo[d]imidazol-1-yl)piperidine-1-carboxylate;
3-(benzyl(thiophen-2-ylmethyl)amino)propyl 4-(2-oxo-2,3-dihydro-1H-benzo[d]imidazol-1-yl)piperidine-1-carboxylate;
3-(benzyl(4-fluorobenzyl)amino)propyl 4-(2-oxo-2,3-dihydro-1H-benzo[d]imidazol-1-yl)piperidine-1-carboxylate;
3-(benzyl(3-methoxybenzyl)amino)propyl 4-(2-oxo-2,3-dihydro-1H-benzo[d]imidazol-1-yl)piperidine-1-carboxylate;
3-(benzyl(3-chlorobenzyl)amino)propyl 4-(2-oxo-2,3-dihydro-1H-benzo[d]imidazol-1-yl)piperidine-1-carboxylate;
3-(benzyl(naphthalen-1-ylmethyl)amino)propyl 4-(2-oxo-2,3-dihydro-1H-benzo[d]imidazol-1-yl)piperidine-1-carboxylate;
3-(benzyl(quinolin-4-ylmethyl)amino)propyl 4-(2-oxo-2,3-dihydro-1H-benzo[d]imidazol-1-yl)piperidine-1-carboxylate;
3-(benzyl((1-methyl-1H-indol-2-yl)methyl)amino)propyl 4-(2-oxo-2,3-dihydro-1H-benzo[d]imidazol-1-yl)piperidine-1-carboxylate;
3-(benzyl(3-phenoxybenzyl)amino)propyl 4-(2-oxo-2,3-dihydro-1H-benzo[d]imidazol-1-yl)piperidine-1-carboxylate;
2-(benzyl(4-chlorobenzyl)amino)ethyl 4-(2-oxo-2,3-dihydro-1H-benzo[d]imidazol-1-yl)piperidine-1-carboxylate;
2-(benzyl(2-methoxybenzyl)amino)ethyl 4-(2-oxo-2,3-dihydro-1H-benzo[d]imidazol-1-yl)piperidine-1-carboxylate;
2-(benzyl(2-(benzyloxy)benzyl)amino)ethyl 4-(2-oxo-2,3-dihydro-1H-benzo[d]imidazol-1-yl)piperidine-1-carboxylate;
2-(benzyl(4-(benzyloxy)benzyl)amino)ethyl 4-(2-oxo-2,3-dihydro-1H-benzo[d]imidazol-1-yl)piperidine-1-carboxylate;
2-(benzyl(2,6-difluorobenzyl)amino)ethyl 4-(2-oxo-2,3-dihydro-1H-benzo[d]imidazol-1-yl)piperidine-1-carboxylate;
(S)-2-(benzyl(furan-2-ylmethyl)amino)propyl 4-(2-oxo-2,3-dihydro-1H-benzo[d]imidazol-1-yl)piperidine-1-carboxylate;
3-(benzyl(furan-3-ylmethyl)amino)propyl 4-(2-oxo-2,3-dihydro-1H-benzo[d]imidazol-1-yl)piperidine-1-carboxylate;
2-(benzyl(3-(benzyloxy)benzyl)amino)ethyl 4-(2-oxo-2,3-dihydro-1H-benzo[d]imidazol-1-yl)piperidine-1-carboxylate;
(E)-2-(benzyl(cinnamyl)amino)ethyl 4-(2-oxo-2,3-dihydro-1H-benzo[d]imidazol-1-yl)piperidine-1-carboxylate;
3-(benzyl(4-chlorobenzyl)amino)propyl 4-(2-oxo-2,3-dihydro-1H-benzo[d]imidazol-1-yl)piperidine-1-carboxylate;
3-(benzyl(3-(benzyloxy)benzyl)amino)propyl 4-(2-oxo-2,3-dihydro-1H-benzo[d]imidazol-1-yl)piperidine-1-carboxylate;
(S)-2-(benzyl(tert-butoxycarbonyl)amino)-4-methylpentyl 4-(2-oxo-2,3-dihydro-1H-benzo[d]imidazol-1-yl)piperidine-1-carboxylate;
(S)-2-(benzyl(tert-butoxycarbonyl)amino)-3-phenylpropyl 4-(2-oxo-2,3-dihydro-1H-benzo[d]imidazol-1-yl)piperidine-1-carboxylate;
(S)-2-(benzylamino)-4-methylpentyl 4-(2-oxo-2,3-dihydro-1H-benzo[d]imidazol-1-yl)piperidine-1-carboxylate;
2-(benzylamino)-3-phenylpropyl 4-(2-oxo-2,3-dihydro-1H-benzo[d]imidazol-1-yl)piperidine-1-carboxylate;
2-(benzyl(3-(benzyloxy)propyl)amino)propyl 4-(2-oxo-2,3-dihydro-1H-benzo[d]imidazol-1-yl)piperidine-1-carboxylate;
3-(benzyl(3-phenylpropyl)amino)propyl 4-(2-oxo-2,3-dihydro-1H-benzo[d]imidazol-1-yl)piperidine-1-carboxylate and acid addition salts thereof.

Among these particular compounds of formula (I), the following compounds are particularly preferred for a use as herbicide:
(S)-2-(dibenzylamino)propyl 4-(1H-benzo[d]imidazol-1-yl)piperidine-1-carboxylate;
2-(ethyl(phenyl)amino)ethyl 4-(2-oxo-2,3-dihydro-1H-benzo[d]imidazol-1-yl)piperidine-1-carboxylate;
(S)-2-(dibenzylamino)propyl 4-(2,3-dihydro-2-oxoimidazo[4,5-b]pyridin-1-yl)piperidine-1-carboxylate;
1-benzhydrylazetidin-3-yl 4-(1,2-dihydro-2-oxobenzo[d]imidazol-3-yl)piperidine-1-carboxylate;
(S)-2-(dibenzylamino)-3-phenylpropyl 4-(1,2-dihydro-2-oxobenzo[d]imidazol-3-yl)piperidine-1-carboxylate;

2-(dibenzylamino)ethyl 4-(1,2-dihydro-2-oxobenzo[d]imidazol-3-yl)piperidine-1-carboxylate;
O-2-(dibenzylamino)ethyl 4-(1,2-dihydro-2-oxobenzo[d]imidazol-3-yl)piperidine-1-carbothioate;
2-(N-(4-nitrobenzyl)-N-benzylamino)ethyl 4-(1,2-dihydro-2-oxobenzo[d]imidazol-3-yl)piperidine-1-carboxylate;
1-[1-(4-dibenzylamino-butyryl)-piperidin-4-yl]-1,3-dihydro-benzoimidazol-2-one;
(S)-2-(dibenzylamino)propyl 4-(1,2-dihydro-2-oxobenzo[d]imidazol-3-yl)piperidine-1-carboxylate;
3-(dibenzylamino)propyl 4-(1,2-dihydro-2-oxobenzo[d]imidazol-3-yl)piperidine-1-carboxylate;
2-(1,3-dioxoisoindolin-2-yl)ethyl 4-(1,2-dihydro-2-oxobenzo[d]imidazol-3-yl)piperidine-1-carboxylate;
3,3-diphenylpropyl 4-(1,2-dihydro-2-oxobenzo[d]imidazol-3-yl)piperidine-1-carboxylate;
2-(dibenzylamino)propyl 4-(1,2-dihydro-2-oxobenzo[d]imidazol-3-yl)phenylcarbamate;
(S)-2-(dibenzylamino)propyl 4-(1,2-dihydro-2-oxo-1-(benzoyl)benzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
N—((S)-2-(dibenzylamino)propyl)-4-(1,2-dihydro-2-oxobenzo[d]imidazol-3-yl)piperidine-1-carbothioamide;
2,2-diphenylethyl 4-(1,2-dihydro-2-oxobenzo[d]imidazol-3-yl)piperidine-1-carboxylate;
(S)-2-(dibenzylamino)-3-phenylpropyl 4-(1,2-dihydro-1-methyl-2-oxobenzo[d]imidazol-3-yl)piperidine-1-carboxylate;
(S)-3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
3-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-methoxybenzyl)amino)propyl 4-(2-oxo-2,3-dihydro-1H-benzo[d]imidazol-1-yl)piperidine-1-carboxylate;
2-(benzyl(4-bromobenzyl)amino)ethyl 4-(2-oxo-2,3-dihydro-1H-benzo[d]imidazol-1-yl)piperidine-1-carboxylate;
3-(benzyl(4-methoxybenzyl)amino)propyl 4-(2-oxo-2,3-dihydro-1H-benzo[d]imidazol-1-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;
2-(benzyl(4-methoxybenzyl)amino)ethyl 4-(2-oxo-2,3-dihydro-1H-benzo[d]imidazol-1-yl)piperidine-1-carboxylate;
2-(benzyl(3-methoxybenzyl)amino)ethyl 4-(2-oxo-2,3-dihydro-1H-benzo[d]imidazol-1-yl)piperidine-1-carboxylate;
(S)-2-(benzyl(3-phenylpropyl)amino)propyl 4-(2-oxo-2,3-dihydro-1H-benzo[d]imidazol-1-yl)piperidine-1-carboxylate;
3-(benzyl(pyridin-3-ylmethyl)amino)propyl 4-(2-oxo-2,3-dihydro-1H-benzo[d]imidazol-1-yl)piperidine-1-carboxylate;
3-(benzyl(pyridin-2-ylmethyl)amino)propyl 4-(2-oxo-2,3-dihydro-1H-benzo[d]imidazol-1-yl)piperidine-1-carboxylate;
(S)-2-(benzyl(3-(benzyloxy)benzyl)amino)propyl 4-(2-oxo-2,3-dihydro-1H-benzo[d]imidazol-1-yl)piperidine-1-carboxylate;
(S)-2-(benzyl(pyridin-2-ylmethyl)amino)propyl 4-(2-oxo-2,3-dihydro-1H-benzo[d]imidazol-1-yl)piperidine-1-carboxylate;
2-(benzyl(tert-butoxycarbonyl)amino)ethyl 4-(2-oxo-2,3-dihydro-1H-benzo[d]imidazol-1-yl)piperidine-1-carboxylate;
3-(benzyl(thiophen-2-ylmethyl)amino)propyl 4-(2-oxo-2,3-dihydro-1H-benzo[d]imidazol-1-yl)piperidine-1-carboxylate;
3-(benzyl(4-fluorobenzyl)amino)propyl 4-(2-oxo-2,3-dihydro-1H-benzo[d]imidazol-1-yl)piperidine-1-carboxylate;
3-(benzyl(3-phenylpropyl)amino)propyl 4-(2-oxo-2,3-dihydro-1H-benzo[d]imidazol-1-yl)piperidine-1-carboxylate;
3-(benzyl(3-methoxybenzyl)amino)propyl 4-(2-oxo-2,3-dihydro-1H-benzo[d]imidazol-1-yl)piperidine-1-carboxylate;
3-(benzyl(3-chlorobenzyl)amino)propyl 4-(2-oxo-2,3-dihydro-1H-benzo[d]imidazol-1-yl)piperidine-1-carboxylate;
3-(benzyl(naphthalen-1-ylmethyl)amino)propyl 4-(2-oxo-2,3-dihydro-1H-benzo[d]imidazol-1-yl)piperidine-1-carboxylate;
2-(benzyl(2-methoxybenzyl)amino)ethyl 4-(2-oxo-2,3-dihydro-1H-benzo[d]imidazol-1-yl)piperidine-1-carboxylate;
2-(benzyl(2,6-difluorobenzyl)amino)ethyl 4-(2-oxo-2,3-dihydro-1H-benzo[d]imidazol-1-yl)piperidine-1-carboxylate;
3-(benzyl(furan-3-ylmethyl)amino)propyl 4-(2-oxo-2,3-dihydro-1H-benzo[d]imidazol-1-yl)piperidine-1-carboxylate;
(E)-2-(benzyl(cinnamyl)amino)ethyl 4-(2-oxo-2,3-dihydro-1H-benzo[d]imidazol-1-yl)piperidine-1-carboxylate;
3-(benzyl(4-chlorobenzyl)amino)propyl 4-(2-oxo-2,3-dihydro-1H-benzo [d]imidazol-1-yl)piperidine-1-carboxylate;
2-(benzyl(3-(benzyloxy)propyl)amino)propyl 4-(2-oxo-2,3-dihydro-1H-benzo[d]imidazol-1-yl)piperidine-1-carboxylate and acid addition salts thereof.

Among these particular compounds of formula (I), the following compounds are particularly preferred for a use as algaecide:
2-(dibenzylamino)ethyl 4-(1,2-dihydro-2-oxobenzo[d]imidazol-3-yl)piperidine-1-carboxylate;
O-2-(benzyloxy)ethyl 4-(1,2-dihydro-2-oxobenzo[d]imidazol-3-yl)piperidine-1-carbothioate;
1-benzhydrylazetidin-3-yl 4-(1,2-dihydro-2-oxobenzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
(S)-2-(dibenzylamino)-3-phenylpropyl 4-(1,2-dihydro-1-methyl-2-oxobenzo[d]imidazol-3-yl)piperidine-1-carboxylate;
3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
(S)-2-(benzyl(4-bromobenzyl)amino)propyl 4-(2-oxo-2,3-dihydro-1H-benzo[d]imidazol-1-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;

2-(benzyl(4-methoxybenzyl)amino)ethyl 4-(2-oxo-2,3-dihydro-1H-benzo[d]imidazol-1-yl)piperidine-1-carboxylate;

2-(benzyl(3-methoxybenzyl)amino)ethyl 4-(2-oxo-2,3-dihydro-1H-benzo[d]imidazol-1-yl)piperidine-1-carboxylate;

3-(benzyl(pyridin-3-ylmethyl)amino)propyl 4-(2-oxo-2,3-dihydro-1H-benzo[d]imidazol-1-yl)piperidine-1-carboxylate;

3-(benzyl(pyridin-2-ylmethyl)amino)propyl 4-(2-oxo-2,3-dihydro-1H-benzo[d]imidazol-1-yl)piperidine-1-carboxylate;

2-(benzyl(tert-butoxycarbonyl)amino)ethyl 4-(2-oxo-2,3-dihydro-1H-benzo[d]imidazol-1-yl)piperidine-1-carboxylate and acid addition salts thereof.

The acid addition salts of the compounds according to the present invention can be for example chosen among hydrochloride, hydrobromide, sulphate or bisulphate, phosphate or hydrogenophosphate, acetate, benzoate, succinate, fumarate, maleate, lactate, citrate, tartrate, gluconate, methanesulphonate, benzene-sulphonate and paratoluene-sulphonate.

Compounds Preparation

Two different protocols can be employed for the preparation of all compounds of the above defined formula (I):

a classical solution phase synthesis and a solid phase synthesis on solid support.

Firstly, in the case of classical solution phase synthesis, all compounds of formula (I) according to the present Invention can be prepared using state of the art methodologies which are briefly described here.

Final compounds belonging to general structure (I) can be decomposed in 3 parts: N (north) part, M (middle) part and Het (heterocyclic or south) part as shown below on the formula (I):

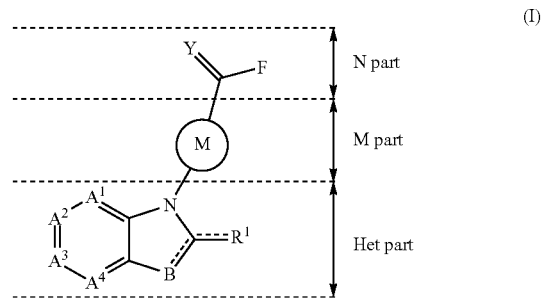

The main difference between the different synthetic pathways which can be used is the order of introduction and connection of these different moieties which is related to the use or absence of use of a precursor for the Het part.

The scheme 1 below shows the synthetic strategies for compounds of formula (I) with non heteroaryl M ring.

SCHEME 1

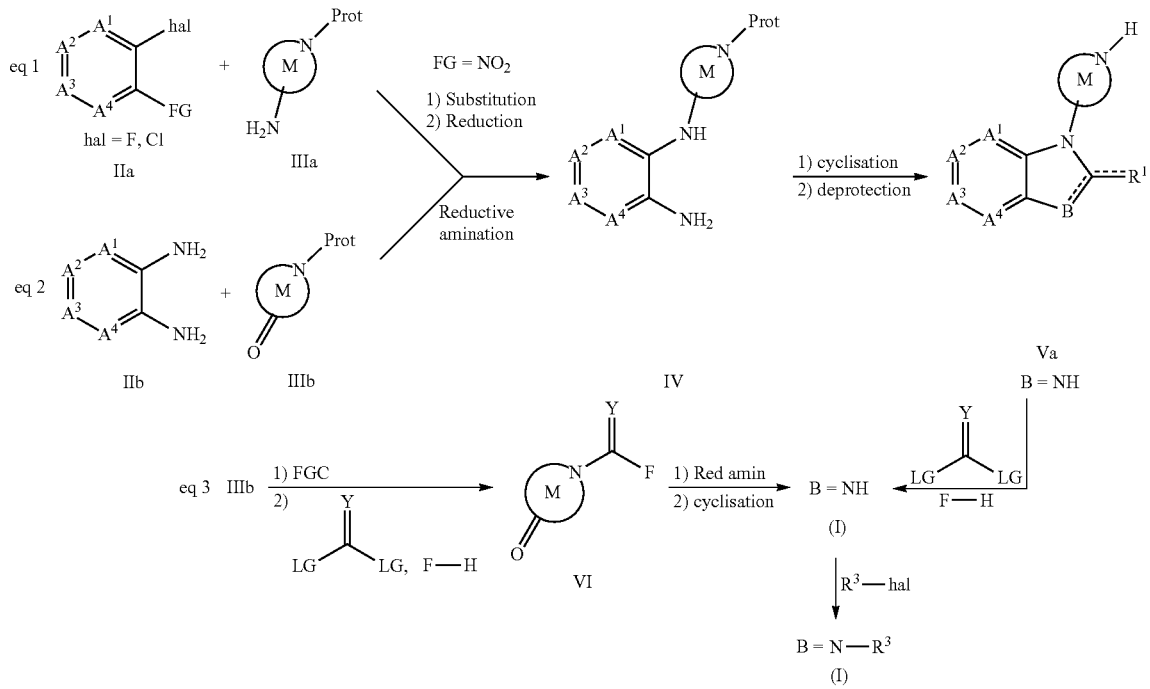

in which $A^1$, $A^2$, $A^3$, $A^4$, B, $R^1$, Y, M and F have the same meanings as in formula (I) as defined above, Prot represents a classical protective group, LG means for leaving group such as halogen, imidazol, methylsufonate, alkylsulfide, which can be in situ generated, hal means for a halogen atom and FGC means "Functional Group Conversion" and includes the deprotection steps. Protecting groups are well known from the one skilled in the art and are described for example in "Protective groups in organic synthesis", T. W. GREENE et al., $2^{nd}$ edition, Wiley Interscience, 1991. As examples of these protecting groups, one can mention benzyl; isopropenyl; benzyloxycarbonyle (Z); trifluoroacetyle (TFA); tert-butyloxycarbonyle (Boc); trimethylsilylethoxycarbonyle (Teoc) and fluorenylmethyloxycarbonyle (Fmoc) groups.

According to scheme 1, and starting from heterocyclic precursor (II-a) or (II-b), attachment of the M ring can be performed either by reductive amination (eq 2), using a compound (III-b) with sodium triacetoxyborohydride or by aromatic nucleophilic substitution, using a compound (III-a) (eq 1), for example according to the method described in the article by Li, Q. et al., Bioorg. Med. Chem. Lett., 2005, 15, 2918-2922.

Convenient functional group conversion (FGC), leading to intermediates of type (IV), allows the preparation of compounds of type (V-a) after cyclisation.

Those ring closures can be performed using different reagents such as carbonyldiimidazol (CDI) or glyoxal, glyoxylates, pyruvates, alkyl halides, acyl halides or carboxylic acids in order to obtain the corresponding fused heterocyclic structures.

Part N can be then connected via F attachment to compounds of formula (V-a) allowing the preparation of compounds with formula (I) ($R^3$=H). Further functionalization was performed using different electrophiles bearing the $R^3$ group such as alkyl halides or acyl chlorides. In an alternative way (scheme 1, eq 3) part N is built first via F attachment to ketones of formula (III-b), affording ketones of formula (VI), which can then be transformed into compounds of formula (I) according to the present Invention by reductive amination, and subsequently subjected to cyclisation by convenient methods.

Some F compounds were commercially available and were therefore directly used for connecting part N to the M ring part using the same already mentioned protocol.

In the case, where compounds of formula (I) comprise an arylic or heteroarylic M ring, an organometallic coupling or a nucleophilic substitution can be performed according to the following scheme 2:

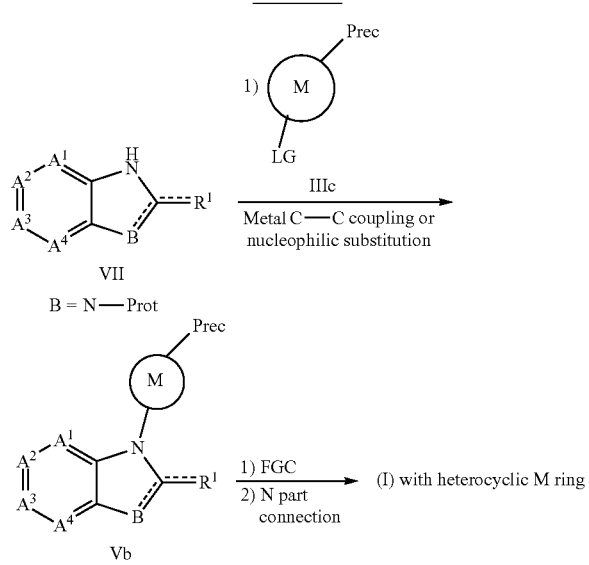

in which $A^1$, $A^2$, $A^3$, $A^4$, B, $R^1$, M and F have the same meanings as in formula (I) as defined above, Prot represents a classical protective group, Prec is a group precursor which structure depends on the final connection between M and F parts and therefore can be a nitro or ester group. LG means a leaving group as previously defined.

After Het and M parts connection, the N part can be attached according to the already described procedure (vide supra).

In some particular cases where the Het part and the M part are commercially available (benzimidazolones for example) the connection between the three blocks M, Het and N can be performed in a convenient order depending on the nature of these materials.

Starting Materials and Protocols

F comprising primary amines are either commercially available or prepared from the corresponding alcohol using phtalimide followed by hydrazine deprotection as described for example in the article by Berger, Y et al., J. Med. Chem., 2005, 48, 483-498. When the F part contains an alcohol, non commercial materials can be prepared according to reported procedures, amino alcohols were functionalized by amine alkylation using a convenient halide (Le Bihan, G. et al., J. Med. Chem., 1999, 42, 1587-1603; Schwerdtfeger, J. et al., Synthesis, 1999, 1573-1592, Enders, D. et al., Synthesis, 1996, 53-58) or functional group conversion (FGC) starting from commercially available aminoacids. Acids and derivatives were obtained afters esters hydrolysis using hydrogen chloride in methanol.

Amides can be obtained by acyl chloride addition to the M part moiety using triethylamine in dichloromethane (DCM).

When X contains an heteroatom (O, N) and Y=O, carbamates or ureas can be prepared using treatment of alcohol or amines with carbonyldiimidazol (CDI) according to the methods as described for example by Choi, S.-W. et al., J. Bioorg. Med. Chem., 2002, 10, 4091-4102, followed by treatment with the corresponding amines. For thiocarbamates preparation (X=O, Y=S), sodium salt of the corresponding alcohols are first treated with carbondisulfide in hot methanol followed by methylation with methyl iodide according to the method for example described in the article by Calter, M. A. et al., J. Org. Chem., 2001, 66, 7500-7504. The corresponding dithiocarbonates obtained are then added to the corresponding amines. For thioureas preparation (X=NH, Y=S), amines can be added to carbondisulfide in acetonitrile generating the corresponding thiols which are activated by 1-(3-dimethylaminopropyl)-3-ethylcarbodiimide hydrochloride (EDCI) before addition of the M part in order to afford thioureas as described for example in the article by Bhandari, K. et al., Bioorg. Med. Chem., 2004, 12, 4189-4196.

In some cases, M part with alcohol function can be obtained from the corresponding ketones using sodium borohydride reduction as described for example in the article by Wang, Y. et al., Bioorg. Med. Chem. Lett., 2005, 11, 891-894. In the case of some M ring precursors with ester function, connection with F part was performed using Weinreb protocol (Nahm, S. et al., Tetrahedron Lett., 1981, 22, 2815-2818) in presence of $AlMe_3$. The 4-oxoazepane ring can be prepared according to reported procedure (Finney, Z. G. et al., J. Med. Chem., 1980, 23, 895-899). N-Carbamoyl-protected tropinone is deprotected with iodotrimethylsilane in hot 1,2-dichloroethane.

Concerning heteroarylic M ring compounds, protective groups as isopropenyl were employed in the particular case where B=$NR^3$ according to literature procedure (Vernin, G. et al., J. Heterocyclic Chem., 1981, 18, 85-89). Nucleophilic aromatic substitution with fluoro-aryl nitro compounds in hot dimethylsulfoxide (DMSO) is performed in presence of potassium carbonate. After decaborane-Pd/C reduction of the nitro group according to known methods, the corresponding carbamates were obtained upon treatment with a convenient alcohol in the presence of triphosgen and catalytic amount of dimethylaminopyridine (DMAP). Removal of the isopropenyl group can be performed using hot acidic medium.

The Introduction of $R^3$ group starting from compounds of formula (I) was performed via the formation of sodium salts of compounds (I) in which B=—NH and after treatment with different electrophiles such as acyl chlorides, alkyl halides according to the method for example described in the article by Jong, L. et al., Bioorg. Med. Chem. Lett., 2004, 14, 181-185.

In the case of benzimidazolones, sodium salts generated with NaH are used in DMF for the last stage alkylation or acylation reactions.

Secondly, it is also possible to synthesize compounds of formula (I) according to the present invention, using solid support parallel library synthesis using a traceless linker strategy with silyl or triazene groups (vide infra).

As an example, solid support parallel synthesis can be performed using the triazene linker strategy developed by Bräse S. et al., Angew. Chem. Int. Ed., 1998, 37, 3413-3415 and Bräse, S., Acc. Chem. Res., 2004, 37, 805-8016. This methodology allows the production of diazonium salts upon cleavage. The known properties of theses salts allow the possibility of a traceless synthesis via reduction or functionalisation. This methodology can be used for the complete construction of the final compounds of formula (I) according to the reactions represented on scheme 4 below:

SCHEME 4

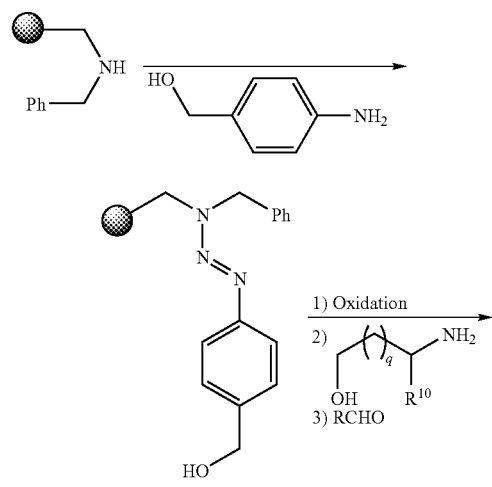

-continued

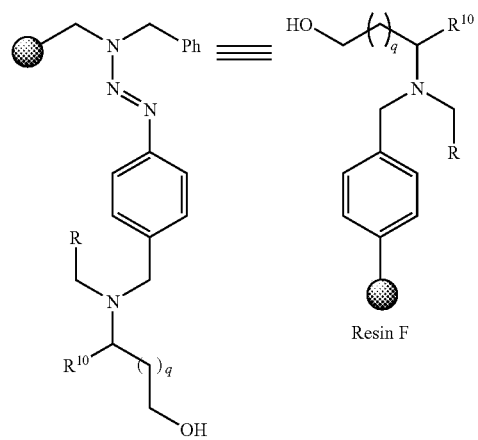

Resin F in which q and $R^{10}$ have the same definition as the one detailed for subformula (F-3) and R group means for particular combinations of W.

The triazene linker can be synthesized using the reported procedure using the corresponding arylamine such as 4-hydroxymethyl aniline. Oxidation to aldehyde takes place using ioded-based reagents such an IBX or Dess Martin periodinane. The two first elements of diversity can be introduced via two successive reductive aminations using the selected first aminoalcohols as described for example in the article by Schunk S. et al., J. Org. Chem., 2002, 67, 8034-8042 and then aldehydes.

Starting from those supported aminoalcohols on resin F, two synthetic pathways can be used depending of linker stability toward further reaction employed. These two synthetic pathways are represented on schemes 5 below:

SCHEME 5

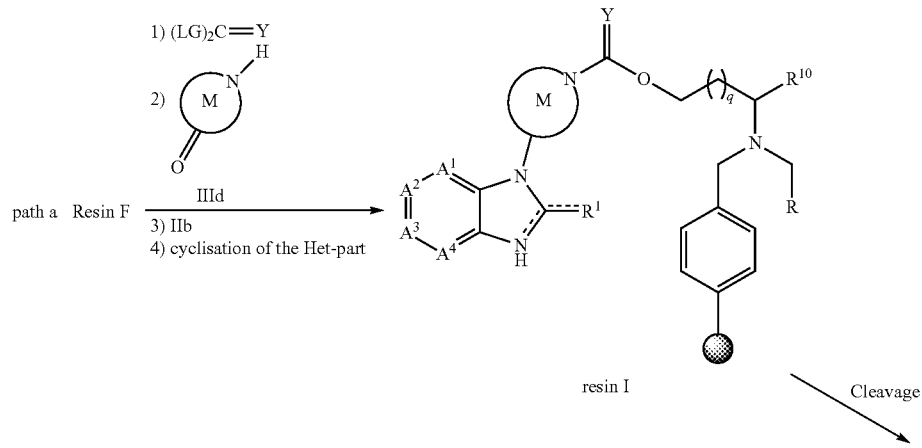

-continued

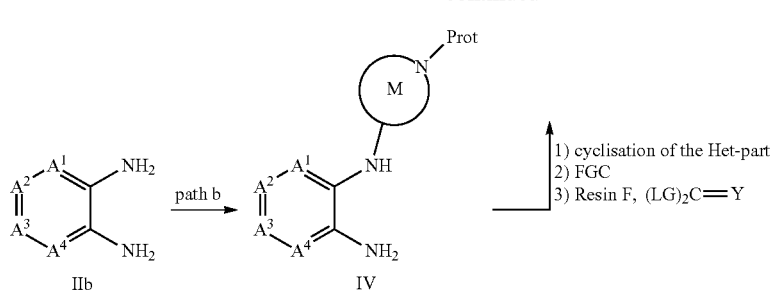

Path a:

Compounds are obtained in a linear <<all supported>> way: Resin F was first connected using the link procedure with ring precursors (III-d). Reductive amination with ketones (II-b) followed by Het ring functionalisation/building using adapted versions of already discussed methodologies, afforded supported final compounds (Resin I).

Path b:

Using a <<catch & release>> methodology allowing a convergent synthesis. Molecules of formula (IV) were first prepared without any purification in solution phase as described before. After ring functionalisation/building and FGC, connection of Resin F afforded Resin I.

Cleavages:

They were performed on Resin I upon treatments using an acid reagent such as TFA or $HSiCl_3$ with an adapted procedure of the literature and afforded compounds of formula (I) according to the Invention.

After the synthesis, compounds of formula (I) according to the present invention can be recovered and purified according to methods also classically used in the art.

As demonstrated in the examples below, compounds or formula (I) as defined above have an herbicide and/or algaecide activity.

Therefore, another subject of the present invention is a herbicide and/or algaecide composition comprising at least one compound of formula (I) as previously described.

According to a particular embodiment of the present invention, the composition is a herbicide composition and the at least one compound of formula (I) is selected from the group consisting of:

(S)-2-(dibenzylamino)propyl 4-(1H-benzo[d]imidazol-1-yl)piperidine-1-carboxylate;
2-(ethyl(phenyl)amino)ethyl 4-(2-oxo-2,3-dihydro-1H-benzo[d]imidazol-1-yl)piperidine-1-carboxylate;
(S)-2-(dibenzylamino)propyl 4-(2,3-dihydro-2-oxoimidazo[4,5-b]pyridin-1-yl)piperidine-1-carboxylate;
1-benzhydrylazetidin-3-yl 4-(1,2-dihydro-2-oxobenzo[d]imidazol-3-yl)piperidine-1-carboxylate;
(S)-2-(dibenzylamino)-3-phenylpropyl 4-(1,2-dihydro-2-oxobenzo[d]imidazol-3-yl)piperidine-1-carboxylate;
2-(dibenzylamino)ethyl 4-(1,2-dihydro-2-oxobenzo[d]imidazol-3-yl)piperidine-1-carboxylate;
O-2-(dibenzylamino)ethyl 4-(1,2-dihydro-2-oxobenzo[d]imidazol-3-yl)piperidine-1-carbothioate;
2-(N-(4-nitrobenzyl)-N-benzylamino)ethyl 4-(1,2-dihydro-2-oxobenzo[d]imidazol-3-yl)piperidine-1-carboxylate;
1-[1-(4-dibenzylamino-butyryl)-piperidin-4-yl]-1,3-dihydro-benzoimidazol-2-one;
(S)-2-(dibenzylamino)propyl 4-(1,2-dihydro-2-oxobenzo[d]imidazol-3-yl)piperidine-1-carboxylate;
3-(dibenzylamino)propyl 4-(1,2-dihydro-2-oxobenzo[d]imidazol-3-yl)piperidine-1-carboxylate;
2-(1,3-dioxoisoindolin-2-yl)ethyl 4-(1,2-dihydro-2-oxobenzo[d]imidazol-3-yl)piperidine-1-carboxylate;
3,3-diphenylpropyl 4-(1,2-dihydro-2-oxobenzo[d]imidazol-3-yl)piperidine-1-carboxylate;
2-(dibenzylamino)propyl 4-(1,2-dihydro-2-oxobenzo[d]imidazol-3-yl)phenylcarbamate;
(S)-2-(dibenzylamino)propyl 4-(1,2-dihydro-2-oxo-1-(benzoyl)benzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
N—((S)-2-(dibenzylamino)propyl)-4-(1,2-dihydro-2-oxobenzo[d]imidazol-3-yl)piperidine-1-carbothioamide;
2,2-diphenylethyl 4-(1,2-dihydro-2-oxobenzo[d]imidazol-3-yl)piperidine-1-carboxylate;
(S)-2-(dibenzylamino)-3-phenylpropyl 4-(1,2-dihydro-1-methyl-2-oxobenzo[d]imidazol-3-yl)piperidine-1-carboxylate;
(S)-3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
3-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-methoxybenzyl)amino)propyl 4-(2-oxo-2,3-dihydro-1H-benzo[d]imidazol-1-yl)piperidine-1-carboxylate;
2-(benzyl(4-bromobenzyl)amino)ethyl 4-(2-oxo-2,3-dihydro-1H-benzo[d]imidazol-1-yl)piperidine-1-carboxylate;
3-(benzyl(4-methoxybenzyl)amino)propyl 4-(2-oxo-2,3-dihydro-1H-benzo[d]imidazol-1-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;
2-(benzyl(4-methoxybenzyl)amino)ethyl 4-(2-oxo-2,3-dihydro-1H-benzo[d]imidazol-1-yl)piperidine-1-carboxylate;
2-(benzyl(3-methoxybenzyl)amino)ethyl 4-(2-oxo-2,3-dihydro-1H-benzo[d]imidazol-1-yl)piperidine-1-carboxylate;
(S)-2-(benzyl(3-phenylpropyl)amino)propyl 4-(2-oxo-2,3-dihydro-1H-benzo[d]imidazol-1-yl)piperidine-1-carboxylate;
3-(benzyl(pyridin-3-ylmethyl)amino)propyl 4-(2-oxo-2,3-dihydro-1H-benzo[d]imidazol-1-yl)piperidine-1-carboxylate;

3-(benzyl(pyridin-2-ylmethyl)amino)propyl 4-(2-oxo-2,3-dihydro-1H-benzo[d]imidazol-1-yl)piperidine-1-carboxylate;
(S)-2-(benzyl(3-(benzyloxy)benzyl)amino)propyl 4-(2-oxo-2,3-dihydro-1H-benzo[d]imidazol-1-yl)piperidine-1-carboxylate;
(S)-2-(benzyl(pyridin-2-ylmethyl)amino)propyl 4-(2-oxo-2,3-dihydro-1H-benzo[d]imidazol-1-yl)piperidine-1-carboxylate;
2-(benzyl(tert-butoxycarbonyl)amino)ethyl 4-(2-oxo-2,3-dihydro-1H-benzo[d]imidazol-1-yl)piperidine-1-carboxylate;
3-(benzyl(thiophen-2-ylmethyl)amino)propyl 4-(2-oxo-2,3-dihydro-1H-benzo[d]imidazol-1-yl)piperidine-1-carboxylate;
3-(benzyl(4-fluorobenzyl)amino)propyl 4-(2-oxo-2,3-dihydro-1H-benzo[d]imidazol-1-yl)piperidine-1-carboxylate;
3-(benzyl(3-phenylpropyl)amino)propyl 4-(2-oxo-2,3-dihydro-1H-benzo[d]imidazol-1-yl)piperidine-1-carboxylate;
3-(benzyl(3-methoxybenzyl)amino)propyl 4-(2-oxo-2,3-dihydro-1H-benzo[d]imidazol-1-yl)piperidine-1-carboxylate;
3-(benzyl(3-chlorobenzyl)amino)propyl 4-(2-oxo-2,3-dihydro-1H-benzo[d]imidazol-1-yl)piperidine-1-carboxylate;
3-(benzyl(naphthalen-1-ylmethyl)amino)propyl 4-(2-oxo-2,3-dihydro-1H-benzo[d]imidazol-1-yl)piperidine-1-carboxylate;
2-(benzyl(2-methoxybenzyl)amino)ethyl 4-(2-oxo-2,3-dihydro-1H-benzo[d]imidazol-1-yl)piperidine-1-carboxylate;
2-(benzyl(2,6-difluorobenzyl)amino)ethyl 4-(2-oxo-2,3-dihydro-1H-benzo[d]imidazol-1-yl)piperidine-1-carboxylate;
3-(benzyl(furan-3-ylmethyl)amino)propyl 4-(2-oxo-2,3-dihydro-1H-benzo[d]imidazol-1-yl)piperidine-1-carboxylate;
(E)-2-(benzyl(cinnamyl)amino)ethyl 4-(2-oxo-2,3-dihydro-1H-benzo[d]imidazol-1-yl)piperidine-1-carboxylate;
3-(benzyl(4-chlorobenzyl)amino)propyl 4-(2-oxo-2,3-dihydro-1H-benzo[d]imidazol-1-yl)piperidine-1-carboxylate;
2-(benzyl(3-(benzyloxy)propyl)amino)propyl 4-(2-oxo-2,3-dihydro-1H-benzo[d]imidazol-1-yl)piperidine-1-carboxylate and acid addition salts thereof.

According to another particular embodiment of the present invention, the composition is an algaecide composition and the at least one compound of formula (I) is selected from the group consisting of:
2-(dibenzylamino)ethyl 4-(1,2-dihydro-2-oxobenzo[d]imidazol-3-yl)piperidine-1-carboxylate;
O-2-(benzyloxy)ethyl 4-(1,2-dihydro-2-oxobenzo[d]imidazol-3-yl)piperidine-1-carbothioate;
1-benzhydrylazetidin-3-yl 4-(1,2-dihydro-2-oxobenzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
(S)-2-(dibenzylamino)-3-phenylpropyl 4-(1,2-dihydro-1-methyl-2-oxobenzo[d]imidazol-3-yl)piperidine-1-carboxylate;
3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
(S)-2-(benzyl(4-bromobenzyl)amino)propyl 4-(2-oxo-2,3-dihydro-1H-benzo[d]imidazol-1-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;
2-(benzyl(4-methoxybenzyl)amino)ethyl 4-(2-oxo-2,3-dihydro-1H-benzo[d]imidazol-1-yl)piperidine-1-carboxylate;
2-(benzyl(3-methoxybenzyl)amino)ethyl 4-(2-oxo-2,3-dihydro-1H-benzo[d]imidazol-1-yl)piperidine-1-carboxylate;
3-(benzyl(pyridin-3-ylmethyl)amino)propyl 4-(2-oxo-2,3-dihydro-1H-benzo[d]imidazol-1-yl)piperidine-1-carboxylate;
3-(benzyl(pyridin-2-ylmethyl)amino)propyl 4-(2-oxo-2,3-dihydro-1H-benzo[d]imidazol-1-yl)piperidine-1-carboxylate;
2-(benzyl(tert-butoxycarbonyl)amino)ethyl 4-(2-oxo-2,3-dihydro-1H-benzo[d]imidazol-1-yl)piperidine-1-carboxylate and acid addition salts thereof.

Figure 2:
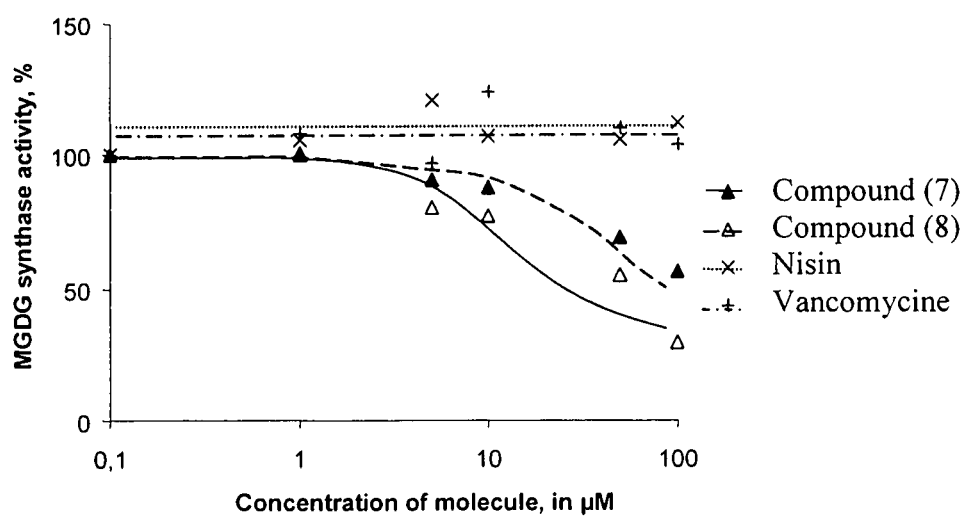
FIG. 2 shows the effect of each of Compounds (7) and (8) on the activity of spinach recombinant MGDG synthase (soMGD) compared to the known herbicides nisin and vancomycin as negative controls.
Figure 3:
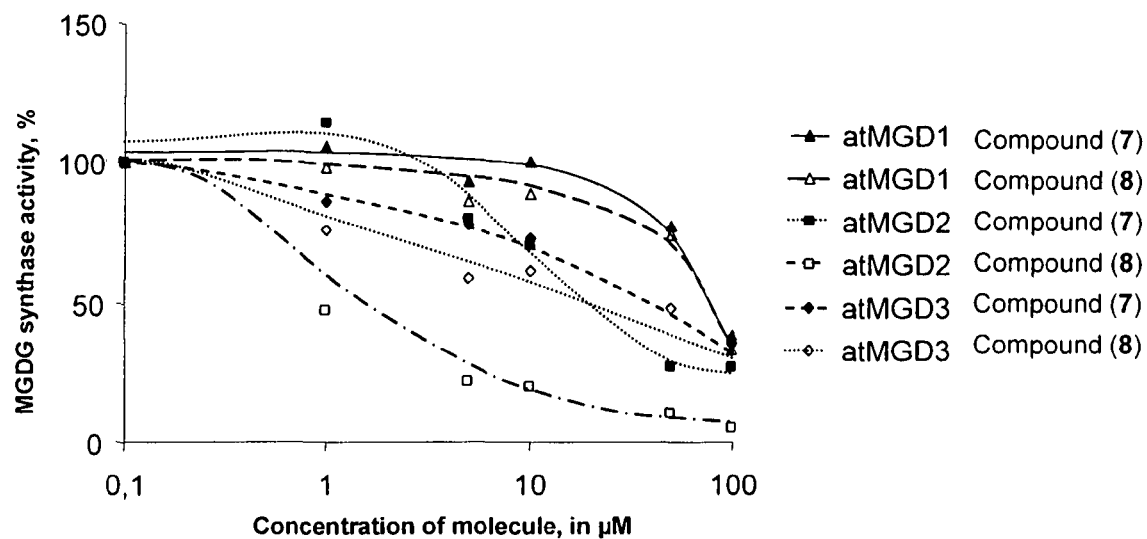
FIG. 3 shows the effect of each of Compounds (7) and (8) on the activity of *Arabidopsis* recombinant MGDG synthase atMGD1, atMGD2 and atMGD3.
Figure 4:
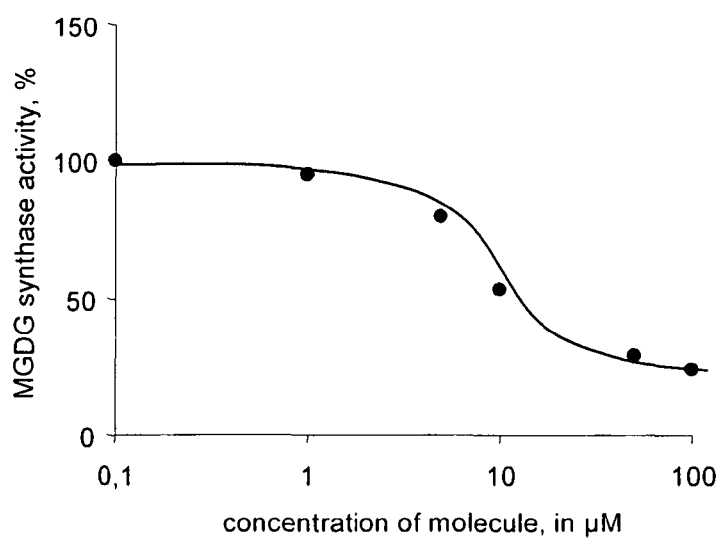
FIG. 4 shows the effect of Compound (7) on the MGDG synthase activity measured in the membrane compartment surrounding spinach chloroplast.
Figure 5:
FIG. 5 shows the herbicidal effect of glyphosate and triclosan compared to each of Compounds (17), (13), (16) and (23).
Figure 5:
Figure 5:
Figure 5:
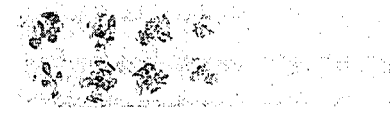
Figure 5:
Figure 5:
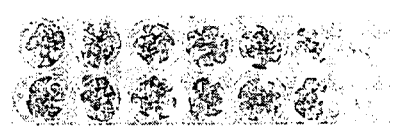

Besides the arrangements above, the invention also comprises other arrangements which will emerge from the following description, which refers to examples of preparation of compounds of formula (I) according to the invention and to in vitro demonstration of the herbicide and/or algaecide activity of compounds of formula (I), and to the annexed figures in which:

FIG. 1 represents the Phylogeny of MGD and MURG. Full-length sequences of plant and algal MGDG synthases and of bacterial MURG were obtained via the National Center for Biotechnology Information (NCBI) web site (http://www.ncbi.nlm.nih.gov/). On this figure, MGD sequences obtained from six Angiosperms are labelled as: at, *Arabidopsis thaliana* [atMGD1, accession number BAB12042; atMGD2, accession number T52269 and atMGD3, accession number BAB12041]; cs, *Cucumis sativa* [csMGD1, accession number AAC49624.1]; gm, *Glycine max* [gmMGD1, accession number BAB 11979]; nt, *Nicotiana tabacum* [ntMGD1, accession number BAB 11980]; *Oryza sativa* [osMGD1, accession number BAD33425 and osMGD2, accession number XM_481404)] and so, *Spinacia oleracea* [soMGD1, accession number CAB56218]. MGD sequence obtained from a Bryophyte is labelled as: pp, *Physcomitrella patens* [ppMGD corresponding to the clustered expressed sequence tags Php_AX155049, Php_dbEST_Id: 10946475_Frame-2 and Php_AX150691_Frame-3 obtained in August 2004 via the Moss Genome Initiative web site, http://www.leeds.moss.ac.uk. MGD sequence obtained from a Rhodophyte was labelled as: cm, *Cyanidoschyzon merolae* [cmMGD registered as #3974 in the Cyanidioschyzon Genome Project web site, http://merolae.biol.s.u-tokyo.ac.jp/). MGD sequence obtained from a Heterokont was labelled as: tp, *Thalassiosira pseudonana* [tpMGD1, a full-length sequence corresponding to Thp_grail.23.172.1 and Thp_newV2.0.genewise.23.85.1; tpMGD2, a partial sequence corresponding to Thp_grail.120.10.1 and tpMGD3, a partial sequence corresponding to genewise.89.116.1, obtained via the DOE Joint Genome Institute http://genome.jgi-psf.org/thaps1/thaps1.home.html]. Eight prokaryotic sequences of MURG enzymes were labelled as: bb, *Bartonella bacilliformins* [bbMURG, accession number AAT38530]; bs, *Bacillus subtilis* [bsMURG, accession number P37585]; ec, *Escherichia coli* [ecMURG, accession number CAA38867], li, *Listeria innocua* [liMURG, accession number NP_471475]; ll, *Lactococcus lactis* [llMURG, accession number NP_267745]; ma, *Mycobacterium avium* [maMURG, accession number NP_960831]; sy, *Synechocystis* sp. PCC 6803 [syMURG, accession number NP_442963]; vv, *Vibrio vulnificus* [vvMURG, accession number Q7MNV1]. These sequences were identified by BLASTP similarity searches with an Expected value lower that 10.E-2, and selected for their representation of phylogenetic diversity. All sequences were used to build a phylogenetic tree according to Botté, C. et al., 2005, (previously cited). Obtained phylogenetic tree shows related groups corresponding to MGD sequences from plastids of "green lineage" and "red lineage" and MURG sequences. The MURG/MGD phylogenic discontinuity correlates with a functional discontinuity for substrates (Lipid 1 for MURG/Diacylglycerol for MGD and UDP-GlcNac for MURG/UDP-Gal for MGD) and the "red lineage"/"green lineage" discontinuity correlates with a functional discontinuity in used DAG molecular species (diacylglycerol of $C_{16}$-$C_{18}$ acyl-length/ diacylglycerol of $C_{16}$-$C_{18}$-$C_{20}$ acyl-length). In Angiosperms, the type A and type B clusters also correspond to differences in enzyme specificity for diacylglycerol molecular species;

FIG. 2 represents the effect of (S)-2-(dibenzylamino)propyl 4-(1,2-dihydro-2-oxobenzo[d]imidazol-3-yl)piperidine-1-carboxylate [compounds (7)] and of S)-2-(dibenzylamino)-3-phenylpropyl 4-(1,2-dihydro-2-oxobenzo[d]imidazol-3-yl)piperidine-1-carboxylate [compound (8)] on the activity of spinach recombinant MGDG synthase (soMGD) compared to known herbicides, i.e. nisin and vancomycin as negative controls. On this figure, MGDG synthase activity (%) is a function of the concentration of the tested compound (µM);

FIG. 3 shows the effect of compounds (7) and (8) on the activity of *Arabidopsis* recombinant MGDG synthase atMGD1, atMGD2 and atMGD3. On this figure, MGDG synthase activity (%) is a function of the concentration of the tested compound (µM);

FIG. 4 represents the effect of compound (7) on the MGDG synthase activity measured in the membrane compartment surrounding spinach chloroplast. On this figure, MGDG synthase activity (%) is a function of the concentration of the tested compound (µM);

FIG. 5 shows the herbicidal effect of glyphosate and triclosan, two known herbicides, compared to 4 compounds of formula (I) according to the invention (Compounds 17, 13, 16 and 23).

It should be clearly understood, however, that these examples are given only by way of illustration of the subject of the invention, of which they in no way constitute a limitation.

EXAMPLES

Example 1

Synthesis of Compounds of Formula (I). General Protocols and Particular Examples Commercial reagents used in the following examples were purchased from Aldrich and were used as received without additional purification. All reactions were carried out under nitrogen with dry, freshly distilled solvents and oven- or flame-dried glassware.

For solid phase synthesis, the moderate-scale reactions (100-500 mg of resin) were carried out using flasks fitted with a frit at the bottom and a stopper. All solid phase reactions were agitated by variable speed orbital mixer. Merrifield® resin was obtained from Aldrich (100-200 mesh; 1% cross-linked; loading: 1.97 mmol/g).

Chromatography was carried out on Merck silica gel 60 (particle size 230-400 mesh). Thin layer chromatography (TLC) was performed on a 0.2 mm precoated plates of silica gel referenced 60E-264 by Merck. Visualization was made with ultraviolet light or iodide or phosphomolibdic acid spray. Preparative TLC was performed on a 1.0 mm precoated plates of silica gel referenced 60E-264 (Whatman). Visualization was made with ultraviolet light.

$^1$H and $^{13}$C NMR spectra were recorded on a Brucker Avance® 400 with a BBO probe.

IR spectra of resin materials in KBr tablets were taken with a Perkin Elmer® 2000 FTIR (Fourier Transform Infrared).

Analytical Method for LC/MS:

Column: Xbridge $C_{18}$ 3-5 µM, 4.6 mm×100 mm

Flow rate: 1.0 mL/min

Detector: Photodiode Array Detector Waters 2996: UV (200-400 nm), PL-ELS 1000, MS ZQ 2000.

Injection volume: 1 µL using Autosampler: Waters 2767

Method: 95% A, 5% B to 0% A, 100% B with 8 minutes gradient then 5 minutes hold.

A: 100% water, 0.1% formic acid

B: 100% acetonitrile

Mitsunobu Procedure:

To a stirred suspension of appropriate heterocycle (0.37 mmol, 2 equiv.), (S)-2-(dibenzylamino)propyl 4-hydroxypiperidine-1-carboxylate (70 mg, 0.18 mmol) and $PPh_3$ (72 mg, 0.27 mmol) in tetrahydrofurane (THF) (4 mL) cooled to 0° C. under $N_2$, 43 µl (0.27 mmol) of diethyl azodicarboxylate (DEAD) was added dropwise. The resulting mixture was allowed to warm to room temperature and stirred for 2 days. The solvent was evaporated. The residue was purified by appropriate method.

Preparation of (S)-2-(dibenzylamino)propyl 4-(1H-benzo[d]imidazol-1-yl)piperidine-1-carboxylate (Compound no 1)

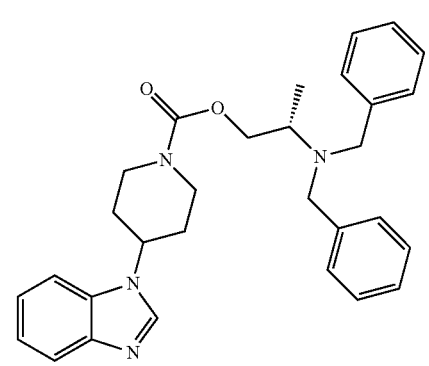

(1)

This compound has been prepared from benzimidazole and (S)-2-(dibenzylamino)propyl 4-hydroxypiperidine-1-carboxylate Colorless oil (65%).

Preparative LCMS

LC/MS (ES$^+$) m/z 483.1 (M+H)$^+$

Tropinone Derivative Preparation (2 Steps)

Step 1: Synthesis of 8-azabicyclo[3.2.1]octan-3-one (Intermediate)

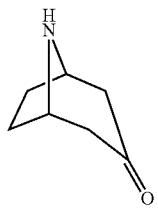

To a stirred solution of ethyl 3-oxo-8-azabicyclo[3.2.1]octane-8-carboxylate (500 mg, 2.53 mmol) in 1,2-dichloroethane (10 mL) was added 369 μL (2.60 mmol) of trimethylsilyl iodide (TMSI) under a nitrogen atmosphere. The reaction mixture was heated at 60° C. for 4 h and cooled to room temperature. Methanol (10 mL) was added and the mixture was stirred for 30 min at room temperature (rt). The solvent was removed on vacuo and the residue was partitioned between $CH_2Cl_2$ and 1M aqueous NaOH solution (5 mL). The mixture was extracted with $CH_2Cl_2$ (3×10 mL). The organic layers were dried over anhydrous $Na_2SO_4$, filtered and concentrated under vacuum. The crude material was purified by flash chromatography (silica gel, methylene chloride/EtOH/$NEt_3$ 85/10/5) to afford a pale yellow oil (140 mg, 44%).

$^1$H NMR (400 MHz, $CDCl_3$) δ 3.82 (m, 2H, CHNH), 2.50 (m, 3H, $CH_2CO$, NH), 2.27 (m, 2H, $CH_2CO$), 1.84 (m, 2H, $CHCH_2CH_2$), 1.62 (m, 2H, $CHCH_2CH_2$).

Step 2: (S)-2-(dibenzylamino)propyl 3-oxo-8-azabicyclo[3.2.1]octane-8-carboxylate (Intermediate)

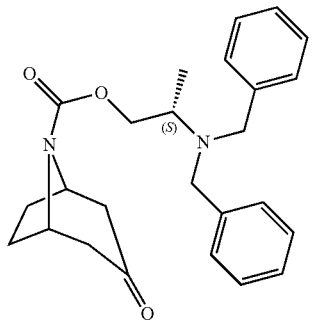

To a stirred solution of (S)-2-(dibenzylamino)propan-1-ol (137 mg, 0.54 mmol) in THF (2.5 mL) at 0° C. was added carbonyldiimidazol (CDI) (96 mg, 0.59 mmol) under $N_2$ atmosphere. The reaction mixture was stirred for 2 h at room temperature. The 8-azabicyclo[3.2.1]octan-3-one as obtained here above at step 1 (140 mg, 1.12 mmol) in THF (1 mL) was added and the reaction mixture was heated at 50° C. for 48 h. The solvent was removed on vacuo and the crude material was purified by flash chromatography (silica gel, cyclohexane/ethyl acetate 8/2) to afford a pale yellow oil (70 mg, 32%).

$^1$H NMR (400 MHz, $CDCl_3$) δ 7.35 (d, J=7.2 Hz, 4H, Bn), 7.28-7.19 (m, 6H, Bn), 4.54 (m, 2H, CHNH), 4.27 (m, 1H, $CH_2O$), 4.08 (m, 1H, $CH_2O$), 3.75 (d, J=14.0 Hz, 2H, $NCH_2Ph$), 3.55 (d, J=14.0 Hz, 2H, $NCH_2Ph$), 3.15 (m, 1H, CHMe), 2.64 (m, 2H, $CH_2CO$), 2.36 (m, 2H, $CH_2CO$), 2.10 (m, 2H, $CHCH_2CH_2$), 1.80 (m, 2H, $CHCH_2CH_2$), 1.10 (d, J=6.8 Hz, 3H, Me)

LC/MS ($ES^+$) m/z 407.2 $(M+H)^+$

"Seven-Member Cycle" Derivative

Step 1: azepan-4-one hydrochloride (Intermediate)

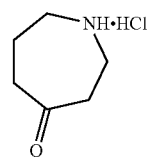

To a stirred solution of N-carbethoxy-4-piperidone (600 mg, 3.00 mmol) in anhydrous $Et_2O$ (1.5 mL) were simultaneously added solutions of $BF_3.Et_2O$ (380 μL, 3.00 mmol) and ethyl diazoacetate (412 μL, 3.92 mmol), each in anhydrous $Et_2O$ (0.4 mL) at −35° C. under a nitrogen atmosphere. The reaction mixture was stirred for 1 h 30 at −35° C. and allowed to warm to room temperature. The solution was washed with 30% aqueous $K_2CO_3$ solution (3 mL) and the organic phase was extracted with ethyl acetate (3×5 mL). The organic layers were dried over anhydrous $Na_2SO_4$, filtered and concentrated under vacuum. The crude material was refluxed in 4N aqueous HCl (13 mL) for 6 h and the solvent was removed on vacuo to afford a pale yellow oil (400 mg, 88%).

$^1$H NMR (400 MHz, $CDCl_3$) δ 3.04 (m, 4H, $CH_2NH$), 2.59 (m, 4H, $CH_2CO$), 1.86 (m, 1H, NH), 1.75 (m, 2H, $CH_2CH_2NH$).

Step 2: (S)-2-(dibenzylamino)propyl 4-oxoazepane-1-carboxylate (Intermediate)

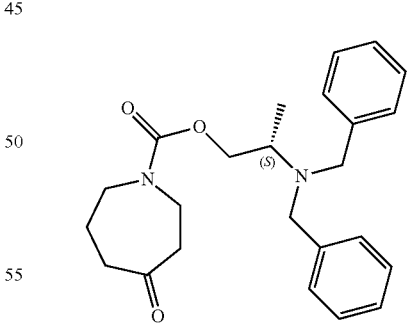

To a stirred solution of the (S)-2-(dibenzylamino)propan-1-ol (285 mg, 1.20 mmol) in THF (6 mL) at 0° C. was added CDI (213 mg, 1.30 mmol) under $N_2$ atmosphere. The reaction mixture was stirred for 2 h at room temperature. The azepan-4-one hydrochloride as obtained here above at step 1 (140 mg, 1.12 mmol) in dimethylformamide (DMF) (4 mL) and triethylamine (TEA) (568 μL, 4.00 mmol) were added and the reaction mixture was heated at 50° C. for 72 h. The solvent was removed on vacuo and the crude material was purified by flash chromatography (silica gel, cyclohexane/ethyl acetate 5/5) to afford a pale yellow oil (20 mg, 4%).

$^1$H NMR (400 MHz, CDCl$_3$) δ 7.35 (d, J=7.2 Hz, 4H, Bn), 7.28 (t, J=7.2 Hz, 4H, Bn), 7.22 (t, J=7.2 Hz, 2H, Bn), 4.22 (dd, J=11.2, 7.2 Hz, 1H, CH$_2$O), 4.02 (dd, J=11.2, 5.6 Hz, 1H, CH$_2$O), 3.73 (d, J=14.0 Hz, 2H, NCH$_2$Ph), 3.64 (m, 4H, CH$_2$CH$_2$N, CH$_2$CH$_2$CH$_2$N), 3.54 (d, J=14.0 Hz, 2H, NCH$_2$Ph), 3.12 (m, 1H, CHMe), 2.67 (m, 4H, CH$_2$CH$_2$N, CH$_2$CH$_2$CH$_2$N), 1.80 (m, 2H, CH$_2$CH$_2$CH$_2$N), 1.08 (d, J=4.4 Hz, 3H, Me).

LC/MS (ES$^+$) m/z 395.2 (M+H)$^+$

Reductive Amination:

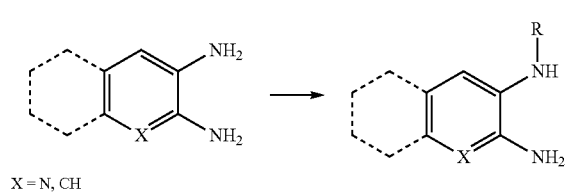

X = N, CH

General Procedure:

To a stirred solution of appropriate diamine (3 equiv.) in 1,2-dichloroethane (1 mL/mmol) were added appropriate ketone (1 equiv.), acetic acid (1.7 equiv.) followed by sodium triacetoxyborohydride (1.9 equiv.) under a nitrogen atmosphere. The reaction mixture was stirred for 16 h at room temperature. The solvent was removed on vacuo and the residue was partitioned between ethyl acetate and 2M aqueous Na$_2$CO$_3$ solution (5 mL/mmol). The organic phase was separated and washed by 2M aqueous Na$_2$CO$_3$ solution (2×5 mL/mmol). The organic layer was dried over anhydrous Na$_2$SO$_4$, filtered and concentrated under vacuum. The crude material was purified by flash chromatography on silica gel.

(S)-2-(dibenzylamino)propyl 4-(2-aminopyridin-3-ylamino)piperidine-1-carboxylate (Intermediate)

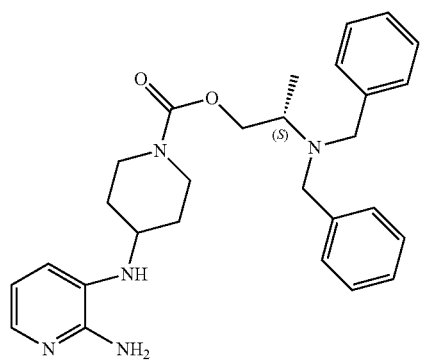

This compound has been obtained from pyridine-2,3-diamine and (S)-2-(dibenzylamino)propyl 4-oxopiperidine-1-carboxylate.

Flash chromatography on silica gel (methylene chloride/ethanol 95/5).

Yellow solid (40%).

LC/MS (ES$^+$) m/z 474.2 (M+H)$^+$

N-(1-benzylpyrrolidin-3-yl)benzene-1,2-diamine (Intermediate)

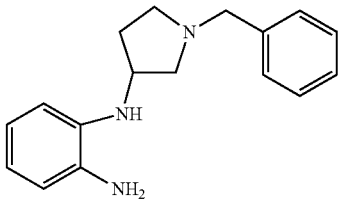 [SMILES: Nc1ccccc1NC1CCN(Cc2ccccc2)C1]

This compound has been obtained from benzene-1,2-diamine and 1-benzylpyrrolidin-3-one.

Flash chromatography on silica gel (ethyl acetate).

Brown oil (40%).

LC/MS (ES$^+$) m/z 268.2 (M+H)$^+$ (S)-2-(dibenzylamino)propyl 3-(2-aminophenylamino)-8-azabicyclo[3.2.1]octane-8-carboxylate (Intermediate)

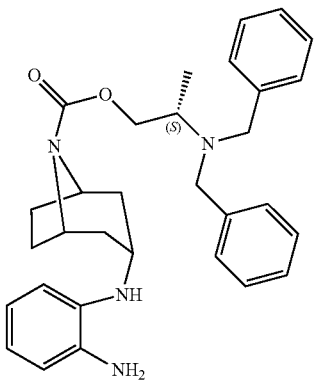

This compound has been obtained from benzene-1,2-diamine and (S)-2-(dibenzylamino)propyl 3-oxo-8-azabicyclo[3.2.1]octane-8-carboxylate.

Flash chromatography on silica gel (cyclohexane/ethyl acetate 5/5)

Yellow oil (45%).

LC/MS (ES$^+$) m/z 499.2 (M+H)$^+$ (S)-2-(dibenzylamino)propyl 4-(2-aminophenylamino)azepane-1-carboxylate (Intermediate)

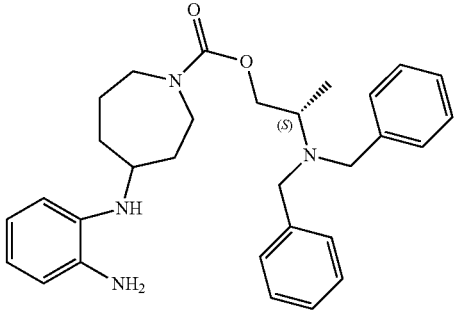

This compound has been obtained from benzene-1,2-diamine and (S)-2-(dibenzylamino)propyl 4-oxoazepane-1-carboxylate.

Flash chromatography on silica gel (cyclohexane/ethyl acetate 6/4).

Orange oil (58%).

LC/MS (ES$^+$) m/z 487.2 (M+H)$^+$

Ethyl 4-(2-aminophenylamino)cyclohexanecarboxylate (Intermediate)

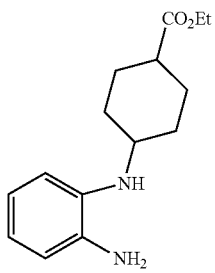 [SMILES: CCOC(=O)C1CCC(Nc2ccccc2N)CC1]

This compound has been obtained from benzene-1,2-diamine and ethyl 4-oxocyclohexanecarboxylate.

Flash chromatography on silica gel (methylene chloride/ether 95/5).

Brown oil (68%).

LC/MS (ES$^+$) m/z 263.3 (M+H)$^+$

Cyclisation (CDI):

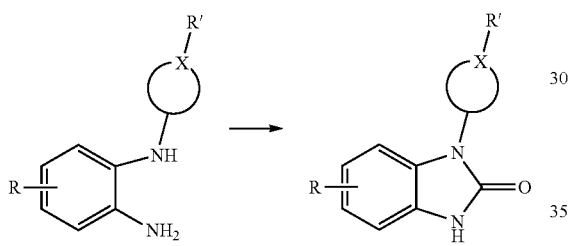

General Procedure:

To a stirred solution of appropriate diamine (1 equiv.) in THF (10 mL/mmol) was added CDI (1.5 equiv) under $N_2$ atmosphere. The reaction mixture was stirred overnight at room temperature. The solvent was removed on vacuo and the residue was purified by flash chromatography on silica gel.

Preparation of (S)-2-(dibenzylamino)propyl 4-(2,3-dihydro-2-oxoimidazo[4,5-b]pyridin-1-yl)piperidine-1-carboxylate (Compound no 2)

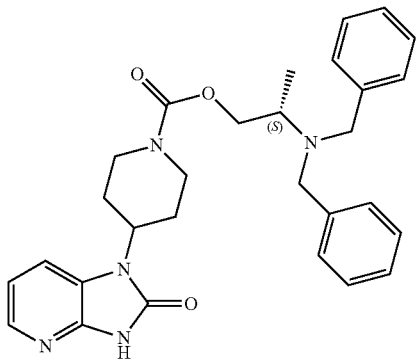

(2)

This compound has been obtained from (S)-2-(dibenzylamino)propyl 4-(2-aminopyridin-3-ylamino)piperidine-1-carboxylate.

Stirred for 2 days at room temperature.

Flash chromatography on silica gel (methylene chloride/acetone 7/3)

Colorless oil (57%).

$^1$H NMR (400 MHz, CDCl$_3$) δ 10.34 (bs, 1H, NH), 8.07 (d, J=5.2 Hz, 1H, Ar), 7.37 (m, 4H, Ar), 7.28-7.21 (m, 7H, Ar), 6.95 (t, J=7.6 Hz, 1H, Ar), 4.60 (m, 1H, CHCH$_2$CH$_2$N$_{pip}$), 4.40 (m, 2H, CHCH$_2$CH$_2$N$_{pip}$), 4.27 (m, 1H, CH$_2$O), 4.08 (dd, J=5.2, 10.4 Hz, 1H, CH$_2$O), 3.76 (d, J=13.8 Hz, 2H, NCH$_2$Ph), 3.56 (d, J=13.8 Hz, 2H, NCH$_2$Ph), 3.14 (m, 1H, CHMe), 2.94 (m, 2H, CHCH$_2$CH$_2$N$_{pip}$), 2.24 (m, 2H, CHCH$_2$CH$_2$N$_{pip}$), 1.92 (m, 2H, CHCH$_2$CH$_2$N$_{pip}$), 1.11 (d, J=6.4 Hz, 3H, Me).

$^{13}$C NMR (100 MHz, CDCl$_3$) δ 155.1 (C=O), 153.3 (C=O), 143.1 (C$_{Ar}$), 140.2 (C$_{Ar}$), 140.1 (CH$_{Ar}$), 133.1 (C$_{Ar}$), 128.6 (CH$_{Ar}$), 128.2 (CH$_{Ar}$), 126.8 (CH$_{Ar}$), 116.8 (CH$_{Ar}$), 115.4 (CH$_{Ar}$), 66.9 (CH$_2$O), 53.4 (NCH$_2$Ph), 51.6 (CHMe), 50.1 (CHCH$_2$CH$_2$N$_{pip}$), 43.1 (CHCH$_2$CH$_2$N$_{pip}$), 28.9 (CHCH$_2$CH$_2$N$_{pip}$), 11.9 (Me).

LC/MS (ES$^+$) m/z 500.2 (M+H)$^+$

Preparation of (S)-2-(dibenzylamino)propyl 3-(2-oxo-2,3-dihydro-1H-benzo[d]imidazol-1-yl)-8-azabicyclo[3.2.1]octane-8-carboxylate (Compound no 3)

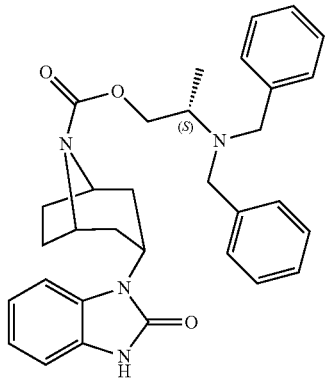

(3)

This compound has been obtained from (S)-2-(dibenzylamino)propyl 3-(2-aminophenylamino)-8-azabicyclo[3.2.1]octane-8-carboxylate.

Preparative TLC (silica gel) (cyclohexane/ethyl acetate 5/5).

Orange oil (56%).

$^1$H NMR (400 MHz, CDCl$_3$) δ 8.45 (bs, 1H, NH), 7.39 (m, 4H, Ar), 7.29 (m, 4H, Ar), 7.20 (m, 2H, Ar), 7.05 (m, 3H, Ar), 6.95 (m, 1H, Ar), 4.55 (m, 3H, CHCH$_2$CHN, CHCH$_2$CHN), 4.29 (m, 2H, CH$_2$O), 3.76 (d, J=13.6 Hz, 2H, NCH$_2$Ph), 3.59 (bd, J=13.6 Hz, 2H, NCH$_2$Ph), 3.15 (m, 1H, CHMe), 2.52 (m, 2H, CH$_2$CHN), 2.49 (m, 2H, CHCH$_2$CHN), 2.19 (m, 2H, CHCH$_2$CHN), 1.92 (m, 2H, CH$_2$CHN), 1.12 (d, J=6.8 Hz, 3H, Me).

LC/MS (ES$^+$) m/z 525.3 (M+H)$^+$

Preparation of (S)-2-(dibenzylamino)propyl 4-(1,2-dihydro-2-oxobenzo[d]imidazol-3-yl)azepane-1-carboxylate (Compound no 4)

(4)

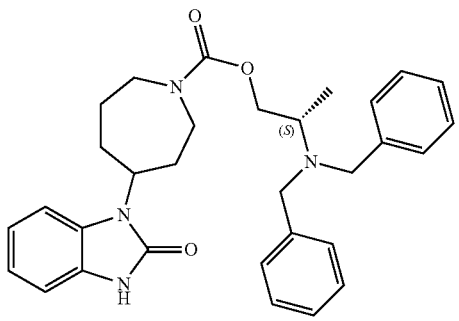

This compound has been obtained from (S)-2-(dibenzylamino)propyl 4-(2-aminophenylamino)azepane-1-carboxylate.

Flash chromatography on silica gel (cyclohexane/ethyl acetate 5/5).

Colorless oil (66%).

$^1$H NMR (400 MHz, CDCl$_3$) δ 9.37 (bd, 1H, NH), 7.39-7.21 (m, 10H, Ar), 7.04 (m, 4H, Ar), 4.46 (m, 1H, CHCH$_2$CH$_2$N), 4.28 (m, 1H, CH$_2$O), 4.12 (m, 1H, CH$_2$O), 3.72 (m, 3H, NCH$_2$Ph, CH$_2$CH$_2$CH$_2$N), 3.61 (m, 4H, NCH$_2$Ph, CHCH$_2$CH$_2$N), 3.33 (m, 1H, CH$_2$CH$_2$CH$_2$N), 3.14 (m, 1H, CHMe), 2.36 (m, 2H, CHCH$_2$CH$_2$N), 2.05 (m, 3H, CH$_2$CH$_2$CH$_2$N, CH$_2$CH$_2$CH$_2$N), 1.72 (m, 1H, CH$_2$CH$_2$CH$_2$N), 1.10 (m, 3H, Me).

$^{13}$C NMR (100 MHz, CDCl$_3$) δ 156.2 (C=O), 154.4 (C=O), 140.3 (140.2) (C$_{Ar}$), 128.9 (128.8) (C$_{Ar}$), 128.6 (128.5) (CH$_{Ar}$), 128.1 (CH$_{Ar}$), 127.9 (127.8) (C$_{Ar}$), 126.8 (126.7) (CH$_{Ar}$), 121.2 (CH$_{Ar}$), 121.1 (121.1) (CH$_{Ar}$), 109.7 (109.6) (CH$_{Ar}$), 109.3 (109.2) (CH$_{Ar}$), 66.8 (CH$_2$O), 53.8 (NCH$_2$Ph), 53.7 (CHCH$_2$CH$_2$N), 51.9 (CHMe), 46.5 (46.6) (CHCH$_2$CH$_2$N), 43.0 (CH$_2$CH$_2$CH$_2$N), 33.0 (32.9) (CHCH$_2$CH$_2$N), 30.1 (CH$_2$CH$_2$CH$_2$N), 26.8 (CH$_2$CH$_2$CH$_2$N), 11.6 (Me).

LC/MS (ES$^+$) m/z 513.3 (M+H)$^+$

Ethyl 4-(1,2-dihydro-2-oxobenzo[d]imidazol-3-yl)cyclohexanecarboxylate (Intermediate)

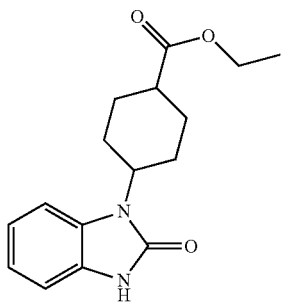 [SMILES: CCOC(=O)C1CCC(n2c(=O)[nH]c3ccccc32)CC1]

This compound has been obtained from ethyl 4-(2-aminophenylamino)cyclohexanecarboxylate.

Pale yellow solid (63%).

Flash chromatography on silica gel (methylene chloride/Et$_2$O 7/3)

$^1$H NMR (400 MHz, CDCl$_3$) δ 10.30 (bs, 1H, NH), 7.20-7.12 (m, 2H, Ar), 7.03 (m, 2H, Ar), 4.44 (m, 1H, NCHCH$_2$CH$_2$), 4.26 (q, J=7.2 Hz, 1H, OCH$_2$CH$_3$), 4.16 (q, J=7.2 Hz, 1H, OCH$_2$CH$_3$), 2.75 (m, 0.5H, CHCO), 2.43-2.05 (m, 4.5H, CHCO, NCHCH$_2$CH$_2$), 1.94 (m, 1H, NCHCH$_2$CH$_2$), 1.73 (m, 3H, NCHCH$_2$CH$_2$), 1.34 (t, J=7.2 Hz, 1.5H, OCH$_2$CH$_3$), 1.28 (t, J=7.2 Hz, 1.5H, OCH$_2$CH$_3$).

$^{13}$C NMR (100 MHz, CDCl$_3$) δ 175.3 (174.9) (C=O$_{Ester}$), 155.4 (155.3) (C=O), 129.2 (128.9) (C$_{Ar}$), 128.3 (128.1) (C$_{Ar}$), 121.2 (121.1) (CH$_{Ar}$), 121.0 (120.9) (CH$_{Ar}$), 109.9 (109.8) (CH$_{Ar}$), 109.2 (CH$_{Ar}$), 60.5 (60.4) (OCH$_2$CH$_3$), 51.8 (51.4) (NCHCH$_2$CH$_2$), 42.4 (37.7) (CHCO), 28.9 (28.5) (NCHCH$_2$CH$_2$), 26.9 (25.9) (NCHCH$_2$CH$_2$), 14.4 (14.2) (OCH$_2$CH$_3$).

LC/MS (ES$^+$) m/z 289.2 (M+H)$^+$

Cyclisation (CDI)/N-Benzyl Deprotection/Carbamate Preparation:

General Procedure

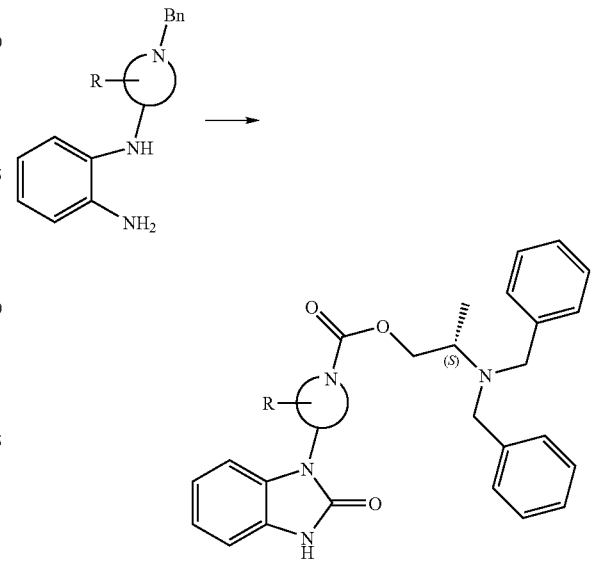

To a stirred solution of appropriate diamine (1 equiv.) in THF (10 mL/mmol) was added CDI (1.5 equiv) under N$_2$ atmosphere. The reaction mixture was stirred overnight at room temperature. The solvent was removed on vacuo. Ethyl acetate was added and the organic layer was washed with water, dried over Na$_2$SO$_4$ and concentrated in vacuo. A solution of the crude material (1 equiv.) in EtOH (10 mL/mmol) was submitted to hydrogenation in the presence of acetic acid (6 equiv.) and 10% Pd/C (100 mg/mmol) at room pressure and temperature for 24 h. The reaction mixture was filtered through a pad of Celite. The filtrate was concentrated under vacuo. To a stirred solution of (S)-2-(dibenzylamino)propan-1-ol (1 equiv.) in THF cooled to 0° C. was added CDI (1.1 equiv.) under N$_2$ atmosphere. The reaction mixture was stirred for 2 h at room temperature. TEA (1.6 equiv.) and the crude salt (1 equiv.) were added and the reaction mixture was stirred for 72 h at room temperature. The solvent was removed on vacuo and the residue was purified by flash chromatography on silica gel.

Preparation of (S)-2-(dibenzylamino)propyl 3-(1,2-dihydro-2-oxobenzo[d]imidazol-3-yl)pyrrolidine-1-carboxylate (Compound no 6)

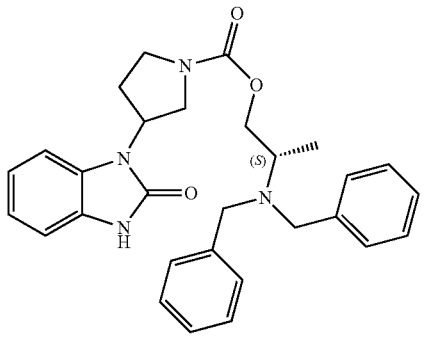

(6)

This compound has been obtained from N-1-(1-benzylpyrrolidin-3-yl)benzene-1,2-diamine.

Flash chromatography on silica gel (cyclohexane/ethyl acetate 5/5).

Yellow oil (12%).

$^1$H NMR (400 MHz, CDCl$_3$) δ 9.07 (bd, 1H, NH), 7.38-7.16 (m, 10H, Ar), 7.09 (m, 4H, Ar), 5.15 (m, 1H, CHCH$_2$N), 4.27 (m, 1H, CH$_2$O), 4.10 (dd, J=5.6, 10.8 Hz, 1H, CH$_2$O), 3.79 (m, 5H, NCH$_2$Ph, CHCH$_2$N, CH$_2$CH$_2$N), 3.56 (m, 3H, NCH$_2$Ph, CH$_2$CH$_2$N), 3.10 (m, 1H, CHMe), 2.63 (m, 1H, CH$_2$CH$_2$N), 2.29 (m, 1H, CH$_2$CH$_2$N), 0.93 (bd, 3H, Me).

LC/MS (ES$^+$) m/z 485.2 (M+H)$^+$

NBoc Deprotection/Carbamate Preparation:
General Procedure

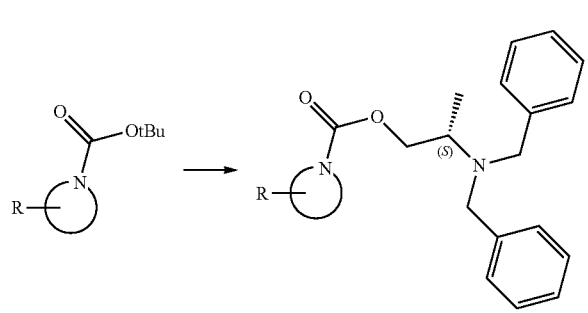

To a stirred solution of appropriate N-tert-butyloxycarbonyl derivative (1 equiv.) in CH$_2$Cl$_2$ (2.5 mL/mmol) cooled to 0° C. under N$_2$ was added TFA (8 equiv.). The reaction mixture was stirred for 2 h at room temperature. The solvent was removed on vacuo and the residue was triturated with Et$_2$O to give a solid. To a stirred solution of (S)-2-(dibenzylamino)propan-1-ol (1 equiv.) in THF (2 mL/mmol) at 0° C. was added CDI (1.1 equiv.) under N$_2$ atmosphere. The reaction mixture was stirred for 2 h at room temperature. Triethylamine (1.8 equiv.) and the crude salt (1.3 equiv.) were added and the reaction mixture was stirred for 72 h at room temperature. The solvent was removed on vacuo and the residue was purified by flash to chromatography on silica gel.

(S)-2-(dibenzylamino)propyl 4-oxopiperidine-1-carboxylate (Intermediate)

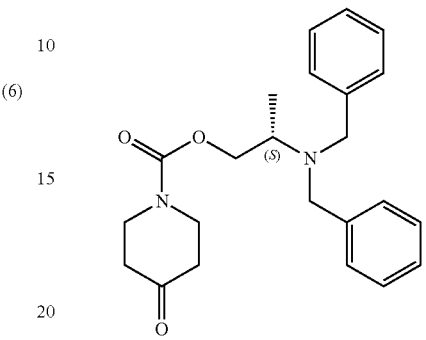

This compound has been obtained from N-tert-butyloxycarbonylpiperid-4-one and (S)-2-(dibenzylamino)propan-1-ol.

Flash chromatography on silica gel (methylene chloride/acetone 97/3)

White solid (31%).

$^1$H NMR (400 MHz, CDCl$_3$) δ 7.35 (d, J=7.2 Hz, 4H, Ar), 7.28 (t, J=7.2 Hz, 4H, Ar), 7.18 (t, J=7.2 Hz, 2H, Ar), 4.27 (dd, J=7.6, 11.2 Hz, 1H, CH$_2$O), 4.06 (dd, J=5.6, 11.2 Hz, 1H, CH$_2$O), 3.75 (m, 6H, NCH$_2$Ph, CH$_2$CH$_2$N$_{pip}$), 3.54 (d, J=13.6 Hz, 2H, NCH$_2$Ph), 3.14 (m, 1H, CHMe), 2.45 (m, 4H, CH$_2$CH$_2$N$_{pip}$), 1.10 (d, J=6.8 Hz, 3H, Me).

LC/MS (ES$^+$) m/z 381.1 (M+H)$^+$ (S)-2-(dibenzylamino)propyl 4-hydroxypiperidine-1-carboxylate (Intermediate)

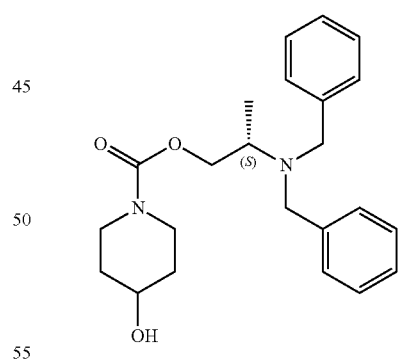

This compound has been obtained from N-tert-butyloxycarbonyl-4-hydroxypiperidine and (S)-2-(dibenzylamino)propan-1-ol.

Flash chromatography on silica gel (cyclohexane/ethyl acetate: 7/3).

Colorless oil (95%).

$^1$H NMR (400 MHz, CDCl$_3$) δ 7.37 (d, J=7.2 Hz, 4H), 7.29 (t, J=7.4 Hz, 4H), 7.23 (m, 2H), 4.22 (dd, J=10.9, 7.5 Hz, 1H, CHCH$_2$CH$_2$N), 4.03 (dd, J=10.9, 5.5 Hz, 1H, OCH$_2$), 3.90 (m, 3H, OCH$_2$, CHCH$_2$CH$_2$N), 3.74 (d, J=13.9 Hz, 2H, NCH$_2$Ph), 3.56 (d, J=13.9 Hz, 2H, NCH$_2$Ph), 3.15 (m, 3H,

CHCH₃, CHCH₂CH2N), 1.89 (d, J=9.0 Hz, 2H, CHCH₂CH₂N), 1.61-1.44 (m, 2H, CHCH₂CH₂N), 1.08 (d, J=6.8 Hz, 3H, CHCH₃)

LC/MS (ES⁺) m/z 383.0 (M+H)⁺

Carbamate Preparation (CDI Coupling):
General Procedure:

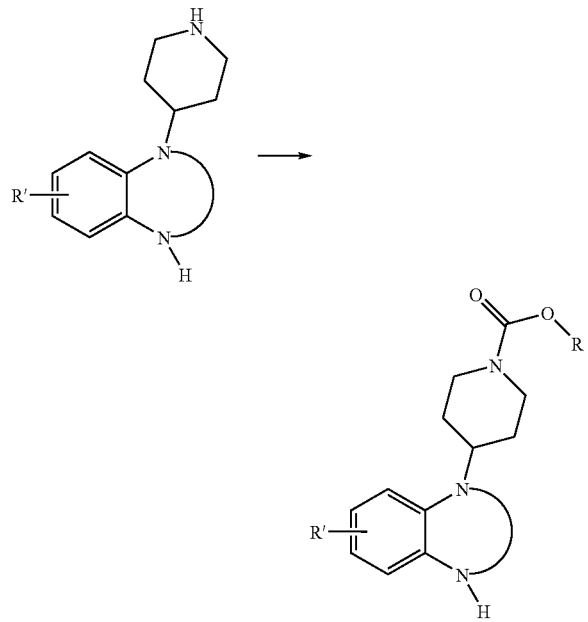

To a stirred solution of the appropriate alcohol (1 equiv.) in THF (2 mL/mmol) at 0° C. was added CDI (1.1 equiv.) under N₂ atmosphere. The reaction mixture was stirred for 2 h at room temperature. The appropriate amine (1.5 equiv.) in THF (10 mL/mmol) was added and the reaction mixture was stirred for 72 h at room temperature. The solvent was removed on vacuo and the residue was purified by flash chromatography on silica gel.

Preparation of (S)-2-(dibenzylamino)propyl 4-(1,2-dihydro-2-oxobenzo[d]imidazol-3-yl)piperidine-1-carboxylate (Compound no 7)

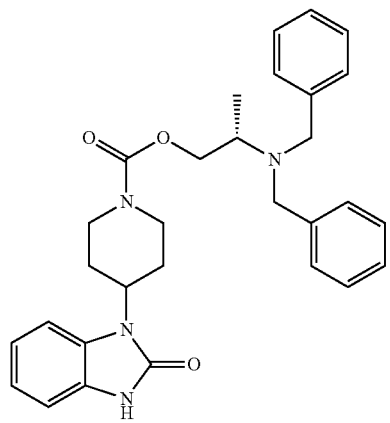

This compound has been obtained from 4-(2-keto-1-benzimidazolinyl)-piperidine and (S)-2-(dibenzylamino)propan-1-ol.

White solid (100%).

Preparative TLC (silica gel, cyclohexane/ethyl acetate 7/3).

¹H NMR (400 MHz, CDCl₃, ppm) δ 10.21 (s, 1H, NH), 7.39 (d, J=7.3 Hz, 4H, Ph), 7.28 (dd, J=12.7, 5.1 Hz, 4H, Ph), 7.21 (t, J=7.3, 2H, Ph), 7.15 (m, 2H, Ph), 7.05 (m, 2H, Ph), 4.53 (tt, J=12.5, 3.8 Hz, 1H, CHCH₂CH₂N), 4.40 (m, 2H, CHCH₂CH₂N), 4.28 (dd, J=11.0, 7.4 Hz, 1H, CH₂O), 4.08 (dd, J=11.0, 5.6 Hz, 1H, CH₂O), 3.78 (d, J=13.9 Hz, 2H, NCH₂Ph), 3.58 (d, J=13.9 Hz, 2H, NCH₂Ph), 3.16 (sext., J=6.3 Hz, 1H, CHCH₃), 2.99 (m, 2H, CHCH₂CH₂N), 2.30 (m, 2H, CHCH₂CH₂N), 1.90 (m, 2H, CHCH₂CH₂N), 1.12 (d, J=6.8 Hz, 3H, CHCH₃)

¹³C NMR (100 MHz, CDCl₃, ppm) δ 155.2, 155.0 (C=O), 140.2, 128.8, 128.5, 128.1, 128.0, 126.7, 121.3, 121.1, 109.8, 109.2 (C$_{Ph}$), 66.8 (CH₂O), 53.7 (NCH₂Ph), 51.9 (CHCH₃), 50.7 (CHCH₂CH₂N), 43.6 (CHCH₂CH₂N), 29.2 (CHCH₂CH₂N), 11.0 (CHCH₃)

LC/MS (ES⁺) m/z 498.9 (M+H)⁺

Preparation of (S)-2-(dibenzylamino)-3-phenylpropyl 4-(1,2-dihydro-2-oxobenzo[d]imidazol-3-yl)piperidine-1-carboxylate (Compound no 8)

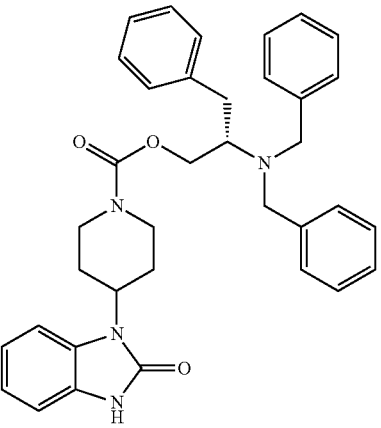

This compound has been obtained from 4-(2-keto-1-benzimidazolinyl)-piperidine and (S)-2-(dibenzylamino)-3-phenylpropan-1-ol.

White solid (80%).

Flash chromatography on silica gel (cyclohexane/ethyl acetate 7/3).

¹H NMR (400 MHz, CDCl₃, ppm) 10.49 (s, 1H, NH), 7.30 (m, 12H, Ph), 7.10 (m, 7H, Ph), 4.46 (m, 1H, CHCH₂CH₂N), 4.45 (m, 2H, CHCH₂CH₂N), 4.38 (m, 1H, CH₂O), 4.22 (m, 1H, CH₂O), 3.83 (d, J=13.8 Hz, 2H, NCH₂Ph), 3.75 (d, J=13.8 Hz, 2H, NCH₂Ph), 3.30 (m, 1H, CHCH₂Ph), 3.10 (dd, J=13.6, 5.8 Hz, 1H, CHCH₂Ph), 2.94 (m, 2H, CHCH₂CH₂N), 2.71 (dd, J=13.6, 8.5 Hz, 1H, CHCH₂Ph), 2.38 (m, 2H, CHCH₂CH₂N), 1.88 (m, 2H, CHCH₂CH₂N)

¹³C NMR (100 MHz, CDCl₃, ppm) δ 155.1, 155.1 (C=O), 139.8, 139.5, 135.0, 129.2, 128.9, 128.8, 128.6, 128.3, 128.3, 128.1, 126.9, 126.8, 126.0, 121.4, 121.1, 121.0, 109.9, 109.3 (CPh), 64.7 (CH₂O), 58.5 (CHCH₂Ph), 54.0 (NCH₂Ph), 50.6 (CHCH₂N), 43.6 (CHCH₂CH₂N), 34.1 (CHCH₂Ph), 29.2 (CHCH₂CH₂N)

LC/MS (ES⁺) m/z 575.1 (M+H)⁺

Preparation of 2-(N-benzyl-N-methylamino)ethyl 4-(1,2-dihydro-2-oxobenzo[d]imidazol-3-yl)piperidine-1-carboxylate (Compound no 9)

(9)

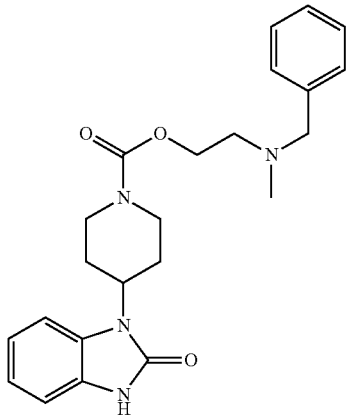

This compound has been obtained from 4-(2-keto-1-benzimidazolinyl)-piperidine and (S)-2-(N,N-benzylmethylamino)propan-1-ol.

Pale Yellow oil (52%).

Preparative TLC (silica gel, dichloromethane/methyl alcohol 85/15).

$^1$H NMR (400 MHz, CDCl$_3$, ppm) δ 10.48 (s, 1H, NH), 7.32 (m, 4H, Ph), 7.24 (m, 1H, Ph), 7.12 (dd, J=7.2, 1.4 Hz, 2H, Ph), 7.04 (m, 2H, Ph), 4.50 (tt, J=12.4, 3.8 Hz, 1H, CHCH$_2$CH$_2$N), 4.37 (m, 2H, CHCH$_2$CH$_2$N), 4.28 (t, J=5.8 Hz, 2H, OCH$_2$CH$_2$N), 3.59 (s, 2H, NCH$_2$Ph), 2.92 (m, 2H, CHCH$_2$CH$_2$N), 2.72 (t, J=5.8 Hz, 2H, OCH$_2$CH$_2$N), 2.35 (m, 5H, CHCH$_2$CH$_2$N, NCH$_3$), 1.85 (m, 2H, CHCH$_2$CH$_2$N)

$^{13}$C NMR (100 MHz, CDCl$_3$, ppm) δ 155.2, 155.1 (C=O), 138.7, 128.9, 128.8, 128.2, 128.1, 127.0, 121.3, 121.0, 109.9, 109.2 (C$_{Ph}$), 63.4 (OCH$_2$CH$_2$N), 62.4 (NCH$_2$Ph), 55.6 (OCH$_2$CH$_2$N), 50.6 (CHCH$_2$CH$_2$N), 43.6 (CHCH$_2$CH$_2$N), 42.7 (NCH$_3$), 29.1 (CHCH$_2$CH$_2$N)

LC/MS (ES$^+$) m/z 409.4 (M+H)$^+$

Preparation of 3-(dibenzylamino)propyl 4-(1,2-dihydro-2-oxobenzo[d]imidazol-3-yl)piperidine-1-carboxylate (Compound no 10)

(10)

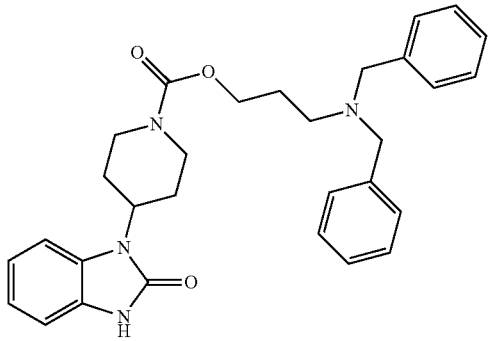

This compound has been obtained from 4-(2-keto-1-benzimidazolinyl)-piperidine and 3-dibenzylaminopropan-1-ol.

White solid (54%).

Preparative TLC (silica gel, cyclohexane/ethyl acetate 1/1).

$^1$H NMR (400 MHz, CDCl$_3$, ppm) δ 10.26 (s, 1H, NH), 7.38 (d, J=7.3 Hz, 4H, Ph), 7.30 (t, J=7.4 Hz, 4H, Ph), 7.23 (m, 2H, Ph), 7.10 (m, 4H, Ph), 4.47 (tt, J=12.4, 3.8 Hz, 1H, CHCH$_2$CH$_2$N), 4.39 (m, 1H, CHCH$_2$CH$_2$N), 4.20 (m, 2H, OCH$_2$CH$_2$CH$_2$N), 3.90 (m, 1H, CHCH$_2$CH$_2$N), 3.58 (s, 4H, NCH$_2$Ph), 2.79 (m, 2H, CHCH$_2$CH$_2$N), 2.54 (t, J=6.1 Hz, 2H, OCH$_2$CH$_2$CH$_2$N), 2.23 (m, 2H, CHCH$_2$CH$_2$N), 1.82 (m, 4H, CHCH$_2$CH$_2$N, OCH$_2$CH$_2$CH$_2$N)

$^{13}$C NMR (100 MHz, CDCl$_3$, ppm) δ 155, 155.1 (C=O), 139.6, 128.8, 128.7, 128.1, 128.1, 126.8, 121.4, 121.1, 109.9, 109.3 (C$_{Ph}$), 63.5 (OCH$_2$CH$_2$CH$_2$N), 58.4 (NCH$_2$Ph), 50.6 (CHCH$_2$CH$_2$N), 49.5 (OCH$_2$CH$_2$CH$_2$N), 43.4 (CHCH$_2$CH$_2$N), 29.1 (CHCH$_2$CH$_2$N), 26.6 (OCH$_2$CH$_2$CH$_2$N)

LC/MS (ES$^+$) m/z 499.1 (M+H)$^+$

Preparation of 2-(dibenzylamino)ethyl 4-(1,2-dihydro-2-oxobenzo[d]imidazol-3-yl)piperidine-1-carboxylate (Compound no 11)

(11)

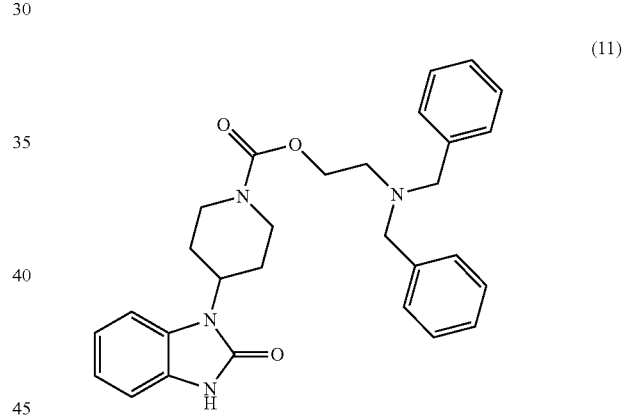

This compound has been obtained from 4-(2-keto-1-benzimidazolinyl)-piperidine and 2-dibenzylaminoethan-1-ol.

White solid (60%).

Preparative TLC (silica gel, cyclohexane/ethyl acetate 1/1).

$^1$H NMR (400 MHz, CDCl$_3$, ppm) δ 10.46 (s, 1H, NH), 7.40 (d, J=7.2 Hz, 4H, Ph), 7.32 (t, J=7.6 Hz, 4H, Ph), 7.24 (m, 2H, Ph), 7.15 (m, 2H, Ph), 7.06 (m, 2H, Ph), 4.54 (m, 1H, CHCH$_2$CH$_2$N), 4.44 (m, 1H, CHCH$_2$CH$_2$N), 4.31 (m, 1H, CHCH$_2$CH$_2$N), 4.26 (t, J=5.6 Hz, 2H, OCH$_2$CH$_2$N), 3.68 (s, 4H, CH$_2$Ph), 2.92 (t, J=11.2 Hz, 2H, CHCH$_2$CH$_2$N), 2.79 (t, J=5.6 Hz, 2H, OCH$_2$CH$_2$N), 2.35 (m, 2H, CHCH$_2$CH$_2$N), 1.86 (d, J=11.2 Hz, 2H, CHCH$_2$CH$_2$N)

$^{13}$C NMR (100 MHz, CDCl$_3$, ppm) δ 155.2, 155.1 (C=O), 139.4, 128.8, 128.8, 128.7, 128.2, 128.1, 127.9, 126.9, 121.3, 121.1, 109.9, 109.3 (C$_{Ph}$), 63.5 (OCH$_2$CH$_2$N), 58.7 (NCH$_2$Ph), 52.1 (OCH$_2$CH$_2$N), 50.7 (CHCH$_2$CH$_2$N), 43.6 (CHCH$_2$CH$_2$N), 29.2 (CHCH$_2$CH$_2$N)

LC/MS (ES$^+$) m/z 485.1 (M+H)$^+$

Preparation of 3,3-diphenylpropyl 4-(1,2-dihydro-2-oxobenzo[d]imidazol-3-yl)piperidine-1-carboxylate (Compound no 12)

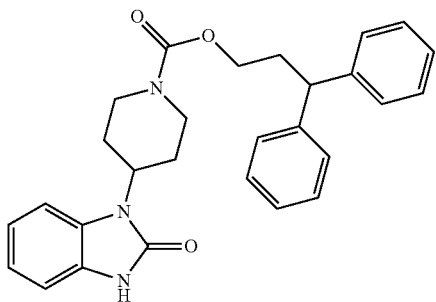

This compound has been obtained from 4-(2-keto-1-benzimidazolinyl)-piperidine and 3,3-diphenyl-propan-1-ol.

Colorless oil (86%).

Preparative TLC (silica gel, cyclohexane/ethyl acetate 8/2).

$^1$H NMR (400 MHz, CDCl$_3$, ppm) δ 9.83 (s, 1H, NH), 7.29 (m, 8H, Ph), 7.19 (m, 2H, Ph), 7.13 (m, 2H, Ph), 7.06 (m, 2H, Ph), 4.49 (tt, J=12.4, 3.7 Hz, 1H, CHCH$_2$CH$_2$N), 4.36 (m, 1H, CHCH$_2$CH$_2$N), 4.13 (m, 4H, CHCH$_2$CH$_2$N, OCH$_2$CH$_2$CHPh$_2$), 2.89 (t, J=12.6 Hz, 2H, CHCH$_2$CH$_2$N), 2.46 (q, J=6.8 Hz, 2H, OCH$_2$CH$_2$CHPh$_2$), 2.32 (m, 2H, CHCH$_2$CH$_2$N), 1.83 (d, J=11.7 Hz, 2H, CHCH$_2$CH$_2$N).

$^{13}$C NMR (100 MHz, CDCl$_3$, ppm) δ 155.2, 154.9 (C=O), 144.2, 128.8, 128.5, 127.9, 127.7, 126.3, 121.4, 121.1, 109.8, 109.3 (C$_{Ph}$), 64.2 (OCH$_2$CH$_2$CHPh$_2$), 50.8, (CHCH$_2$CH$_2$N), 48.0 (OCH$_2$CH$_2$CHPh$_2$), 43.5 (CHCH$_2$CH$_2$N), 34.7 (OCH$_2$CH$_2$CHPh$_2$), 29.2 (CHCH$_2$CH$_2$N).

LC/MS (ES$^+$) m/z 456.1 (M+H)$^+$

Preparation of 1-benzhydrylazetidin-3-yl 4-(1,2-dihydro-2-oxobenzo[d]imidazol-3-yl)piperidine-1-carboxylate (Compound no 13)

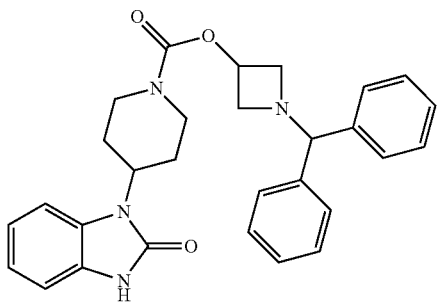

This compound has been obtained from 4-(2-keto-1-benzimidazolinyl)-piperidine and 1-benzhydrylazetidin-3-ol.

White solid (69%).

Preparative TLC (silica gel, cyclohexane/ethyl acetate 7/3).

$^1$H NMR (400 MHz, CDCl$_3$, ppm) δ 9.54 (s, 1H, NH), 7.42 (d, J=7.3 Hz, 4H, Ph), 7.28 (m, 4H, Ph), 7.19 (t, J=7.3 Hz, 2H, Ph), 7.09 (m, 4H, Ph), 5.10 (m, 1H, OCH), 4.49 (tt, J=12.4, 3.9 Hz, 1H, CHCH$_2$CH$_2$N), 4.41 (s, 1H, NCHPh$_2$), 4.35 (m, 2H, CHCH$_2$CH$_2$N), 3.65 (t, J=7.2 Hz, 2H, OCH(CH$_2$)$_2$N), 3.07 (s, 2H, OCH(CH$_2$)$_2$N), 2.89 (m, 2H, CHCH$_2$CH$_2$N), 2.34 (dq, J=12.6, 4.4 Hz, 2H, CHCH$_2$CH$_2$N), 1.86 (d, J=12.6 Hz, 2H, CHCH$_2$CH$_2$N).

LC/MS (ES$^+$) m/z 484.3 (M+H)$^+$

Preparation of 3-(dimethylamino)phenyl 4-(1,2-dihydro-2-oxobenzo[d]imidazol-3-yl)piperidine-1-carboxylate (Compound no 14)

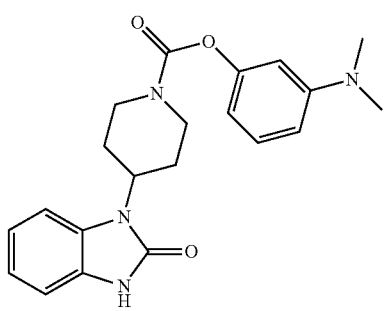

This compound has been obtained from 4-(2-keto-1-benzimidazolinyl)-piperidine and 3-Dimethylamino-phenol Pink solid (72%).

Preparative TLC (silica gel, cyclohexane/ethyl acetate 7/3).

$^1$H NMR (400 MHz, CDCl$_3$, ppm) δ 9.40 (s, 1H, NH), 7.23 (t, J=8.1 Hz, 1H, Ph), 7.19 (dd, J=6.1, 2.9 Hz, 1H, Ph), 7.11 (m, 3H, Ph), 6.59 (dd, J=8.4, 1.6 Hz, 1H, Ph), 6.51 (m, 2H, Ph), 4.54 (m, 3H, CHCH$_2$CH$_2$N), 3.15 (m, 1H, CHCH$_2$CH$_2$N), 3.00 (m, 7H, N(CH$_3$)$_2$, CHCH$_2$CH$_2$N), 2.50 (dq, J=12.7, 4.4Hz, 2H, CHCH$_2$CH$_2$N), 1.94 (d, J=11.7 Hz, 2H, CHCH$_2$CH$_2$N).

$^{13}$C NMR (100 MHz, CDCl$_3$, ppm) δ 154.8 (C=O), 153.9, 152.3 (C$_{Ph}$), 151.6 (C=O), 129.5, 128.9, 127.9, 121.4, 121.2, 114.9, 109.8, 109.6, 109.2, 105.769 (C$_{Ph}$), 50.6 (CHCH$_2$CH$_2$N), 43.9 (CHCH$_2$CH$_2$N), 40.5 (NCH$_3$)$_2$), 29.0 (CHCH$_2$CH$_2$N).

LC/MS (ES$^+$) m/z 381.2 (M+H)$^+$

Preparation of 2-(1,3-dioxoisoindolin-2-yl)ethyl 4-(1,2-dihydro-2-oxobenzo[d]imidazol-3-yl)piperidine-1-carboxylate (Compound no 15)

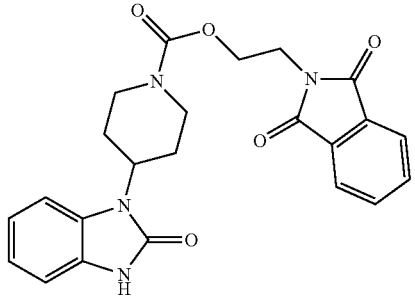

This compound has been obtained from 1-(piperidin-4-yl)-1H-benzo[d]imidazol-2(3H)-one and 2-(2-hydroxyethyl)isoindoline-1,3-dione.

White solid (69%).

Flash chromatography on silica gel (cyclohexane/ethyl acetate 2/8).

$^1$H NMR (400 MHz, CDCl$_3$) δ 9.73 (bs, 1H, NH), 7.85 (dd, J=5.2, 2.8 Hz, 2H, Ar$_{phta}$), 7.70 (dd, J=5.2, 2.8 Hz, 2H, Ar$_{phta}$), 7.43 (m, 1H, Ar), 7.09 (m, 3H, Ar), 4.54 (m, 1H, CHCH$_2$CH$_2$N$_{pip}$), 4.50 (m, 2H, CH$_2$O), 4.41-4.24 (m, 2H, CHCH$_2$CH$_2$N$_{pip}$), 4.02 (m, 2H, CH$_2$CH$_2$O), 2.90 (m, 2H, CHCH$_2$CH$_2$N$_{pip}$), 2.35 (m, 2H, CHCH$_2$CH$_2$N$_{pip}$), 1.85 (m, 2H, CHCH$_2$CH$_2$N$_{pip}$).

$^{13}$C NMR (100 MHz, CDCl$_3$) δ 168.2 (C=O), 154.5 (2×C=O), 134.1 (CH$_{phta}$), 132.0 (C$_{phta}$), 128.8 (C$_{Ar}$), 127.9 (C$_{Ar}$), 123.3 (CH$_{phta}$), 121.4 (CH$_{Ar}$), 121.2 (CH$_{Ar}$), 109.9 (CH$_{Ar}$), 109.7 (CH$_{Ar}$), 63.0 (CH$_2$O), 50.5 (CHCH$_2$CH$_2$N$_{pip}$), 43.6 (CHCH$_2$CH$_2$N$_{pip}$), 37.5 (CH$_2$CH$_2$O), 29.0 (CHCH$_2$CH$_2$N$_{pip}$).

LC/MS (ES$^+$) m/z 435.1 (M+H)$^+$

Preparation of 2-(ethyl(phenyl)amino)ethyl 4-(2-oxo-2,3-dihydro-1H-benzo[d]imidazol-1-yl)piperidine-1-carboxylate (Compound no 17)

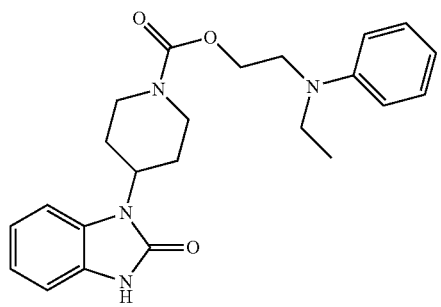

(17)

This compound has been obtained from 1-(piperidin-4-yl)-1H-benzo[d]imidazol-2(3H)-one and 2-(N-ethyl-N-phenylamino)ethanol.

White solid (94%).

Flash chromatography on silica gel (cyclohexane/ethyl acetate 3/7).

$^1$H NMR (400 MHz, CDCl$_3$) δ 8.75 (bs, 1H, NH), 7.22 (m, 2H, Ar), 7.06 (m, 4H, Ar), 6.76 (d, J=8.0 Hz, 2H, Ar), 6.68 (t, J=6.8 Hz, 1H, Ar), 4.48 (m, 1H, CHCH$_2$CH$_2$N$_{pip}$), 4.30 (m, 4H, CHCH$_2$CH$_2$N$_{pip}$, CH$_2$CH$_2$O), 3.61 (t, J=6.4 Hz, 2H, CH$_2$CH$_2$O), 3.44 (q, J=7.2 Hz, 2H, CH$_3$CH$_2$N), 2.93 (m, 2H, CHCH$_2$CH$_2$N$_{pip}$), 2.31 (m, 2H, CHCH$_2$CH$_2$N$_{pip}$), 1.85 (m, 2H, CHCH$_2$CH$_2$N$_{pip}$), 1.20 (t, J=7.2 Hz, 3H, CH$_3$CH$_2$N).

$^{13}$C NMR (100 MHz, CDCl$_3$) δ 155.1 (C=O), 154.9 (C=O), 147.7 (C$_{Ar}$), 129.3 (CH$_{Ar}$), 128.8 (C$_{Ar}$), 127.9 (C$_{Ar}$), 121.3 (CH$_{Ar}$), 121.2 (CH$_{Ar}$), 116.1 (CH$_{Ar}$), 111.9 (CH$_{Ar}$), 109.8 (CH$_{Ar}$), 109.3 (CH$_{Ar}$), 62.8 (CH$_2$CH$_2$O), 50.6 (CHCH$_2$CH$_2$N$_{pip}$), 49.1 (CH$_2$CH$_2$O), 45.0 (CH$_3$CH$_2$N), 43.6 (CHCH$_2$CH$_2$N$_{pip}$), 29.1 (CHCH$_2$CH$_2$N$_{pip}$), 12.3 (CH$_3$CH$_2$N).

LC/MS (ES$^+$) m/z 409.2 (M+H)$^+$

Preparation of 2,2-diphenylethyl 4-(1,2-dihydro-2-oxobenzo[d]imidazol-3-yl)piperidine-1-carboxylate (Compound no 18)

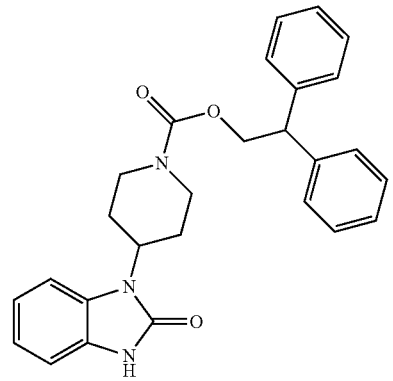

(18)

This compound has been obtained from 1-(piperidin-4-yl)-1H-benzo[d]imidazol-2(3H)-one and 2,2-diphenylethanol.

White solid (75%).

Flash chromatography on silica gel (cyclohexane/ethyl acetate 5/5).

$^1$H NMR (400 MHz, CDCl$_3$) δ 10.3 (bs, 1H, NH), 7.31 (m, 8H, Ar), 7.23 (m, 2H, Ar), 7.12 (m, 1H, Ar), 7.06 (m, 2H, Ar), 7.01 (m, 1H, Ar), 4.73 (m, 2H, CH$_2$O), 4.45 (m, 3H, CHCH$_2$CH$_2$N$_{pip}$, CH(Ph)$_2$), 4.06 (m, 1H, CHCH$_2$CH$_2$N$_{pip}$), 2.83 (m, 2H, CHCH$_2$CH$_2$N$_{pip}$), 2.28 (m, 1H, CHCH$_2$CH$_2$N$_{pip}$), 2.06 (m, 1H, CHCH$_2$CH$_2$N$_{pip}$), 1.80-1.72 (m, 2H, CHCH$_2$CH$_2$N$_{pip}$).

$^{13}$C NMR (100 MHz, CDCl$_3$) δ 155.1 (C=O), 154.9 (C=O), 141.2 (C$_{Ar}$), 128.7 (C$_{Ar}$), 128.5 (CH$_{Ar}$), 128.2 (CH$_{Ar}$), 128.1 (C$_{Ar}$), 126.7 (CH$_{Ar}$), 121.4 (CH$_{Ar}$), 121.1 (CH$_{Ar}$), 109.9 (CH$_{Ar}$), 109.4 (CH$_{Ar}$), 67.8 (CH$_2$O), 50.5 (CHCH$_2$CH$_2$N$_{pip}$), 50.1 (CH(Ph)$_2$), 43.6 (CHCH$_2$CH$_2$N$_{pip}$), 29.0 (CHCH$_2$CH$_2$N$_{pip}$).

LC/MS (ES$^+$) m/z 442.1 (M+H)$^+$

Preparation of (R)-2-(dibenzylamino)-3-phenylpropyl 4-(1,2-dihydro-2-oxobenzo[d]imidazol-3-yl)piperidine-1-carboxylate (Compound no 43)

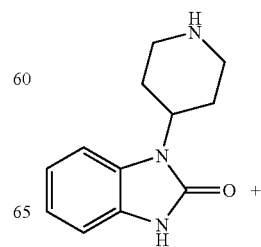

-continued

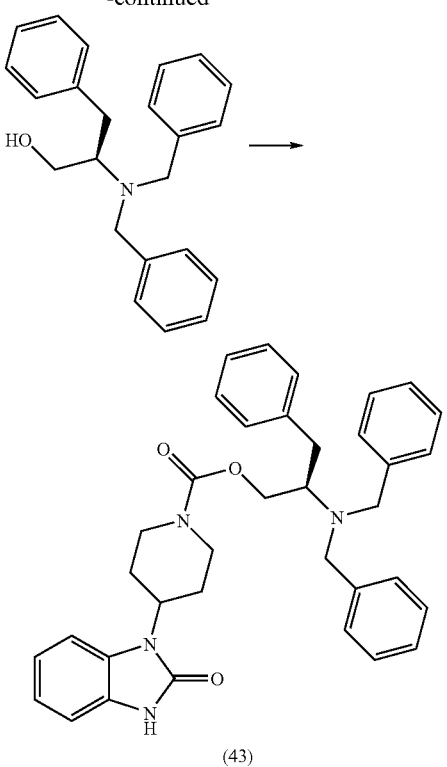

(43)

From 4-(2-keto-1-benzimidazolinyl)-piperidine and (R)-2-(dibenzylamino)-3-phenylpropan-1-ol Pale brown oil (70%).

Flash chromatography on silica gel (cyclohexane/ethyl acetate 8/2)

$^1$H NMR (400 MHz, CDCl$_3$) δ 10.28 (s, 1H, NH), 7.30 (m, 12H, Ph), 7.10 (m, 7H, Ph), 4.53 (m, 1H, CHCH$_2$CH$_2$N), 4.48 (m, 2H, CHCH$_2$CH$_2$N), 4.38 (dd, J=11.2, 6.8 Hz, 1H, CH$_2$O), 4.18 (dd, J=11.2, 4.8 Hz, 1H, CH$_2$O), 3.83 (d, J=13.8 Hz, 2H, NCH$_2$Ph), 3.75 (d, J=13.8 Hz, 2H, NCH$_2$Ph), 3.29 (m, 1H, CHCH$_2$Ph), 3.10 (dd, J=13.6, 6.0 Hz, 1H, CHCH$_2$Ph), 2.92 (m, 2H, CHCH$_2$CH$_2$N), 2.71 (dd, J=13.6, 8.4 Hz, 1H, CHCH$_2$Ph), 2.38 (m, 2H, CHCH$_2$CH$_2$N), 1.88 (m, 2H, CHCH$_2$CH$_2$N)

$^{13}$C NMR (100 MHz, CDCl$_3$) δ 155.3 (C=O), 155.1 (C=O), 139.9, 139.5, 129.3, 128.8, 128.6, 128.4, 128.3, 128.2, 126.9, 126.1, 121.4, 121.1, 110.0, 109.3, 64.8 (CH$_2$O), 58.5 (CHCH$_2$Ph), 54.0 (NCH$_2$Ph), 50.6 (CHCH$_2$CH$_2$N), 43.6 (CHCH$_2$CH$_2$N), 34.1 (CHCH$_2$Ph), 29.2 (CHCH$_2$CH$_2$N)

LC/MS (ES$^+$) m/z 575.2 (M+H)$^+$

General Procedure for Dithiocarbonate Formation

To a solution of appropriate alcohol (2.5 mmol, 1 equiv.) in 5 ml of anhydrous THF was added 120 mg (3.0 mmol, 1.2 equiv.) of sodium hydride at 0° C. and allowed to warm to room temperature for 30 min. After addition of 300 μL (5 mmol, 2 equiv.) of carbon disulfure at 0° C., the reaction was continued for 30 minutes. After addition of 280 μL (4.5 mmol, 1.8 equiv.) of methyl iodide at 0° C., the reaction was continued for 30 minutes. The reaction was quenched by addition of ice and the mixture was extracted by dichloromethane. The dichloromethane layer was dried over sodium sulphate, evaporated and used without further purification.

Dithiocarbonic acid O-(2-dibenzylamino-ethyl)ester S-methyl ester (Intermediate)

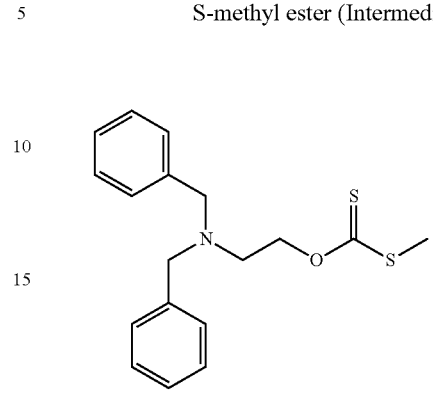

This compound has been obtained from dibenzylamino-ethan-1-ol.

Pale Yellow oil (94%)

$^1$NMR (400 MHz, CDCl$_3$) δ 7.30 (m, 10H, Ph), 4.72 (t, J=5.8 Hz, 2H, OCH$_2$CH$_2$N), 3.69 (s, 4H, NCH$_2$Ph), 2.92 (t, J=5.8 Hz, 2H, OCH$_2$CH$_2$N), 2.56 (s, 3H, SCH$_3$).

LC/MS (ES$^+$) m/z 332.1 (M+H)$^+$

General Procedure for thiocarbamate Formation

To a solution of appropriate dithiocarbonate (1.0 mmol, 1 equiv.) in 1 ml of methyl alcohol was added 260 mg (1.2 mmol, 1.2 equiv.) of 4-(2-keto-1-benzimidazolinyl)-piperidine. The mixture was stirred at 50° C. overnight. The solvent was removed on vacuo and the residue was purified by flash chromatography on silica gel.

Preparation of O-2-(dibenzylamino)ethyl 4-(1,2-dihydro-2-oxobenzo[d]imidazol-3-yl)piperidine-1-carbothioate (Compound no 19)

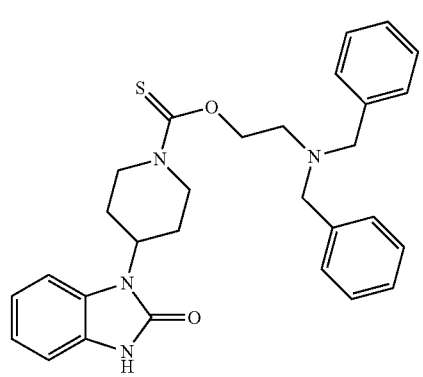

(19)

This compound has been obtained from 4-(2-keto-1-benzimidazolinyl)-piperidine and the corresponding dithiocarbonic ester of 2-dibenzylamino-ethan-1-ol.

White solid (59%).

Flash chromatography on silica gel (cyclohexane/ethyl acetate 7/3).

$^1$H NMR (400 MHz, CDCl$_3$, ppm) δ 10.44 (s, 1H, NH), 7.39 (d, J=7.4 Hz, 4H, Ph), 7.31 (t, J=7.4, 4H, Ph), 7.24 (m, 2H, Ph), 7.17 (d, J=6.8 Hz, 1H, Ph), 7.08 (m, 3H, Ph), 5.40 (d, J=13.5 Hz, 1H, CHCH$_2$CH$_2$N), 4.71 (d, J=13.5 Hz, 1H, CHCH$_2$CH$_2$N), 4.68-4.57 (m, 3H, CHCH$_2$CH$_2$N, OCH$_2$CH$_2$N), 3.68 (s, 4H, NCH$_2$Ph), 3.18 (t, J=12.5 Hz, 1H, CHCH$_2$CH$_2$N), 2.96 (t, J=12.5 Hz, 1H, CHCH$_2$CH$_2$N), 2.88 (t, J=5.6 Hz, 2H, OCH$_2$CH$_2$N), 2.49 (dq, J=12.6, 3.9 Hz, 1H, CHCH$_2$CH$_2$N), 2.31 (dq, J=12.6, 3.9 Hz, 1H, CHCH$_2$CH$_2$N), 1.96 (d, J=12.6 Hz, 1H, CHCH$_2$CH$_2$N), 1.89 (d, J=12.6 Hz, 1H, CHCH$_2$CH$_2$N).

$^{13}$C NMR (100 MHz, CDCl$_3$, ppm) δ 187.4 (C=S), 155.2 (C=O), 139.3, 128.7, 128.6, 128.2, 128.0, 127.0, 121.5, 121.2, 110.0, 109.3 (C$_{Ph}$), 69.6 (OCH$_2$CH$_2$N), 58.7 (NCH$_2$Ph), 51.7 (OCH$_2$CH$_2$N), 50.4 (CHCH$_2$CH$_2$N), 49.5, 44.5 (CHCH$_2$CH$_2$N), 29.1, 28.7 (CHCH$_2$CH$_2$N)

LC/MS (ES$^+$) m/z 500.8 (M+H)$^+$

Preparation of O-2-(benzyloxy)ethyl 4-(1,2-dihydro-2-oxobenzo[d]imidazol-3-yl)piperidine-1-carbothioate (Compound no 20)

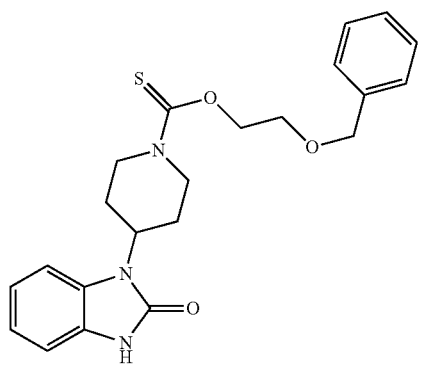

(20)

This compound has been obtained from 4-(2-keto-1-benzimidazolinyl)-piperidine and the corresponding dithiocarbonic ester of 2-benzyloxy-ethan-1-ol.

White solid (91%).

Flash chromatography on silica gel (cyclohexane/ethyl acetate 1/1)

$^1$H NMR (400 MHz, CDCl$_3$, ppm) δ 10.42 (s, 1H, NH), 7.39-7.24 (m, 5H, Ph), 7.20-7.02 (m, 4H, Ph), 5.39 (d, J=13.3 Hz, 1H, CHCH$_2$CH$_2$N), 4.84 (d, J=13.3 Hz, 1H, CHCH$_2$CH$_2$N), 4.73 (m, 2H, OCH$_2$CH$_2$OBn), 4.61 (m, 3H, OCH$_2$Ph, CHCH$_2$CH$_2$N), 3.80 (dd, J=11.1, 6.6 Hz, 2H, OCH$_2$CH$_2$OBn), 3.19 (t, J=12.5 Hz, 1H, CHCH$_2$CH$_2$N), 3.02 (t, J=12.5 Hz, 1H, CHCH$_2$CH$_2$N), 2.50 (dq, J=12.5, 4.0 Hz, 1H, CHCH$_2$CH$_2$N), 2.36 (dq, J=12.5, 4.0 Hz, 1H, CHCH$_2$CH$_2$N), 1.86 (m, 2H, CHCH$_2$CH$_2$N).

$^{13}$C NMR (100 MHz, CDCl$_3$, ppm) δ 187.3 (C=S), 155.1 (C=O), 137.8, 128.6, 128.4, 128.0, 127.8, 127.7, 121.5, 121.2, 110.0, 109.3 (C$_{Ph}$), 73.0 (OCH$_2$Ph), 70.6 (OCH$_2$CH$_2$OBn), 67.9 (OCH$_2$CH$_2$OBn), 50.4 (CHCH$_2$CH$_2$N), 49.6, 44.6 (CHCH$_2$CH$_2$N), 29.1, 28.6 (CHCH$_2$CH$_2$N).

LC/MS (ES$^+$) m/z 412.1 (M+H)$^+$

General Procedure for N-acyl-benzimidazolone Preparation:

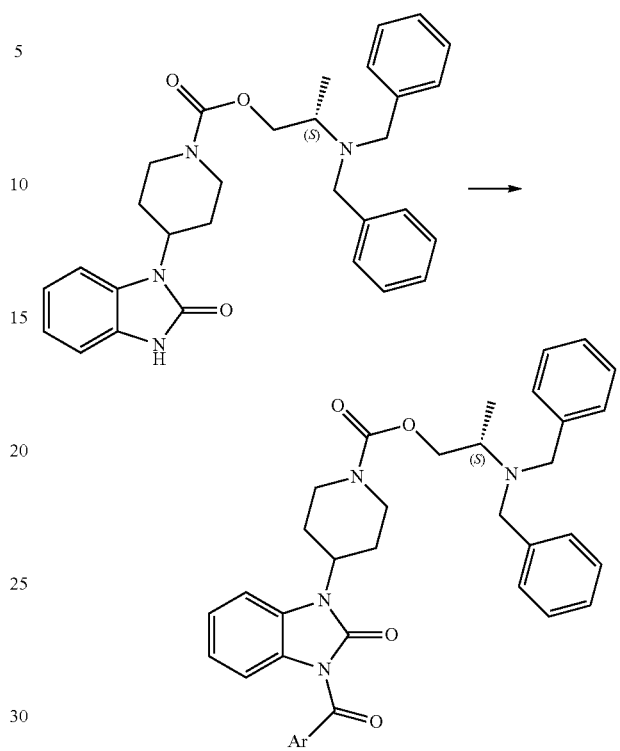

To a stirred solution of the appropriate benzimidazolone derivative (1 equiv.) in THF (20 mL/mmol) at 0° C. was added NaH (60% in mineral oil) (1.2 equiv.) under N$_2$ atmosphere. The reaction mixture was stirred for 1 h at room temperature. The appropriate acyl chloride (1.2 equiv.) was added and the reaction mixture was stirred overnight at room temperature. The solvent was removed on vacuo and the residue was purified by flash chromatography on silica gel.

Preparation of (S)-2-(dibenzylamino)propyl 4-(1,2-dihydro-2-oxo-1-(benzoyl)benzo[d]imidazol-3-yl)piperidine-1-carboxylate (Compound no 21)

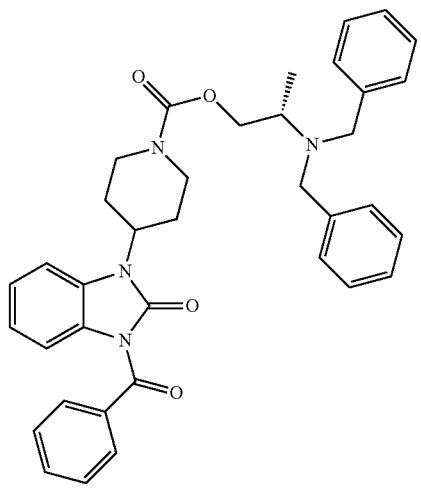

(21)

This compound has been obtained from (S)-2-(dibenzylamino)propyl 4-(1,2-dihydro-2-oxobenzo[d]imidazol-3-yl)piperidine-1-carboxylate and benzoyl chloride.

White solid (67%).
Preparative TLC (silica gel, cyclohexane/ethyl acetate 7/3).

$^1$H NMR (400 MHz, CDCl$_3$, ppm) δ 8.00 (dd, J=6.4, 2.4 Hz, 1H, Ph), 7.79 (d, J=7.3 Hz, 2H, Ph), 7.61 (t, J=7.5 Hz, 1H, Ph), 7.49 (m, 2H, Ph), 7.39 (d, J=7.3 Hz, 4H), 7.28 (m, 4H, Ph), 7.20 (m, 5H, Ph), 4.43 (tt, J=12.2, 3.6 Hz, 1H, CHCH$_2$CH$_2$N), 4.34 (m, 2H, CHCH$_2$CH$_2$N), 4.26 (m, 1H, OCH$_2$), 4.06 (dd, J=11.1, 5.7 Hz, 1H, OCH$_2$), 3.77 (d, J=13.9 Hz, 2H, NCH$_2$Ph), 3.57 (d, J=13.9 Hz, 2H, NCH$_2$Ph), 3.14 (sext., J=6.7 Hz, 1H, CHCH$_3$), 2.89 (m, 2H, CHCH$_2$CH$_2$N), 2.37 (m, 2H, CHCH$_2$CH$_2$N), 1.87 (d, J=10.7 Hz, 2H, CHCH$_2$CH$_2$N), 1.12 (d, J=6.8 Hz, 3H, CHCH$_3$).

$^{13}$C NMR (100 MHz, CDCl$_3$, ppm) δ 168.9, 155.1, 151.4 (C=O), 140.2, 133.8, 132.6, 130.0, 129.2, 129.0, 128.5, 128.4, 128.1, 128.0, 126.9, 126.8, 124.3, 122.4, 114.9, 109.1 (C$_{Ph}$), 66.9 (CH$_2$O), 53.7 (NCH$_2$Ph), 51.9 (CHCH$_3$), 51.5 (CHCH$_2$CH$_2$N), 43.5 (CHCH$_2$CH$_2$N), 28.7 (CHCH$_2$CH$_2$N), 11.2 (CHCH$_3$).

LC/MS (ES$^+$) m/z 602.9 (M+H)$^+$

General Procedure for N-alkyl benzimidazolone Preparation:

To a stirred solution of (0.48 mmol, 1 equiv.) of benzimidazolone derivative in 1 ml of anhydrous DMF was added at 0° C. 21 mg (0.53 mmol, 1.1 equiv.) of sodium hydride. The reaction was pursued for 1 hour. An appropriate alkyl bromide (in these cases, 0.1 equiv. of potassium iodide was added) or iodide in 1 ml of DMF was added at 0° C. The reaction was allowed to warm to room temperature overnight. The mixture was evaporated on vacuum at room temperature and purified on silica gel.

Preparation of (S)-2-(dibenzylamino)-3-phenylpropyl 4-(1,2-dihydro-1-methyl-2-oxobenzo[d]imidazol-3-yl)piperidine-1-carboxylate (Compound no 22)

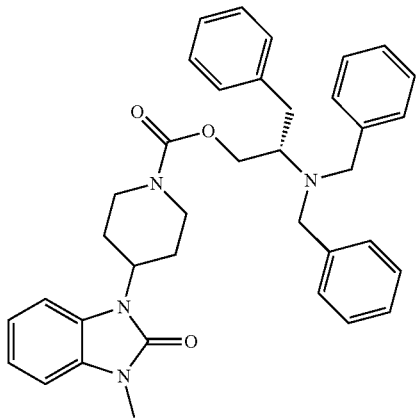

(22)

This compound has been obtained from (S)-2-(dibenzylamino)-3-phenylpropyl 4-(1,2-dihydro-2-oxobenzo[d]imidazol-3-yl)piperidine-1-carboxylate and methyliodide.

White solid (85%).
Preparative TLC (silica gel, cyclohexane/ethyl acetate 1/1).

$^1$H NMR (400 MHz, CDCl$_3$, ppm) δ 7.34-7.17 (m, 13H, Ph), 7.15-6.97 (m, 6H, Ph), 4.54 (tt, J=12.4, 3.8 Hz, 1H, CHCH$_2$CH$_2$N), 4.42 (m, 1H, CHCH$_2$CH$_2$N), 4.36 (dd, J=11.2, 7.0 Hz, 1H, CH$_2$O), 4.26-4.09 (dd$_b$, J=11.2, 4.8 Hz, 2H, CH$_2$O, CHCH$_2$CH$_2$N), 3.78 (2d, J=13.8 Hz, 4H, NCH$_2$Ph), 3.43 (s, 3H, NCH$_3$), 3.28 (m, 1H, CHCH$_2$Ph), 3.09 (dd, J=13.7, 5.9 Hz, 1H, CHCH$_2$Ph), 2.90 (m, 2H, CHCH$_2$CH$_2$N), 2.70 (dd, J=13.7, 8.5 Hz, 1H, CHCH$_2$Ph), 2.33 (m, 2H, CHCH$_2$CH$_2$N), 1.85 (d, J=12.6 Hz, 2H, CHCH$_2$CH$_2$N).

$^{13}$C NMR (100 MHz, CDCl$_3$, ppm) δ 155.1, 153.8 (C=O), 139.8, 139.5, 130.1, 129.2, 128.6, 128.3, 128.1, 127.9, 126.8, 126.0, 121.1, 121.0, 109.0, 107.6 (C$_{Ph}$), 64.7 (CH$_2$O), 58.4 (CHCH$_2$Ph), 53.9 (NCH$_2$Ph), 50.9 (CHCH$_2$CH$_2$N), 43.6 (CHCH$_2$CH$_2$N), 34.1 (CHCH$_2$Ph), 29.2 (CHCH$_2$CH$_2$N), 27.1 (NCH$_3$).

LC/MS (ES$^+$) m/z 589.3 (M+H)$^+$

Thiourea Preparation

N—((S)-2-(dibenzylamino)propyl)-4-(1,2-dihydro-2-oxobenzo[d]imidazol-3-yl)piperidine-1-carbothioamide (Compound no 23)

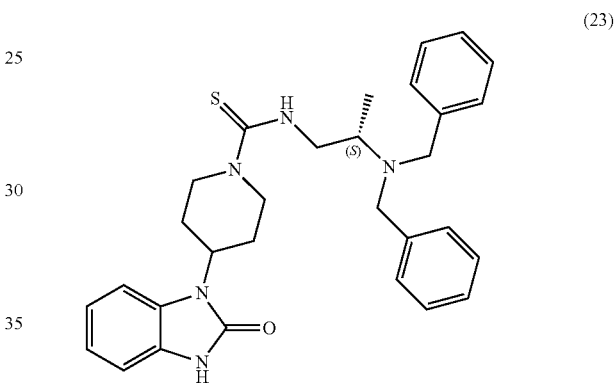

(23)

To a stirred solution of 1-(3-dimethylaminopropyl)-3-ethylcarbodiimide hydrochloride (EDCI) (30 mg, 0.16 mmol) in acetonitrile (0.4 mL) cooled to −10° C. under N$_2$ was added CS$_2$ (94 µL, 1.57 mmol). A solution of (S)—N,N-dibenzylpropane-1,2-diamine (40 mg, 0.16 mmol) in acetonitrile (0.4 mL) was added dropwise. The reaction mixture was stirred for 3 h at room temperature and a solution of 1-(piperidin-4-yl)-1H-benzo[d]imidazol-2(3H)-one (34 mg, 0.16 mmol) in acetonitrile (0.8 mL) was added. The mixture was heated at 55° C. overnight and the solvent was removed on vacuo. The crude material was purified by flash chromatography (silica gel, cyclohexane/ethyl acetate 6/4) to afford a pale yellow solid (32 mg, 40%).

$^1$H NMR (400 MHz, CDCl$_3$) δ 9.09 (bs, 1H, NH), 7.29-7.16 (m, 10H, Ar), 7.09 (m, 4H, Ar), 6.45 (bs, 1H, NH), 4.79-4.56 (m, 3H, CHCH$_2$CH$_2$N$_{pip}$, CHCH$_2$CH$_2$N$_{pip}$), 3.78 (m, 3H, NCH$_2$Ph, CH$_2$NH), 3.33 (m, 3H, NCH$_2$Ph, CH$_2$NH), 3.03 (m, 2H, CHMe, CHCH$_2$CH$_2$N$_{pip}$), 2.42-2.27 (m, 2H, CHCH$_2$CH$_2$N$_{pip}$), 1.92 (m, 2H, CHCH$_2$CH$_2$N$_{pip}$), 1.18 (d, J=6.0 Hz, 3H, Me).

$^{13}$C NMR (100 MHz, CDCl$_3$) δ 180.3 (C=S), 154.9 (C=O), 139.5 (C$_{Bn}$), 129.2 (CH$_{Bn}$), 128.7 (C$_{Ar}$), 128.5 (CH$_{Bn}$), 127.9 (C$_{Ar}$), 127.4 (CH$_{Bn}$), 121.5 (CH$_{Ar}$), 121.3 (CH$_{Ar}$), 109.8 (CH$_{Ar}$), 109.4 (CH$_{Ar}$), 53.7 (NCH$_2$Ph), 51.9 (CHMe), 50.6 (CHCH$_2$CH$_2$N$_{pip}$), 47.2 (CH$_2$NH), 46.7 (CHCH$_2$CH$_2$N$_{pip}$), 28.9 (CHCH$_2$CH$_2$N$_{pip}$), 9.9 (Me).

LC/MS (ES$^+$) m/z 514.2 (M+H)$^+$

"Amide Link" Procedure

Preparation of 1-[1-(4-Dibenzylamino-butyryl)-piperidin-4-yl]-1,3-dihydro-benzoimidazol-2-one (Compound no 24)

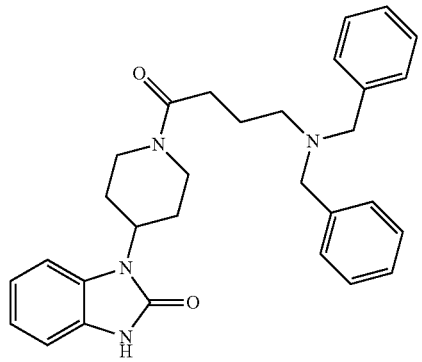

This compound has been obtained from 4-(2-keto-1-benzimidazolinyl)-piperidine and 4-dibenzylaminobutyric acid.

To a solution of 91 mg (0.2 mmol, 1 equiv.) of 4-dienzylaminobutanoic acid in 1 ml of dry dichloromethane at 0° C. were added successively 83 μL (0.6 mmol, 3 eq) of triethylamine, one drop of DMF and 16 μL (0.22 mmol, 1.1 eq) of thionyl chloride. After 30 min., 56 mg (0.26 mmol, 1.3 equiv.) of 4-(2-keto-1-benzimidazolinyl)-piperidine was added. The reaction was allowed to warm to room temperature overnight. The mixture was diluted by dichloromethane, washed by saturated sodium hydrogenocarbonate. The organic layer was dried over sodium sulphate, the solvent evaporated and the residue purified on silica gel.

Colorless oil (20%).

Flash chromatography on silica gel (cyclohexane/ethyl acetate 7/3).

$^1$H NMR (400 MHz, CDCl$_3$, ppm) δ 9.86 (s, 1H, NH), 7.37 (d, J=7.3 Hz, 4H, Ph), 7.31 (t, J=7.4 Hz, 4H, Ph), 7.24 (m, 2H, Ph), 7.09 (m, 4H, Ph), 4.85 (d, J=13.0 Hz, 1H, CHCH$_2$CH$_2$N), 4.53 (tt, J=12.3, 3.8 Hz, 1H, CHCH$_2$CH$_2$N), 3.94 (d, J=13.1 Hz, 1H, CHCH$_2$CH$_2$N), 3.61 (s, 4H, NCH$_2$Ph), 3.12 (t, J=12.5 Hz, 1H, CHCH$_2$CH$_2$N), 2.63 (t, J=12.5 Hz, 1H, CHCH$_2$CH$_2$N), 2.52 (m, 2H, COCH$_2$CH$_2$CH$_2$N), 2.32 (m, 4H, COCH$_2$CH$_2$CH$_2$N, CHCH$_2$CH$_2$N), 1.89 (m, 4H, COCH$_2$CH$_2$CH$_2$N, CHCH$_2$CH$_2$N).

$^{13}$C NMR (100 MHz, CDCl$_3$, ppm) δ 171.4, 154.8 (C=O), 128.8, 128.1, 127.9, 126.9, 121.4, 121.2, 109.8, 109.2 (C$_{Ph}$), 58.4 (NCH$_2$Ph), 52.8 (COCH$_2$CH$_2$CH$_2$N), 50.7 (CHCH$_2$CH$_2$N), 41.3 (CHCH$_2$CH$_2$N), 31.1 (COCH$_2$CH$_2$CH$_2$N), 29.8 (CHCH$_2$CH$_2$N), 22.6 (COCH$_2$CH$_2$CH$_2$N).

LC/MS (ES$^+$) m/z 483.3 (M+H)$^+$

Preparation of 2-Thiobenzimidazolone

Preparation of (S)-2-(dibenzylamino)propyl 4-(1,2-dihydro-2-thioxobenzo[d]imidazol-3-yl)piperidine-1-carboxylate (Compound no 25)

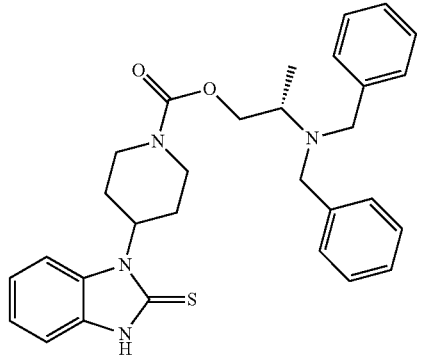

To a solution of 147 mg (0.295 mmol, 1 equiv.) (S)-2-(dibenzylamino)propyl 4-(1,2-dihydro-2-oxobenzo[d]imidazol-3-yl)piperidine-1-carboxylate in 3 ml of toluene was added 89 mg (0.221 mmol, 0.221 equiv.) of Lawesson reagent. The suspension was refluxed overnight. The solid was filtered and the solvent evaporated in vacuum. The residue was purified on silica gel.

Colorless oil (20%).

Preparative TLC (silica gel).

$^1$H NMR (400 MHz, CDCl$_3$, ppm) δ 11.20 (s, 1H, NH), 7.39 (d, J=7.3 Hz, 4H, Ph), 7.28 (t, J=7.4 Hz, 6H, Ph), 7.21 (t, J=7.3 Hz, 3H, Ph), 7.15 (t, J=7.6 Hz, 1H, Ph), 5.46 (m, 1H, CHCH$_2$CH$_2$N), 4.45 (m, 1H), 4.30 (dd, J=10.9, 7.6 Hz, 1H, OCH$_2$), 4.10 (dd, J=12.2, 6.4 Hz, 1H, OCH$_2$), 3.78 (d, J=13.9 Hz, 2H, NCH$_2$Ph), 3.57 (d, J=13.9 Hz, 2H, NCH$_2$Ph), 3.17 (sext., J=6.8 Hz, 1H, CHCH$_3$), 3.02 (m, 2H, CHCH$_2$CH$_2$N), 2.37 (dd, J=12.3, 3.6 Hz, 2H, CHCH$_2$CH$_2$N), 1.96 (d, J=8.1 Hz, 2H, CHCH$_2$CH$_2$N), 1.12 (d, J=6.8 Hz, 3H, CHCH$_3$).

LC/MS (ES$^+$) m/z 515.1 (M+H)$^+$

Amide Preparation

Preparation of N—((S)-2-(dibenzylamino)propyl)-4-(1,2-dihydro-2-oxobenzo[d]imidazol-3-yl)cyclohexanecarboxamide (Compound no 26)

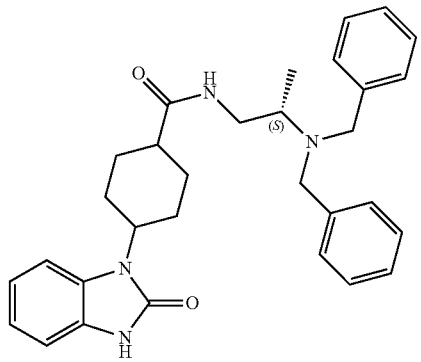

To a stirred solution of (S)—N,N-dibenzylpropane-1,2-diamine (50 mg, 0.20 mmol) in CH$_2$Cl$_2$ (0.5 mL) under N$_2$ was added AlMe₃ (2M in hexane, 100 μL, 0.20 mmol). The reaction mixture was stirred for 30 min at room temperature and a solution of the ester (29 mg, 0.10 mmol) in CH₂Cl₂ (0.6 mL) was added. The mixture was stirred overnight at room temperature and the solvent was removed on vacuo. The crude material was purified by flash chromatography (silica gel, cyclohexane/ethyl acetate 3/7) to afford a pale yellow solid (5 mg, 10%).

¹H NMR (400 MHz, CDCl₃) δ 10.3 (bs, 1H, NH), 7.35 (d, J=7.2 Hz, 4H, Ar), 7.29 (m, 6H, Ar), 7.08 (m, 4H, Ar), 6.05 (s, 1H, NH), 4.23 (m, 1H, NCHCH₂CH₂), 3.79 (d, J=13.2 Hz, 2H, NCH₂Ph), 3.39 (m, 1H, CH₂NH), 3.35 (d, J=13.2 Hz, 2H, NCH₂Ph), 2.96 (m, 1H, CHMe), 2.86 (m, 1H, CH₂NH), 2.27 (m, 2H, NCHCH₂CH₂), 1.98 (m, 3H, CHCO, NCHCH₂CH₂), 1.59 (m, 4H, NCHCH₂CH₂), 1.09 (d, J=6.4 Hz, 3H, Me).

¹³C NMR (100 MHz, CDCl₃) δ 174.0 (C=O$_{Amide}$), 154.4 (C=O), 139.7 (C$_{Ar}$), 128.9 (CH$_{Ar}$), 128.5 (CH$_{Ar}$), 127.6 (C$_{Ar}$), 127.2 (CH$_{Ar}$), 121.2 (CH$_{Ar}$), 121.1 (CH$_{Ar}$), 109.3 (CH$_{Ar}$), 108.9 (CH$_{Ar}$), 53.1 (NCH₂Ph), 52.4 (CHMe), 52.1 (NCHCH₂CH₂), 44.4 (CHCO), 41.6 (CH₂NH), 29.7 (NCHCH₂CH₂), 29.0 (NCHCH₂CH₂), 9.9 (Me).

LC/MS (ES⁺) m/z 497.3 (M+H)⁺

Benzene Derivative Preparation 1-(prop-1-en-2-yl)-1H-benzo[d]imidazol-2(3H)-one (Intermediate)

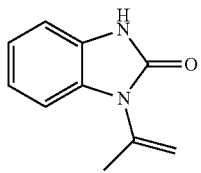

A solution of benzene-1,2-diamine (1.0 g, 9.26 mmol) in ethyl acetoacetate (1.18 mL, 9.26 mol) was heated at 150° C. for 1 h. The solvent was removed on vacuo and the residue was purified by flash chromatography on silica gel (cyclohexane/ethyl acetate 6/4) to afford a yellow solid (290 mg, 18%).

¹H NMR (400 MHz, CDCl₃) δ 7.09 (m, 4H, Ar), 5.41 (s, 1H, H₂C=C), 5.25 (s, 1H, H₂C=C), 2.25 (s, 3H, C=CCH₃).

LC/MS (ES⁺) m/z 175.1 (M+H)⁺

1-(4-aminophenyl)-3-(prop-1-en-2-yl)-1H-benzo[d]imidazol-2(3H)-one (Intermediate)

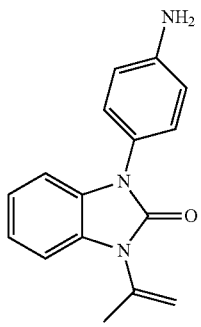 [SMILES: C=C(C)n1c(=O)n(-c2ccc(N)cc2)c2ccccc21]

To a stirred solution of isopropylidene protected benzimidazolone derivative (80 mg, 0.46 mmol) in dimethylsulfoxide (DMSO) (0.6 mL) under N₂ was added K₂CO₃ (32 mg, 0.23 mmol). The reaction mixture was heated at 80° C. for 20 min and 1-fluoro-4-nitrobenzene (49 μL, 0.46 mmol) was added. The mixture was heated at 80° C. overnight. K₂CO₃ (12 mg, 0.10 mmol) and 1-fluoro-4-nitrobenzene (16 μL, 0.15 mmol) were added and the solution was heated at 80° C. for 48 h. Water (10 mL) was introduced and the mixture was extracted with ethyl acetate (3×15 mL). The combined organic layers were dried over anhydrous Na₂SO₄, filtered and concentrated under vacuum. To a stirred solution of the crude material in MeOH (7 mL) under N₂ were added HOAc (3 drops), decaborane (17 mg, 0.14 mmol) and 10% Pd/C (20 mg). The reaction mixture was refluxed for 3 h. The reaction mixture was filtered through a pad of Celite. The filtrate was concentrated under vacuo and the residue was purified by flash chromatography on silica gel (cyclohexane/ethyl acetate 5/5) to afford a yellow oil (86 mg, 71%).

LC/MS (ES⁺) m/z 266.10 (M+H)⁺

(S)-2-(dibenzylamino)propyl 4-(1,2-dihydro-2-oxo-1-(prop-1-en-2-yl)benzo[d]imidazol-3-yl)phenylcarbamate (Intermediate)

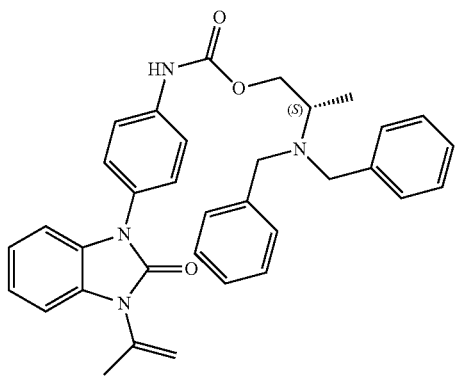

To a stirred solution of the (S)-2-(dibenzylamino)propan-1-ol (32 mg, 0.12 mmol) in CH₂Cl₂ (0.8 mL) was added dimethylaminopyridine (DMAP) (76 mg, 0.62 mmol) under a nitrogen atmosphere. The reaction mixture was cooled to −78° C. and triphosgene (12 mg, 0.04 mmol) was added. The solution was stirred for 1 h at −78° C. and a solution of the aniline derivative (33 mg, 0.12 mmol) in CH₂Cl₂ (0.3 mL) was added dropwise. The reaction mixture was stirred for 2 h at room temperature. A saturated aqueous NaHCO₃ solution (3 mL) was introduced and the mixture was extracted with ethyl acetate (3×5 mL). The combined organic layers were dried over anhydrous Na₂SO₄, filtered and concentrated under vacuum. The crude material was purified by flash chromatography (silica gel, cyclohexane/ethyl acetate 8/2) to afford a white solid (17 mg, 25%).

¹H NMR (400 MHz, CDCl₃) δ 7.52 (d, J=8.4 Hz, 2H, Ar), 7.45 (d, J=8.4 Hz, 2H, Ar), 7.39 (d, J=7.2 Hz, 4H, Bn), 7.29 (t, J=7.2 Hz, 4H, Bn), 7.21 (t, J=7.2 Hz, 2H, Bn), 7.12-7.05 (m, 4H, Ar), 6.94 (s, 1H, NH), 5.39 (s, 1H, H₂C=C), 5.27 (s, 1H, H₂C=C), 4.34 (dd, J=11.0, 7.2 Hz, 1H, CH₂O), 4.12 (dd, J=11.0, 6.0 Hz, 1H, CH₂O), 3.77 (d, J=14.0 Hz, 2H, NCH₂Ph), 3.58 (d, J=14.0 Hz, 2H, NCH₂Ph), 3.14 (m, 1H, CHMe), 2.27 (s, 3H, C=CCH₃), 1.12 (d, J=6.8 Hz, 3H, CHCH₃).

¹³C NMR (100 MHz, CDCl₃) δ 153.4 (C=O), 152.0 (C=O), 140.1, 137.9, 137.5, 129.9, 129.3, 128.9, 128.6, 128.1, 126.9, 126.8, 121.9, 121.7, 119.5, 119.4, 113.5, 109.1, 108.7, 66.7 (CH$_2$O), 53.8 (NCH$_2$Ph), 52.0 (CHMe), 20.1 (C=CCH$_3$), 11.3 (CHCH$_3$).

LC/MS (ES$^+$) m/z 547.2 (M+H)$^+$

Preparation of 2-(dibenzylamino)propyl 4-(1,2-dihydro-2-oxobenzo[d]imidazol-3-yl)phenylcarbamate (Compound no 27)

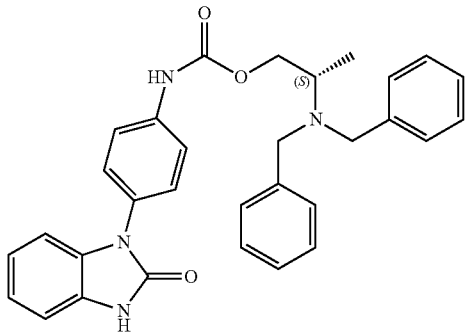

(27)

A stirred solution of the carbamate derivative as above obtained (30 mg, 0.06 mmol) in MeOH/conc. HCl 9:1 (1.5 mL) was heated at 75° C. for 1 h. A saturated aqueous NaHCO$_3$ solution was introduced to pH 8 and the mixture was extracted with ethyl acetate (3×5 mL). The combined organic layers were dried over anhydrous Na$_2$SO$_4$, filtered and concentrated under vacuum. The crude material was purified by flash chromatography (silica gel, cyclohexane/ethyl acetate 5/5) to afford a white solid (15 mg, 54%).

$^1$H NMR (400 MHz, CDCl$_3$) δ 7.57 (d, J=8.4 Hz, 2H, Ar), 7.49 (d, J=8.4 Hz, 2H, Ar), 7.39 (d, J=7.2 Hz, 4H, Bn), 7.30 (t, J=7.2 Hz, 4H, Bn), 7.22 (t, J=7.2 Hz, 2H, Bn), 7.12 (m, 2H, Ar), 7.08 (m, 1H, Ar), 7.03 (m, 1H, Ar), 6.82 (s, 1H, NH), 4.36 (dd, J=11.0, 7.2 Hz, 1H, CH$_2$O), 4.11 (dd, J=11.0, 6.0 Hz, 1H, CH$_2$O), 3.78 (d, J=14.0 Hz, 2H, NCH$_2$Ph), 3.58 (d, J=14.0 Hz, 2H, NCH$_2$Ph), 3.15 (m, 1H, CHMe), 1.13 (d, J=6.8 Hz, 3H, Me).

$^{13}$C NMR (100 MHz, CDCl$_3$) δ 154.7 (C=O), 153.3 (C=O), 140.1, 137.6, 130.7, 129.3, 128.6, 128.2, 127.7, 127.0, 126.8, 122.2, 121.6, 119.5, 109.7, 108.8, 66.8 (CH$_2$O), 53.8 (NCH$_2$Ph), 52.1 (CHMe), 11.2 (Me).

LC/MS (ES$^+$) m/z 507.2 (M+H)$^+$

"Amine Preparation"

2-((S)-2-(dibenzylamino)propyl)isoindoline-1,3-dione (Intermediate)

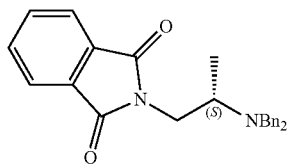

To a stirred suspension of phtalimide (824 mg, 5.60 mmol), (S)-2-(dibenzylamino)propan-1-ol (1.02 g, 4.00 mmol) and PPh$_3$ (1.47 g, 5.60 mmol) in THF (30 mL) cooled to 0° C. under N$_2$ was added dropwise DEAD (1.2 mL, 7.60 mmol). The resulting mixture was allowed to warm to room temperature and stirred overnight. The solvent was evaporated. The residue was purified by flash chromatography (silica gel, cyclohexane/methylene chloride 5/5) to afford a white solid (1.08 g, 70%).

$^1$H NMR (400 MHz, CDCl$_3$) δ 7.81 (dd, J=5.6, 2.8 Hz, 2H, Ar), 7.74 (dd, J=5.6, 3.2 Hz, 2H, Ar), 7.20 (m, 4H, Ar), 7.11 (m, 6H, Ar), 4.00 (dd, J=14.0, 9.2 Hz, 1H, CH$_2$N), 3.81 (d, J=13.6 Hz, 2H, NCH$_2$Ph), 3.38 (m, 3H, CH$_2$N, NCH$_2$Ph), 3.23 (m, 1H, CHMe), 1.13 (d, J=6.8 Hz, 3H, Me).

LC/MS (ES$^+$) m/z 385.3 (M+H)$^+$ (S)—N,N-dibenzylpropane-1,2-diamine (Intermediate)

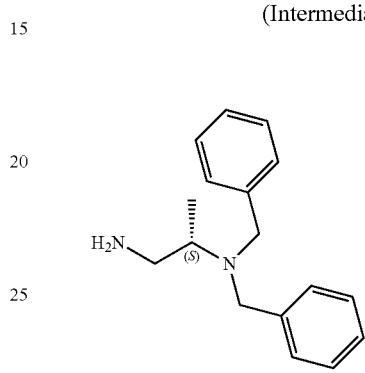

To a stirred solution of the phtalimide derivative (1.08 g, 2.80 mmol) in ethanol (30 mL) was added hydrazine monohydrate (354 µL, 7.30 mmol) under N$_2$ atmosphere. The reaction mixture was refluxed for 3 h at room temperature. The residue was filtered and washed with ethanol. The filtrate was concentrated under vacuo and the crude material was purified by flash chromatography (silica gel, methylene chloride/ethanol/NEt$_3$ 89/10/1) to afford a colorless oil (700 mg, 98%).

$^1$H NMR (400 MHz, CDCl$_3$) δ 7.32 (m, 8H, Ar), 7.23 (m, 2H, Ar), 3.77 (d, J=13.6 Hz, 2H, NCH$_2$Ph), 3.37 (d, J=13.6 Hz, 2H, NCH$_2$Ph), 2.73 (m, 2H, CH$_2$N), 2.47 (m, 1H, CHMe), 0.98 (d, J=6.4 Hz, 3H, Me).

LC/MS (ES$^+$) m/z 255.1 (M+H)$^+$

Preparation of aminoalcohol by dibenzylation

2-Dibenzylamino-ethanol (Intermediate)

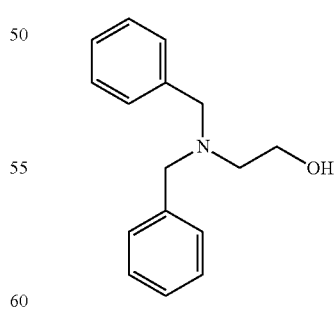

To a vigorously stirred solution of 6.7 ml (1.12 mol, 1 equiv.) ethanolamine in 120 ml of (1/1) MeOH/H$_2$O were added 7.2 g (1.8 mol, 1.6 equiv.) of sodium hydroxide and 24.6 g (1.8 mol., 1.6 eq). The suspension was refluxed for 30' before addition of 24.5 ml (2.3 mol., 2 equiv.) of benzyl chloride. The mixture was refluxed overnight before cooled to room temperature and extracted with 3×160 ml of diethyl ether. The organic solution was dried over sodium sulphate, and evaporated. The residue was distilled Kugel Rohr (100° C., 1 mm Hg).

Colorless oil (54%).

$^1$H NMR (400 MHz, CDCl$_3$) δ 7.30 (m, 10H, Ph), 3.68 (s, 4H, NCH$_2$Ph), 3.60 (t, J=5.4 Hz, 2H, OCH$_2$CH$_2$N), 2.68 (t, J=5.4 Hz, 2H, OCH$_2$CH$_2$N), 2.36 (s$_b$, 1H, OH).

LC/MS (ES$^+$) m/z 242.1 (M+H)$^+$

Preparation of aminoacide by Hydrolysis of Corresponding ester 4-dibenzylamino-butyric acid (Intermediate)

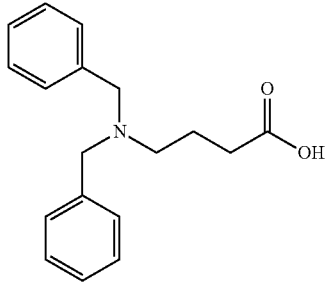 [SMILES: O=C(O)CCCN(Cc1ccccc1)Cc1ccccc1]

To a solution of 500 mg (1.6 mmol, 1 equiv.) of 4-dibenzylamino-butyric acid ethyl ester in 1 ml of THF was added 4 ml of HCl 2N and the resulting mixture was stirred for 48 hours. After decantation and separation, the aqueous layer was extracted twice by ethyl acetate. The pH was fixed to 5 using solid sodium carbonate and the aqueous layer was extracted by dichloromethane. The dichloromethane layer was dried over sodium sulphate, evaporated and used without further purification.

Yellow oil (40%)

$^1$H NMR (400 MHz, CDCl$_3$) δ 12.00 (s$_b$, 1H, COOH), 7.30 (m, 10H, Ph), 3.75 (s, 4H, NCH$_2$Ph), 2.67 (t, J=6.0 Hz, 2H, NCH$_2$CH$_2$CH$_2$COOH), 2.25 (t, J=6.5 Hz, 2H, NCH$_2$CH$_2$CH$_2$COOH), 1.80 (m, 2H, NCH$_2$CH$_2$CH$_2$COOH).

LC/MS (ES$^+$) m/z 284.1 (M+H)$^+$

Preparation of 4-hydroxypiperidine

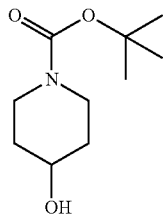

To a stirred solution of 2.5 g (12.5 mmol, 1 equiv.) of N-tert-butyloxycarbonyl-4-piperidone in 25 ml of methyl alcohol was added 946 mg (25 mmol, 2 eq) of sodium borohydride at 0° C. The reaction was pursued at 0° C. for 2 hours and for 2 hours at room temperature. The mixture was diluted by water and brine and extracted by ethyl acetate. The organic layer was dried over sodium sulphate and the solvent was evaporated in vacuum. The residue was used without further purification.

White solid (100%)

$^1$H NMR (400 MHz, CDCl$_3$) δ 3.80 (m, 3H, NCH$_2$CH$_2$CH), 3.03 (t, J=10.4 Hz, 2H, NCH$_2$CH$_2$CH), 3.75 (s, 4H, NCH$_2$Ph), 2.67 (t, J=6.0 Hz, 2H, NCH$_2$CH$_2$CH$_2$COOH), 2.25 (t, J=6.5 Hz, 2H, NCH$_2$CH$_2$CH$_2$COOH), 1.80 (m, 2H, NCH$_2$CH$_2$CH$_2$COOH).

LC/MS (ES$^+$) m/z 284.1 (M+H)$^+$

"One Pot Procedure": Perbenzylation, Reduction of Corresponding ester and CDI Coupling:

To a stirred solution of the appropriate aminoacid (1 equiv.) in MeOH (2 mL/mmol) were added BnBr (2.2 equiv.) and K$_2$CO$_3$ (2.5 equiv.) under N$_2$ atmosphere. The reaction mixture was stirred for 16 h at room temperature and the solvent was removed on vacuo. H$_2$O (2 mL/mmol) was added and the aqueous phase was extracted with dichloromethane (3×5 mL/mmol). The combined organic layers were dried (Na$_2$SO$_4$), filtered and concentrated on vacuo. To the crude material (1.5 equiv.) in THF (2 mL/mmol) at 0° C. was added LiAlH$_4$ (2 equiv.) and the reaction mixture was stirred for 16 h at room temperature. Successively water (40 μL/mmol LiAlH$_4$), aqueous sodium hydroxide 2N (40 μL/mmol LiAlH$_4$) and water (120 μL/mmol LiAlH$_4$) were added. The precipitated was filtered off and washed with ethyl acetate. The filtrate was dried over sodium sulphate, evaporated. To a stirred solution of the residue in THF (2 mL/mmol) at 0° C. was added CDI (1.1 equiv.) under N$_2$ atmosphere. The reaction mixture was stirred for 2 h at room temperature. The appropriate amine (1.5 equiv.) in THF (10 mL/mmol) was added and the reaction mixture was stirred for 72 h at room temperature. The solvent was removed on vacuo and the residue was purified by flash chromatography on silica gel.

(Ref: J. Org. Chem., 1996, 3635-45; J. Org. Chem., 2003, 613-16)

Preparation of (S)-2-(dibenzylamino)-4-methylpentyl 4-(1,2-dihydro-2-oxobenzo[d]imidazol-3-yl)piperidine-1-carboxylate (Compound no 91)

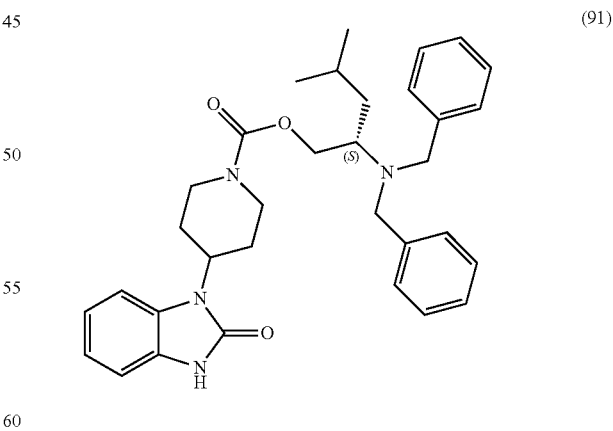

From 4-(2-keto-1-benzimidazolinyl)-piperidine and (S)-2-amino-4-methylpentanoic acid White solid (48%).

Flash chromatography on silica gel (dichloromethane/methanol 95/5)

$^1$H NMR (400 MHz, CDCl$_3$) δ 10.26 (s, 1H, NH), 7.39 (d, J=7.2 Hz, 4H, Ph), 7.28 (t, J=7.6 Hz, 4H, Ph), 7.21 (t, J=7.3,

2H, Ph), 7.14 (m, 2H, Ph), 7.07 (m, 2H, Ph), 4.55 (m, 1H, CHCH$_2$CH$_2$N), 4.35 (m, 2H, CHCH$_2$CH$_2$N), 4.31 (dd, J=11.2, 6.8 Hz, 1H, CH$_2$O), 4.08 (m, 1H, CH$_2$O), 3.73 (d, J=13.6 Hz, 2H, NCH$_2$Ph), 3.66 (d, J=13.6 Hz, 2H, NCH$_2$Ph), 2.99 (m, 3H, CHCH$_2$CH$_2$N, CHCH$_2$iPr), 2.40 (m, 2H, CHCH$_2$CH$_2$N), 1.91 (m, 2H, CHCH$_2$CH$_2$N), 1.77 (m, 1H, CH(CH$_3$)$_2$), 1.56 (m, 1H, CH$_2$CH(CH$_3$)$_2$), 1.19 (m, 1H, CH$_2$CH(CH$_3$)$_2$), 0.88 (d, J=6.8 Hz, 3H, CHCH$_3$), 0.70 (d, J=6.8 Hz, 3H, CHCH$_3$).

$^{13}$C NMR (100 MHz, CDCl$_3$) δ 155.3 (C=O), 155.2 (C=O), 140.2, 128.8, 128.1, 128.0, 126.8, 121.4, 121.1, 109.9, 109.3, 66.8 (CH$_2$O), 54.1 (NCH$_2$Ph), 53.9 (CHiPr), 50.7 (CHCH$_2$CH$_2$N), 43.3 (CHCH$_2$CH$_2$N), 30.8 (CH(CH$_3$)$_2$), 29.2 (CHCH$_2$CH$_2$N), 24.9 (CH$_2$CH(CH$_3$)$_2$), 23.0 (2×CHCH$_3$).

LC/MS (ES$^+$) m/z 541.3 (M+H)$^+$

Preparation of (S)-2-(dibenzylamino)-3-methylbutyl 4-(1,2-dihydro-2-oxobenzo[d]imidazol-3-yl)piperidine-1-carboxylate (Compound no 29)

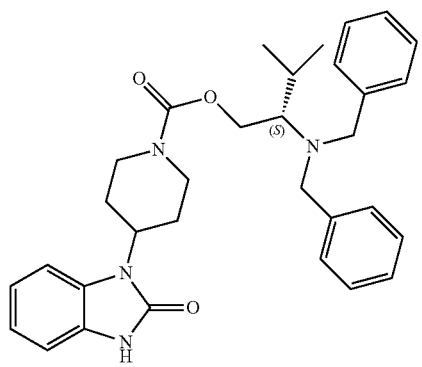

(29)

From 4-(2-keto-1-benzimidazolinyl)-piperidine and (S)-2-amino-3-methylbutanoic acid Colorless oil (27%).

Flash chromatography on silica gel (dichloromethane/methanol 95/5)

$^1$H NMR (400 MHz, CDCl$_3$) δ 9.85 (s, 1H, NH), 7.37 (d, J=7.6 Hz, 4H, Ph), 7.28 (t, J=7.6 Hz, 4H, Ph), 7.21 (t, J=7.3 Hz, 2H, Ph), 7.14 (m, 4H, Ph), 4.54 (m, 3H, CHCH$_2$CH$_2$N, CHCH$_2$CH$_2$N), 4.31 (m, 2H, CH$_2$O), 3.93 (d, J=14.0 Hz, 2H, NCH$_2$Ph), 3.56 (d, J=14.0 Hz, 2H, NCH$_2$Ph), 2.99 (m, 2H, CHCH$_2$CH$_2$N), 2.48 (m, 1H, CHiPr), 2.43 (m, 2H, CHCH$_2$CH$_2$N), 2.05 (m, CH(Me)$_3$), 1.89 (m, 2H, CHCH$_2$CH$_2$N), 1.06 (d, J=6.8 Hz, 3H, CHCH$_3$), 0.92 (d, J=6.4 Hz, 3H, CHCH$_3$).

$^{13}$C NMR (100 MHz, CDCl$_3$) δ 155.2 (C=O), 154.7 (C=O), 140.1, 128.8, 128.1, 127.8, 126.8, 121.4, 121.2, 109.8, 109.2, 62.6 (CH$_2$O), 62.1 (CHiPr), 54.6 (NCH$_2$Ph), 50.6 (CHCH$_2$CH$_2$N), 43.7 (CHCH$_2$CH$_2$N), 29.2 (CHCH$_2$CH$_2$N), 27.8 (CH(CH$_3$)$_2$), 21.2 (CHCH$_3$), 20.3 (2×CHCH$_3$).

LC/MS (ES$^+$) m/z 527.2 (M+H)$^+$

Preparation of (S)-2-(dibenzylamino)-2-phenylethyl 4-(1,2-dihydro-2-oxobenzo[d]imidazol-3-yl)piperidine-1-carboxylate (Compound no 34)

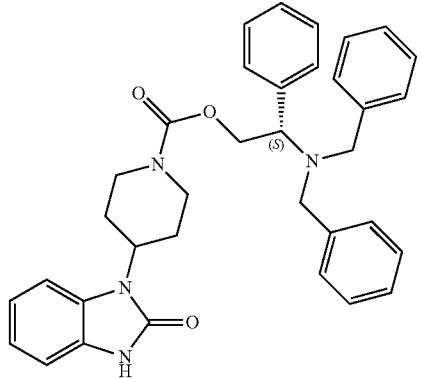

(34)

From 4-(2-keto-1-benzimidazolinyl)-piperidine and (S)-2-amino-2-phenylacetic acid Colorless oil (21%).

Flash chromatography on silica gel (dichloromethane/methanol 95/5)

$^1$H NMR (400 MHz, CDCl$_3$) δ 9.93 (s, 1H, NH), 7.41 (d, J=7.2 Hz, 6H, Ph), 7.30 (t, J=7.6 Hz, 6H, Ph), 7.21 (m, 3H, Ph), 7.10 (m, 2H, Ph), 7.05 (m, 2H, Ph), 4.78 (m, 1H, CHCH$_2$CH$_2$N), 4.50 (m, 3H, CH$_2$O, CHCH$_2$CH$_2$N), 4.13 (m, 1H, CH$_2$O), 3.88 (d, J=14.0 Hz, 2H, NCH$_2$Ph), 3.36 (d, J=14.0 Hz, 2H, NCH$_2$Ph), 2.91 (m, 2H, CHCH$_2$CH$_2$N), 2.33 (m, 1H, CHPh), 1.85 (m, 2H, CHCH$_2$CH$_2$N), 1.66 (m, 2H, CHCH$_2$CH$_2$N).

$^{13}$C NMR (100 MHz, CDCl$_3$) δ 155.0 (C=O), 154.9 (C=O), 139.8, 136.6, 128.8, 128.7, 128.2, 128.1, 127.9, 127.5, 126.9, 121.4, 121.2, 114.9, 109.8, 109.3, 64.1 (CH$_2$O), 60.6 (CHPh), 54.0 (NCH$_2$Ph), 50.6 (CHCH$_2$CH$_2$N), 43.6 (CHCH$_2$CH$_2$N), 29.1 (CHCH$_2$CH$_2$N).

LC/MS (ES$^+$) m/z 561.2 (M+H)$^+$

Preparation of 2-(dibenzylamino)-2-methylpropyl 4-(1,2-dihydro-2-oxobenzo[d]imidazol-3-yl)piperidine-1-carboxylate (Compound no 33)

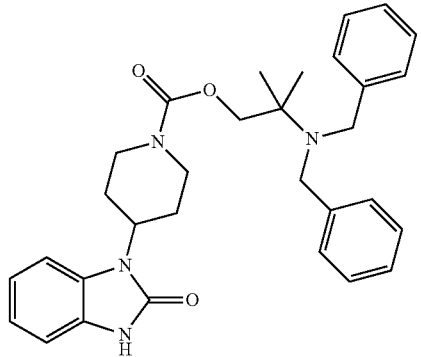

(33)

From 4-(2-keto-1-benzimidazolinyl)-piperidine and 2-amino-2-methylpropanoic acid White solid (34%).

Flash chromatography on silica gel (dichloromethane/methanol 95/5)

$^1$H NMR (400 MHz, CDCl$_3$,) δ 9.25 (s, 1H, NH), 7.30 (d, J=7.2 Hz, 4H, Ph), 7.17 (t, J=7.2 Hz, 4H, Ph), 7.05 (m, 6H, Ph), 4.54 (m, 1H, CHCH$_2$CH$_2$N), 4.40 (m, 2H, CHCH$_2$CH$_2$N), 4.17 (s, 2H, CH$_2$O), 3.82 (s, 4H, NCH$_2$Ph), 2.97 (m, 2H, CHCH$_2$CH$_2$N), 2.37 (m, 2H, CHCH$_2$CH$_2$N), 1.89 (m, 2H, CHCH$_2$CH$_2$N), 1.18 (s, 6H, Me).

$^{13}$C NMR (100 MHz, CDCl$_3$) δ 155.2 (C=O), 154.5 (C=O), 142.0, 129.1, 128.2, 127.8, 127.7, 126.3, 121.4, 121.3, 109.6, 109.3, 70.8 (CH$_2$O), 58.1 (C(Me)$_2$), 54.1 (NCH$_2$Ph), 50.6 (CHCH$_2$CH$_2$N), 43.6 (CHCH$_2$CH$_2$N), 29.5 (CHCH$_2$CH$_2$N), 23.2 (Me).

LC/MS (ES$^+$) m/z 513.2 (M+H)$^+$

Preparation of 3-(dibenzylamino)butyl 4-(1,2-dihydro-2-oxobenzo[d]imidazol-3-yl)piperidine-1-carboxylate (Compound no 32)

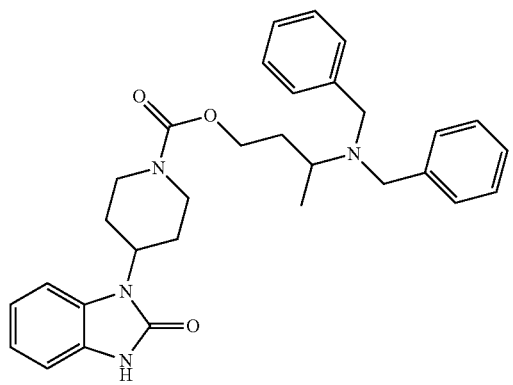

(32)

From 4-(2-keto-1-benzimidazolinyl)-piperidine and 3-aminobutanoic acid.

Colorless oil (82%).

Flash chromatography on silica gel (dichloromethane/methanol 95/5).

$^1$H NMR (400 MHz, CDCl$_3$) δ 9.65 (s, 1H, NH), 7.30 (d, J=7.6 Hz, 4H, Ph), 7.17 (t, J=7.2 Hz, 4H, Ph), 7.05 (t, J=7.2 Hz, 2H, Ph), 7.14-7.06 (m, 4H, Ph), 4.48-4.24 (m, 5H, CHCH$_2$CH$_2$N, CH$_2$O, CHCH$_2$CH$_2$N), 3.74 (d, J=13.6 Hz, 2H, NCH$_2$Ph), 3.40 (d, J=13.6 Hz, 2H, NCH$_2$Ph), 2.92 (m, 1H, CH$_2$CHMe), 2.78 (m, 2H, CHCH$_2$CH$_2$N), 2.28 (m, 2H, CHCH$_2$CH$_2$N), 1.93 (m, 1H, CH$_2$CHMe), 1.83 (m, 2H, CHCH$_2$CH$_2$N), 1.65 (m, 1H, CH$_2$CHMe), 1.18 (d, J=6.8 Hz, 3H, Me).

$^{13}$C NMR (100 MHz, CDCl$_3$) δ 155.3 (C=O), 155.2 (C=O), 140.3, 128.6, 128.5, 128.1, 128.0, 126.7, 121.4, 121.1, 109.6, 109.4, 63.2 (CH$_2$O), 53.4 (CH$_2$CHMe), 53.2 (NCH$_2$Ph), 50.6 (CHCH$_2$CH$_2$N), 43.3 (CHCH$_2$CH$_2$N), 33.3 (CH$_2$CHMe), 26.9 (CHCH$_2$CH$_2$N), 12.9 (Me).

LC/MS (ES$^+$) m/z 513.2 (M+H)$^+$

Preparation of 2-(dibenzylamino)-3,3-dimethylbutyl 4-(1,2-dihydro-2-oxobenzo[d]imidazol-3-yl)piperidine-1-carboxylate (Compound no 31)

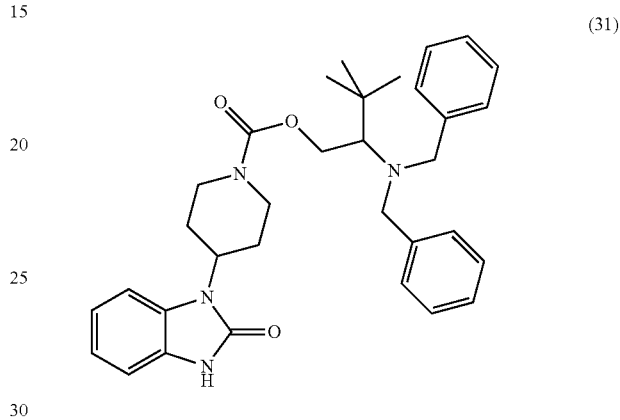

(31)

From 4-(2-keto-1-benzimidazolinyl)-piperidine and 2-amino-3,3-dimethylbutanoic acid White solid (27%).

Flash chromatography on silica gel (dichloromethane/methanol 95/5)

$^1$H NMR (400 MHz, CDCl$_3$) δ 8.74 (s, 1H, NH), 7.38 (d, J=6.8 Hz, 4H, Ph), 7.31 (t, J=7.2 Hz, 4H, Ph), 7.18 (m, 2H, Ph), 7.07 (m, 4H, Ph), 4.54 (m, 3H, CHCH$_2$CH$_2$N, CHCH$_2$CH$_2$N), 4.40-4.17 (bs, 2H, CH$_2$O), 3.95 (d, J=12.8 Hz, 2H, NCH$_2$Ph), 3.63 (d, J=13.6 Hz, 2H, NCH$_2$Ph), 3.02 (m, 2H, CHCH$_2$CH$_2$N), 2.80 (m, 1H, CHtBu), 2.37 (m, 2H, CHCH$_2$CH$_2$N), 1.89 (m, 2H, CHCH$_2$CH$_2$N), 0.87 (s, 9H, tBu).

LC/MS (ES$^+$) m/z 541.3 (M+H)$^+$

"One Pot Procedure": Reductive Amination with benzaldehyde and CDI Coupling:

To a stirred solution of the appropriate aminoalcohol (1 equiv.) dichloroethane (1 mL/mmol) were added benzaldehyde (2 equiv.) and NaBH(OAc)$_3$ (2 equiv.) under N$_2$ atmosphere. The reaction mixture was stirred for 48 h at room temperature and the solvent was removed on vacuo. Saturated aqueous NaHCO$_3$ solution (2 mL/mmol) was added and the aqueous phase was extracted with ethyl acetate (3×5 mL/mmol). The combined organic layers were dried (Na$_2$SO$_4$), filtered and concentrated on vacuo. To a stirred solution of the residue in THF (2 mL/mmol) at 0° C. was added CDI (1.1 equiv.) under N$_2$ atmosphere. The reaction mixture was stirred for 2 h at room temperature. The appropriate amine (1.5 equiv.) in THF (10 mL/mmol) was added and the reaction mixture was stirred for 72 h at room temperature. The solvent was removed on vacuo and the residue was purified by flash chromatography on silica gel.

Preparation of 2-(N-benzyl-N-phenylamino)ethyl 4-(1,2-dihydro-2-oxobenzo[d]imidazol-3-yl)piperidine-1-carboxylate (Compound no 35)

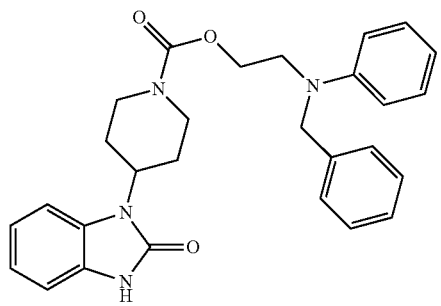

(35)

From 4-(2-keto-1-benzimidazolinyl)-piperidine and 2-(phenylamino)ethanol

Pale green solid (68%).

Flash chromatography on silica gel (dichloromethane/methanol 95/5)

$^1$H NMR (400 MHz, CDCl$_3$) δ 9.84 (s, 1H, NH), 7.39 (d, J=6.8 Hz, 2H, Ph), 7.26 (m, 3H, Ph), 7.20 (t, J=7.6 Hz, 2H, Ph), 7.13-7.04 (m, 4H, Ph), 7.07 (d, J=8.0 Hz, 2H, Ph), 7.07 (t, J=7.2 Hz, 1H, Ph), 4.64 (s, 2H, NCH$_2$Ph), 4.46 (m, 3H, CHCH$_2$CH$_2$N, CHCH$_2$CH$_2$N), 4.38 (t, J=6.0 Hz, 2H, CH$_2$O), 3.77 (t, J=6.0 Hz, 2H, CH$_2$N(Ph)Bn), 2.85 (m, 2H, CHCH$_2$CH$_2$N), 2.32 (m, 2H, CHCH$_2$CH$_2$N), 1.65 (m, 2H, CHCH$_2$CH$_2$N).

$^{13}$C NMR (100 MHz, CDCl$_3$) δ 152.3 (C=O), 152.1 (C=O), 146.7, 136.2, 126.5, 126.1, 125.9, 125.2, 124.1, 123.8, 118.7, 118.5, 114.1, 109.7, 107.1, 106.7, 60.1 (CH$_2$O), 51.9 (CH$_2$N(Ph)Bn), 47.8 (NCH$_2$Ph), 47.3 (CHCH$_2$CH$_2$N), 40.8 (CHCH$_2$CH$_2$N), 26.4 (CHCH$_2$CH$_2$N).

LC/MS (ES$^+$) m/z 471.2 (M+H)$^+$

Solid Phase Synthesis

Synthesis of N-Benzyl-N-methyl polystyrene

To a suspension of Merrifield resin (3.1 mmol, 1 equiv., 1.97 mmol/g) in 50 ml of dry DMF were successively added 1.4 g (9.4 mmol, 3 equiv.) of sodium iodide, 1 g (4.7 mmol, 1.5 equiv.) of 1,8-bis(dimethylamine)naphtalene and 1.7 ml (15.6 mmol, 5 equiv.) of benzylamine. The suspension was heated for 30 hours at 90° C. The resin was filtered off and washed with hot DMF (2×20 ml), water (2×20 ml), and consecutive wash of methyl alcohol and dichloromethane (4×10 ml). Resin was dried in vacuo after washing with diethyl ether (1×10 ml).

White resin

Loading: 1.36 mmol/g

IR (KBr): υ=3446, 3022, 2922, 2308, 1944, 1872, 1798, 1746, 1720, 1652, 1601, 1509, 1492, 1452, 1360, 1181, 1102, 1022, 964, 903, 820, 738, 695, 522 cm$^{-1}$.

Anal. Calcd N=2.42%. Found N=1.90%

Synthesis of (4-(3-Benzyl-3-methylpolystyryl-1-triazenyl)-phenyl)-methanol

To a solution of 893 mg (7.25 mmol, 5 equiv.) of 4-aminobenzylalcohol, 1.8 ml (14.5 mmol, 10 equiv.) of boron trifluoride diethyl ether complex in 10 ml of dry THF was added 1.7 ml (14.5 mmol, 10 equiv.) of t-butylnitrite at −10° C. The mixture was stirred 1 hour and the diazo suspension was solubilized by addition of 10 ml of a solution of dried DMF/pyridine (1/1). 1 g (1.41 mmol, 1 equiv.) of N-benzyl-N-methyl polystyrene was added and stirred for 1 hour. Resin was filtered off and washed by successively (9/1, v/v) DMF/pyridine (3×10 ml), (9/1, v/v) THF/NEt$_3$ (3×10 ml), (9/1, v/v) MeOH/NEt$_3$ (3×10 ml), MeOH (1×10 ml). This procedure was repeated for optimal loading. Resin was dried in vacuo after washing with diethyl ether (1×10 ml).

Orange resin

Loading: 0.92 mmol/g

IR (KBr): υ=3439, 3052, 3025, 2918, 1943, 1802, 1601, 1493, 1450, 1346, 1143, 1073, 1026, 904, 841, 753, 697, 537 cm$^{-1}$

Anal. Calcd N=5.89%. Found: N=3.85%

Synthesis of (4-(3-Benzyl-3-methylpolystyryl-1-triazenyl)-phenyl)-formaldehyde

To a suspension of 100 mg (0.143 mmol, 1 equiv.) of N-benzyl-N-methyl-N-(4-methanolphenyl)polystyrene in 5 ml of dry dichloromethane was added 112 mg (0.28 mmol, 2 equiv.) of Dess Martin reagent. The resin was shaken overnight, filtered off and washed by CH$_2$Cl$_2$ (4×5 ml) and consecutive wash of methyl alcohol and dichloromethane (4×10 ml). Resin was dried in vacuo after washing with diethyl ether (1×10 ml).

Orange resin.

IR (KBr): υ=3056, 3025, 2918, 2860, 2732, 2339, 1945, 1879, 1800, 1693, 1597, 1492, 1448, 1402, 1338, 1138, 1109, 838, 747, 696, 535 cm$^{-1}$

Typical Procedure for the Preparation of aminoalcohol Resins, First Reductive Amination To a suspension of 100 mg (0.14 mmol, 1 equiv.) of N-benzyl-N-methyl-N-(4-formylphenyl)polystyrene in 2 ml of a solution of dry dichloromethane/acetic acid (2.5% v/v) was added 1.4 mmol (10 equiv.) of appropriate aminoalcohol (typically ethanolamine) and shaken for 2 hours. 424 mg (2 mmol, 15 equiv.) of sodium triacetylborohydride was added and the suspension was shaken overnight. The excess of sodium triacetylborohydride was destroyed by carefully addition of methyl alcohol, resin was filtered off and wash by MeOH (1×5 ml), (9/1) THF/NEt$_3$ (3×5 ml×15 minutes), (1/1) THF/water (2×5 ml) and consecutive wash of methyl alcohol and dichloromethane (4×5 ml). Resin was dried in vacuo after washing with diethyl ether (1×5 ml).

Typical Procedure for the Preparation of aminoalcohol Resins, Second Reductive Amination To a suspension of 100 mg (0.14 mmol, 1 equiv.) of N-alkylaminoalcohol resin in 2 ml of dry trimethyl orthoformate was added 22.5 mg (1.4 mmol, 10 equiv.) of the appropriate aldehyde and the suspension was shaken overnight. The resin was filtered off under N$_2$ atmosphere, washed by dry DMF (2×2 ml), dry THF (2×2 ml) and dried in vacuo. Resin was suspended in 4 ml of dry dichloromethane before addition of 315 mg (1.4 mmol, 10 equiv.) of sodium triacetylborohydride and shaken overnight. Resin was filtered off and washed by MeOH (1×5 ml), (9/1) THF/NEt$_3$ (3×5 ml×15 minutes), (1/1) THF/water (2×5 ml) and consecutive wash of methyl alcohol and dichloromethane (4×5 ml). Resin was dried in vacuo after washing with diethyl ether (1×5 ml).

Typical "CDI Procedure" on Solid Phase

To a suspension of 95 mg (0.136 mmol, 1 equiv.) of N,N-dialkylaminoalcohol resin in 5 ml of dry THF was added 220 mg (1.36 mmol, 10 equiv.) of carbonyldiimidazole. The resin was shaken overnight, filtered off and washed by dry THF (3×5 ml for 5 minutes). Resin was suspended in 10 ml of dry THF and 147 mg (0.68 mmol, 5 equiv.) of 4-(2-keto-1-benzimidazolinyl)-piperidine was added. The resin was shaken for 72 hours, filtered off, washed by DMF (3×4 ml) and consecutively by methyl alcohol and dichloromethane (4×10 ml). Resin was dried in vacuo after washing with diethyl ether (1×5 ml).

Typical Cleavage Procedure

To a suspension of 53 mg (0.076 mmol, 1 equiv.) of triazene resin in 2 ml of dry dichloromethane was added at room temperature 30 µL (0.30 mmol, 4 equiv.) of trichlorosilane. The suspension was shaken for 12 hours and the excess of trichlorosilane was destroyed by addition of silica until no gas appeared and directly eluted by 5 ml of methyl alcohol. The filtrate was concentrated in vacuo and purified on a shortpad of aminopropyl silica gel (eluent dichloromethane/methyl alcohol 9/1) affording the desired pure compounds.

Preparation of 2-(N-(4-nitrobenzyl)-N-benzylamino) ethyl 4-(1,2-dihydro-2-oxobenzo[d]imidazol-3-yl) piperidine-1-carboxylate (Compound no 28)

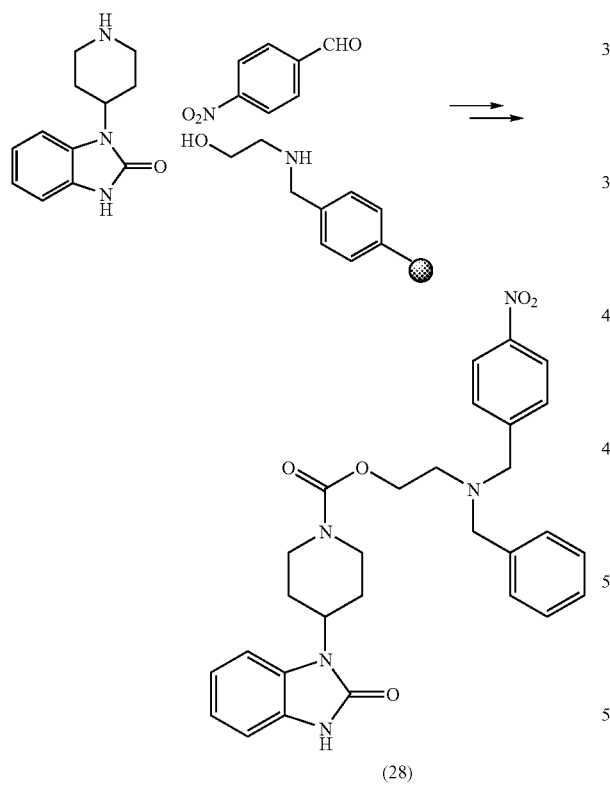

(28)

Colorless oil (16% for six steps).

Preparative HPLC $^1$H NMR (400 MHz, CDCl$_3$, ppm) δ 9.11 (s, 1H, NH), 8.17 (d, J=8.4 Hz, 2H, Ph), 7.56 (d, J=8.4 Hz, 2H, Ph), 7.32 (t, J=7.6 Hz, 5H, Ph), 7.06 (m, 4H, Ph), 4.50 (m, 2H, CHCH$_2$CH$_2$N), 4.26 (m, 3H, CHCH$_2$CH$_2$N, OCH$_2$CH$_2$N), 3.76 (s, 2H, CH$_2$Ph), 3.68 (s, 2H, CH$_2$Ph), 2.93 (m, 2H, CHCH$_2$CH$_2$N), 2.79 (t, J=5.6 Hz, 2H, OCH$_2$CH$_2$N), 2.35 (m, 2H, CHCH$_2$CH$_2$N), 1.86 (d, J=11.6 Hz, 2H, CHCH$_2$CH$_2$N)

LC/MS (ES$^+$) m/z 530.3 (M+H)$^+$

Preparation of (S)-2-(benzyl(4-nitrobenzyl)amino) propyl 4-(2-oxo-2,3-dihydro-1H-benzo[d]imidazol-1-yl)piperidine-1-carboxylate hydrochloride (Compound no 36)

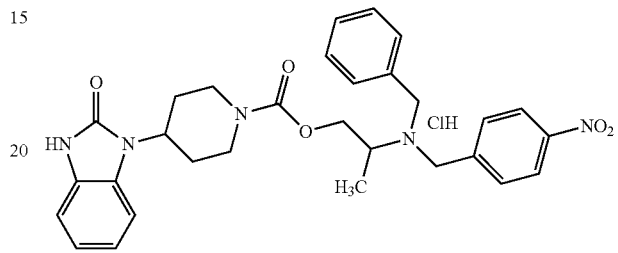

(36)

$^1$H NMR (400 MHz, MeOD) δ 8.16 (d, J=8.8 Hz, 2H, Ph), 7.63 (d, J=8.8 Hz, 2H, Ph), 7.37 (d, J=7.2 Hz, 2H, Ph), 7.28 (t, J=7.2 Hz, 2H, Ph), 7.19 (m, 2H, Ph), 7.05 (m, 3H, Ph), 4.47 (m, 1H, CHCH$_2$CH$_2$N), 4.33 (m, 3H, CHCH$_2$CH$_2$N, CH$_2$O), 3.95 (m, 1H, CH$_2$O), 3.90 (d, J=15.0 Hz, 1H, NCH$_2$Ph), 3.77 (d, J=14.0 Hz, 1H, NCH$_2$Ph), 3.70 (d, J=15.0 Hz, 1H, NCH$_2$Ph), 3.61 (d, J=14.0 Hz, 1H, NCH$_2$Ph), 3.12 (m, 3H, CHCH$_3$, CHCH$_2$CH$_2$N), 2.40 (m, 2H, CHCH$_2$CH$_2$N), 1.85 (m, 2H, CHCH$_2$CH$_2$N), 1.13 (d, J=6.8 Hz, 3H, CHCH$_3$)

LC/MS (ES$^+$) m/z 544.2 (M+H)$^+$

Preparation of (S)-2-(benzyl(4-methoxybenzyl) amino)propyl 4-(2-oxo-2,3-dihydro-1H-benzo[d] imidazol-1-yl)piperidine-1-carboxylate hydrochloride (Compound no 39)

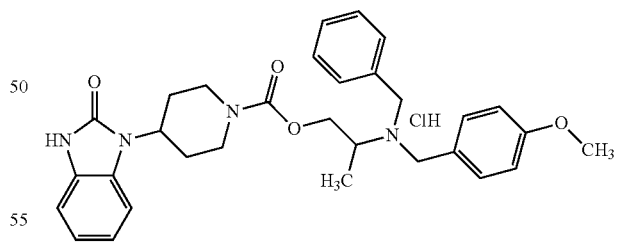

(39)

$^1$H NMR (400 MHz, MeOD) δ 8.30 (s, 1H, NH), 7.43 (d, J=7.2 Hz, 2H, Ar), 7.36 (m, 4H, Ar), 7.27 (m, 2H, Ar), 7.10 (m, 3H, Ar), 6.92 (d, J=8.4 Hz, 2H, Ar), 4.40 (m, 1H, CHCH$_2$CH$_2$N), 4.36 (m, 3H, CHCH$_2$CH$_2$N, CH$_2$O), 4.05 (m, 1H, CH$_2$O), 3.80 (m, 2H, NCH$_2$Ph), 3.62 (m, 2H, NCH$_2$Ph), 3.40 (s, 3H, OMe), 3.19 (m, 1H, CHCH$_3$), 3.05 (m, 2H, CHCH$_2$CH$_2$N), 2.40 (m, 2H, CHCH$_2$CH$_2$N), 1.88 (m, 2H, CHCH$_2$CH$_2$N), 1.17 (d, J=6.8 Hz, 3H, CHCH$_3$).

LC/MS (ES$^+$) m/z 529.2 (M+H)$^+$

Preparation of 3-(benzyl(4-methoxybenzyl)amino) propyl 4-(2-oxo-2,3-dihydro-1H-benzo[d]imidazol-1-yl)piperidine-1-carboxylate hydrochloride (Compound no 42)

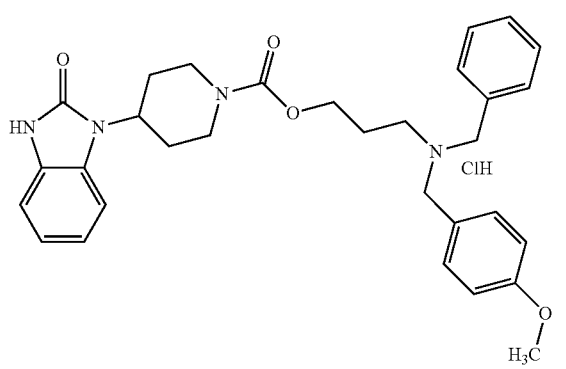

(42)

$^1$H NMR (400 MHz, MeOD) δ 8.26 (s, 1H, NH), 7.42-7.32 (m, 7H, Ar), 7.16 (m, 1H, Ar), 7.07 (m, 3H, Ar), 6.92 (d, J=8.4 Hz, 2H, Ar), 4.27 (m, 1H, CHCH$_2$CH$_2$N), 4.16 (m, 2H, CHCH$_2$CH$_2$N), 4.05 (t, J=5.6 Hz, 2H, CH$_2$O), 3.95 (s, 2H, NCH$_2$Ph), 3.90 (s, 2H, NCH$_2$Ph), 3.74 (s, 3H, OMe), 2.84 (m, 4H, CH$_2$CH$_2$N, CHCH$_2$CH$_2$N), 2.31 (m, 2H, CHCH$_2$CH$_2$N), 1.99 (m, 2H, CH$_2$CH$_2$N), 1.73 (m, 2H, CHCH$_2$CH$_2$N).

LC/MS (ES$^+$) m/z 529.2 (M+H)$^+$

Preparation of 2-(benzyl(3-phenoxybenzyl)amino) ethyl 4-(2-oxo-2,3-dihydro-1H-benzo[d]imidazol-1-yl)piperidine-1-carboxylate hydrochloride (Compound no 49)

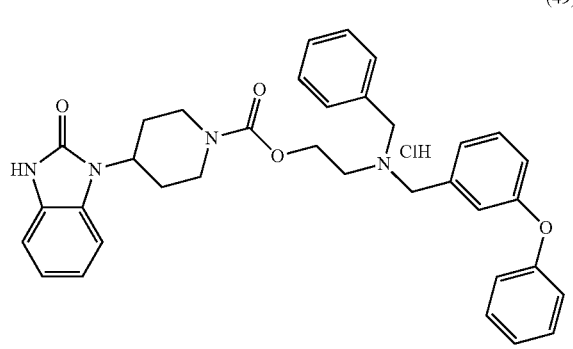

(49)

$^1$H NMR (400 MHz, MeOD) δ 7.31 (m, 7H, Ar), 7.27 (m, 3H, Ar), 7.04 (m, 4H, Ar), 6.93 (d, J=8.8 Hz, 2H, Ar), 6.85 (m, 1H, Ar), 4.39 (m, 1H, CHCH$_2$CH$_2$N), 4.19 (m, 4H, CHCH$_2$CH$_2$N, CH$_2$O), 3.66 (s, 2H, NCH$_2$Ph), 3.64 (s, 2H, NCH$_2$Ph), 2.77 (m, 2H, CHCH$_2$CH$_2$N), 2.77 (d, J=5.6 Hz, 2H, CH$_2$N), 2.31 (m, 2H, CHCH$_2$CH$_2$N), 1.74 (m, 2H, CHCH$_2$CH$_2$N).

LC/MS (ES$^+$) m/z 577.1 (M+H)$^+$

Example 2

Assay of the Activity of Compounds of Formula (I) by Measuring the Inhibition of Plant MGDG Synthesis In Vitro I) Assay of Properties of Compounds of Formula (I) by Measuring the Inhibition of Recombinant MGDG Synthases From Spinach (*Spinacia olearacea*) and *Arabidopsis* (*Arabidopsis thaliana*) Expressed in *Escherichia coli*

1) Material and Method 1-a) Functional Expression of Recombinant Spinach and *Arabidopsis* MGDG Synthases in *Escherichia coli*.

The cDNA fragments corresponding to the mature form of spinach MGDG synthase, soMGD1 [accession number CAB56218], and from the three isoforms that are present in *Arabidopsis*, i.e. atMGD1 [accession number BAB12042], atMGD2 [accession number T52269] and atMGD3 [accession number BAB12041] were inserted into the pET-3a expression vector from Novagen, as described by Miège C. et al., Eur. J. Biochem, 1999, 265, 990-1001 and Awai K. et al., Proc. Natl. Acad. Sci. U.S.A., 2001, 98, 10960-10965. All MGD sequences used in this study were inserted in NdeI-BamHI cloning site of the pET-3a vector. Induction of recombinant proteins was achieved following the pET expression system procedure. Isolated colonies of transfected *Escherichia coli* (BL21-DE3) were inoculated in LB medium (2.5 ml, 100 μg/ml carbenicillin) and grown at 37° C. When OD$_{600}$ reached 0.5, the cell suspension was transferred to 15 ml of LB medium (100 mg/ml carbenicillin) and grown at 37° C. until OD$_{600}$ reached 0.5. Cells were then transferred to 400 ml of LB medium (100 μg/ml carbenicillin) and grown until OD$_{600}$ reached 0.5. isopropyl-β-D-thiogalactopyranoside (IPTG) (0.4 mM) was subsequently added and the suspension was incubated at 28° C. or 37° C. for 4 hours. Cells were harvested by centrifugation and used for enzymatic assay of MGDG synthase activities.

1-b) MGDG Synthase Enzymatic Assay of Recombinant MGD Proteins, in Mixed Micelles Supplied with Exogenous Diacylglycerol The MGDG synthase enzymatic assay was achieved as described by Maréchal E. et al., J. Biol. Chem., 1995, 270, 5714-5722. The assay is based on the solubilization of the MGD protein by a zwitterionic detergent (6 mM CHAPS) in mixed micelles also comprising the hydrophobic co-substrate, i.e., dioleoylglycerol (DOG) provided exogenously. Reaction starts by addition of 1 mM UDP-[$^{14}$C]galactose (37 Bq·μmol$^{-1}$) and stopped by addition of chloroform/methanol (1:2, v/v). The lipids are subsequently extracted by the method described by Bligh and Dyer, Can. J. Biochem. Physiol., 1959, 37, 911-917 and the radioactivity of the [$^{14}$C]-labelled MGDG ultimately produced, determined by liquid scintillation counting. Activity is expressed in μmol incorporated galactose.h$^{-1}$.mg protein$^{-1}$.

2) Results

In this example, the activity of (S)-2-(dibenzylamino)propyl 4-(1,2-dihydro-2-oxobenzo[d]imidazol-3-yl)piperidine-1-carboxylate [compounds (7)] and of S)-2-(dibenzylamino)-3-phenylpropyl 4-(1,2-dihydro-2-oxobenzo[d]imidazol-3-yl)piperidine-1-carboxylate [compound (8)] as above prepared has been tested The results are reported on FIGS. 2 and 3 annexed.

FIG. 2 represents the effect of (compound (7) and (compound (8) on the activity of spinach recombinant MGDG synthase (soMGD).

In these conditions the inhibition is characterized by an IC$_{50}$ of 45 μM for compound (7) and 100 μM for compound (8). Nisin and vancomycin, which are antibiotic molecules inhibiting MURG activity, were used as negative controls.

FIG. 3 shows the effect of compounds (7) and (8) on the activity of *Arabidopsis* recombinant MGDG synthase atMGD1, atMGD2 and atMGD3.

In these conditions the inhibition is characterized by an $IC_{50}$ ranging from 5 µM to 80 µM for compound (7) and compound (8), depending on the MGD isoform. In any case, all the three MGDG synthase proteins (atMGD1, atMGD2 and atMGD3) were sensitive to the molecule. Compounds shown in FIG. 3, inhibiting *Arabidopsis* MGDG synthases are the same as those shown in FIG. 2, inhibiting spinach MGDG synthase. Thus, the measure of an inhibitory effect on a MGDG synthase activity from one Angiosperm species supports that an inhibitory effect on MGDG synthase activity also occurs in other plant species.

II) Assay of Properties of Molecules by Measuring the Inhibition of MGDG Synthase Activity in Envelope Membrane Fractions Isolated from Spinach Chloroplasts (*Spinacia oleracea*)

1) Material and Method for the Purification of Spinach Chloroplast Envelope Membranes All the operations have been carried out as described in the article by Maréchal, E. et al., J. Biol. Chem., 1995, 270, 5714-5722. Crude chloroplasts were obtained from 3-4 kg of spinach leaves and purified by isopycnic centrifugation using Percoll gradients. Purified intact chloroplasts have then been lysed in hypotonic medium and envelope membranes purified from the lysate by sucrose centrifugation gradient as described in the article by Douce, R. and Joyard, J., (1982) in Methods in Chloroplast Molecular Biology (Edelman, M., Hallick R and Chua N H eds), pp 239-256, Elsevier Science Publishers B.V. Amsterdam.

MGDG synthase activity was assayed as described in the article by Maréchal et al. (1995).

II) Results

The results obtained are reported on FIG. 4 annexed.

FIG. 4 shows the effect of compound (7) on the MGDG synthase activity measured in the membrane compartment where the enzyme sits in vivo, i.e. the envelope membranes that surround chloroplasts.

This results show that compound (7) inhibits the activity with an $IC_{50}$ of 10 µM.

Results obtained in the same manner with different compounds of formula (I) according to the invention are reported in Table 1 below:

TABLE 1

| Compound n° (Synthesis example if any) | Name of the tested compound | Inhibitory effect on MGDG synthesis in isolated spinach chloroplast envelope membranes |
| --- | --- | --- |
| 7 | (S)-2-(dibenzylamino)propyl 4-(1,2-dihydro-2-oxobenzo[d]imidazol-3-yl)piperidine-1-carboxylate | 45 µM |
| 8 | (S)-2-(dibenzylamino)-3-phenylpropyl 4-(1,2-dihydro-2-oxobenzo[d]imidazol-3-yl)piperidine-1-carboxylate | 10 µM |
| 11 | 2-(dibenzylamino)ethyl 4-(1,2-dihydro-2-oxobenzo[d]imidazol-3-yl)piperidine-1-carboxylate | 15 µM |
| 10 | 3-(dibenzylamino)propyl 4-(1,2-dihydro-2-oxobenzo[d]imidazol-3-yl)piperidine-1-carboxylate | 45 µM |
| 9 | 2-(N-benzyl-N-methylamino)ethyl 4-(1,2-dihydro-2-oxobenzo[d]imidazol-3-yl)piperidine-1-carboxylate | 100-500 µM |
| 25 | (S)-2-(dibenzylamino)propyl 4-(1,2-dihydro-2-thioxobenzo[d]imidazol-3-yl)piperidine-1-carboxylate | 100-500 µM |
| 1 | (S)-2-(dibenzylamino)propyl 4-(1H-benzo[d]imidazol-1-yl)piperidine-1-carboxylate | 100-500 µM |
| 19 | O-2-(dibenzylamino)ethyl 4-(1,2-dihydro-2-oxobenzo[d]imidazol-3-yl)piperidine-1-carbothioate | 20 µM |
| 20 | O-2-(benzyloxy)ethyl 4-(1,2-dihydro-2-oxobenzo[d]imidazol-3-yl)piperidine-1-carbothioate | 100-500 µM |
| 2 | (S)-2-(dibenzylamino)propyl 4-(2,3-dihydro-2-oxoimidazo[4,5-b]pyridin-1-yl)piperidine-1-carboxylate | 100-500 µM |
| 21 | (S)-2-(dibenzylamino)propyl 4-(1,2-dihydro-2-oxo-1-(benzoyl)benzo[d]imidazol-3-yl)piperidine-1-carboxylate | 50 µM |
| 4 | (S)-2-(dibenzylamino)propyl 4-(1,2-dihydro-2-oxobenzo[d]imidazol-3-yl)azepane-1-carboxylate | 200 µM |
| 13 | 1-benzhydrylazetidin-3-yl 4-(1,2-dihydro-2-oxobenzo[d]imidazol-3-yl)piperidine-1-carboxylate | 100-500 µM |
| 15 | 2-(1,3-dioxoisoindolin-2-yl)ethyl 4-(1,2-dihydro-2-oxobenzo[d]imidazol-3-yl)piperidine-1-carboxylate | 45 µM |
| 17 | 2-(ethyl(phenyl)amino)ethyl 4-(2-oxo-2,3-dihydro-1H-benzo[d]imidazol-1-yl)piperidine-1-carboxylate | 200 µM |
| 12 | 3,3-diphenylpropyl 4-(1,2-dihydro-2-oxobenzo[d]imidazol-3-yl)piperidine-1-carboxylate | 45 µM |
| 6 | (S)-2-(dibenzylamino)propyl 3-(1,2-dihydro-2-oxobenzo[d]imidazol-3-yl)pyrrolidine-1-carboxylate | 50 µM |
| 24 | 1-[1-(4-dibenzylamino-butyryl)-piperidin-4-yl]-1,3-dihydro-benzoimidazol-2-one | 25 µM |
| 22 | (S)-2-(dibenzylamino)-3-phenylpropyl 4-(1,2-dihydro-1-methyl-2-oxobenzo[d]imidazol-3-yl)piperidine-1-carboxylate | 75 µM |
| 23 | N-((S)-2-(dibenzylamino)propyl)-4-(1,2-dihydro-2-oxobenzo[d]imidazol-3-yl)piperidine-1-carbothioamide | 50 µM |
| 18 | 2,2-diphenylethyl 4-(1,2-dihydro-2-oxobenzo[d]imidazol-3-yl)piperidine-1-carboxylate | 50 µM |

TABLE 1-continued

| Compound n° (Synthesis example if any) | Name of the tested compound | Inhibitory effect on MGDG synthesis in isolated spinach chloroplast envelope membranes |
|---|---|---|
| 28 | 2-(N-(4-nitrobenzyl)-N-benzylamino)ethyl 4-(1,2-dihydro-2-oxobenzo[d]imidazol-3-yl)piperidine-1-carboxylate | 20 μM |
| 27 | 2-(dibenzylamino)propyl 4-(1,2-dihydro-2-oxobenzo[d]imidazol-3-yl)phenylcarbamate | 45 μM |
| 29 | (S)-2-(dibenzylamino)-3-methylbutyl 4-(1,2-dihydro-2-oxobenzo[d]imidazol-3-yl)piperidine-1-carboxylate | 8 μM |
| 30 | (S)-2-(dibenzylamino)-4-methylpentyl 4-(2-oxo-2,3-dihydro-1H-benzo[d]imidazol-1-yl)piperidine-1-carboxylate | 12 μM |
| 31 | 2-(dibenzylamino)-3,3-dimethylbutyl 4-(1,2-dihydro-2-oxobenzo[d]imidazol-3-yl)piperidine-1-carboxylate | 50 μM |
| 32 | 3-(dibenzylamino)butyl 4-(1,2-dihydro-2-oxobenzo[d]imidazol-3-yl)piperidine-1-carboxylate | 35 μM |
| 33 | 2-(dibenzylamino)-2-methylpropyl 4-(1,2-dihydro-2-oxobenzo[d]imidazol-3-yl)piperidine-1-carboxylate | 50 μM |
| 34 | (S)-2-(dibenzylamino)-2-phenylethyl 4-(1,2-dihydro-2-oxobenzo[d]imidazol-3-yl)piperidine-1-carboxylate | 40 μM |
| 35 | 2-(N-benzyl-N-phenylamino)ethyl 4-(1,2-dihydro-2-oxobenzo[d]imidazol-3-yl)piperidine-1-carboxylate | 40 μM |
| 36 | (S)-2-(benzyl(4-nitrobenzyl)amino)propyl 4-(2-oxo-2,3-dihydro-1H-benzo[d]imidazol-1-yl)piperidine-1-carboxylate hydrochloride | 50 μM |
| 37 | (S)-2-(benzyl(4-nitrobenzyl)amino)propyl 4-(2-oxo-2,3-dihydro-1H-benzo[d]imidazol-1-yl)piperidine-1-carboxylate | 50 μM |
| 38 | 3-(benzyl(4-nitrobenzyl)amino)propyl 4-(2-oxo-2,3-dihydro-1H-benzo[d]imidazol-1-yl)piperidine-1-carboxylate hydrochloride | 15 μM |
| 39 | (S)-2-(benzyl(4-methoxybenzyl)amino)propyl 4-(2-oxo-2,3-dihydro-1H-benzo[d]imidazol-1-yl)piperidine-1-carboxylate hydrochloride | 60 μM |
| 40 | 2-(benzyl(4-bromobenzyl)amino)ethyl 4-(2-oxo-2,3-dihydro-1H-benzo[d]imidazol-1-yl)piperidine-1-carboxylate hydrochloride | 15 μM |
| 41 | (S)-2-(benzyl(4-bromobenzyl)amino)propyl 4-(2-oxo-2,3-dihydro-1H-benzo[d]imidazol-1-yl)piperidine-1-carboxylate hydrochloride | 50 μM |
| 42 | 3-(benzyl(4-methoxybenzyl)amino)propyl 4-(2-oxo-2,3-dihydro-1H-benzo[d]imidazol-1-yl)piperidine-1-carboxylate hydrochloride | 50 μM |
| 43 | (R)-2-(dibenzylamino)-3-phenylpropyl 4-(1,2-dihydro-2-oxobenzo[d]imidazol-3-yl)piperidine-1-carboxylate | 6 μM |
| 44 | 2-(benzyl(pyridin-4-ylmethyl)amino)ethyl 4-(2-oxo-2,3-dihydro-1H-benzo[d]imidazol-1-yl)piperidine-1-carboxylate | 45 μM |
| 45 | 2-(benzyl(4-fluorobenzyl)amino)ethyl 4-(2-oxo-2,3-dihydro-1H-benzo[d]imidazol-1-yl)piperidine-1-carboxylate hydrochloride | 5 μM |
| 46 | 2-(benzyl(3-phenylpropyl)amino)ethyl 4-(2-oxo-2,3-dihydro-1H-benzo[d]imidazol-1-yl)piperidine-1-carboxylate hydrochloride | 15 μM |
| 47 | 2-(benzyl(4-methoxybenzyl)amino)ethyl 4-(2-oxo-2,3-dihydro-1H-benzo[d]imidazol-1-yl)piperidine-1-carboxylate hydrochloride | 15 μM |
| 48 | 2-(benzyl(3-methoxybenzyl)amino)ethyl 4-(2-oxo-2,3-dihydro-1H-benzo[d]imidazol-1-yl)piperidine-1-carboxylate hydrochloride | 15 μM |
| 49 | 2-(benzyl(3-phenoxybenzyl)amino)ethyl 4-(2-oxo-2,3-dihydro-1H-benzo[d]imidazol-1-yl)piperidine-1-carboxylate hydrochloride | 8 μM |
| 50 | 2-(benzyl(3-chlorobenzyl)amino)ethyl 4-(2-oxo-2,3-dihydro-1H-benzo[d]imidazol-1-yl)piperidine-1-carboxylate hydrochloride | 8 μM |
| 51 | (S)-2-(benzyl(4-fluorobenzyl)amino)propyl 4-(2-oxo-2,3-dihydro-1H-benzo[d]imidazol-1-yl)piperidine-1-carboxylate hydrochloride | 40 μM |
| 52 | (S)-2-(benzyl(3-phenylpropyl)amino)propyl 4-(2-oxo-2,3-dihydro-1H-benzo[d]imidazol-1-yl)piperidine-1-carboxylate hydrochloride | 60 μM |
| 53 | (S)-2-(benzyl(quinolin-4-ylmethyl)amino)propyl 4-(2-oxo-2,3-dihydro-1H-benzo[d]imidazol-1-yl)piperidine-1-carboxylate hydrochloride | 60 μM |

TABLE 1-continued

| Compound n° (Synthesis example if any) | Name of the tested compound | Inhibitory effect on MGDG synthesis in isolated spinach chloroplast envelope membranes |
|---|---|---|
| 54 | (S)-2-(benzyl(3-methoxybenzyl)amino)propyl 4-(2-oxo-2,3-dihydro-1H-benzo[d]imidazol-1-yl)piperidine-1-carboxylate hydrochloride | 25 μM |
| 55 | (S)-2-(benzyl(3-phenoxybenzyl)amino)propyl 4-(2-oxo-2,3-dihydro-1H-benzo[d]imidazol-1-yl)piperidine-1-carboxylate hydrochloride | 40 μM |
| 56 | (S)-2-(benzyl(3-chlorobenzyl)amino)propyl 4-(2-oxo-2,3-dihydro-1H-benzo[d]imidazol-1-yl)piperidine-1-carboxylate hydrochloride | 15 μM |
| 57 | 2-(benzyl(quinolin-4-ylmethyl)amino)ethyl 4-(2-oxo-2,3-dihydro-1H-benzo[d]imidazol-1-yl)piperidine-1-carboxylate hydrochloride | 75 μM |
| 58 | 3-(benzyl(pyridin-3-ylmethyl)amino)propyl 4-(2-oxo-2,3-dihydro-1H-benzo[d]imidazol-1-yl)piperidine-1-carboxylate hydrochloride | 17 μM |
| 59 | 3-(benzyl(pyridin-2-ylmethyl)amino)propyl 4-(2-oxo-2,3-dihydro-1H-benzo[d]imidazol-1-yl)piperidine-1-carboxylate hydrochloride | 15 μM |
| 60 | (S)-2-(benzyl(3-(benzyloxy)benzyl)amino)propyl 4-(2-oxo-2,3-dihydro-1H-benzo[d]imidazol-1-yl)piperidine-1-carboxylate hydrochloride | 12 μM |
| 61 | (S)-2-(benzyl(phenanthren-9-ylmethyl)amino)propyl 4-(2-oxo-2,3-dihydro-1H-benzo[d]imidazol-1-yl)piperidine-1-carboxylate hydrochloride | 25 μM |
| 62 | (S)-2-(benzyl(naphthalen-1-ylmethyl)amino)propyl 4-(2-oxo-2,3-dihydro-1H-benzo[d]imidazol-1-yl)piperidine-1-carboxylate hydrochloride | 25 μM |
| 63 | (S)-2-(benzyl(thiophen-2-ylmethyl)amino)propyl 4-(2-oxo-2,3-dihydro-1H-benzo[d]imidazol-1-yl)piperidine-1-carboxylate hydrochloride | 30 μM |
| 64 | (S)-2-(benzyl(pyridin-2-ylmethyl)amino)propyl 4-(2-oxo-2,3-dihydro-1H-benzo[d]imidazol-1-yl)piperidine-1-carboxylate hydrochloride | 35 μM |
| 65 | 2-(benzyl(tert-butoxycarbonyl)amino)ethyl 4-(2-oxo-2,3-dihydro-1H-benzo[d]imidazol-1-yl)piperidine-1-carboxylate | 12 μM |
| 66 | 3-(benzyl(thiophen-2-ylmethyl)amino)propyl 4-(2-oxo-2,3-dihydro-1H-benzo[d]imidazol-1-yl)piperidine-1-carboxylate hydrochloride | 50 μM |
| 67 | 3-(benzyl(4-fluorobenzyl)amino)propyl 4-(2-oxo-2,3-dihydro-1H-benzo[d]imidazol-1-yl)piperidine-1-carboxylate hydrochloride | 12 μM |
| 68 | 3-(benzyl(3-methoxybenzyl)amino)propyl 4-(2-oxo-2,3-dihydro-1H-benzo[d]imidazol-1-yl)piperidine-1-carboxylate hydrochloride | 80 μM |
| 69 | 3-(benzyl(3-chlorobenzyl)amino)propyl 4-(2-oxo-2,3-dihydro-1H-benzo[d]imidazol-1-yl)piperidine-1-carboxylate hydrochloride | 30 μM |
| 70 | 3-(benzyl(naphthalen-1-ylmethyl)amino)propyl 4-(2-oxo-2,3-dihydro-1H-benzo[d]imidazol-1-yl)piperidine-1-carboxylate hydrochloride | 60 μM |
| 71 | 3-(benzyl(quinolin-4-ylmethyl)amino)propyl 4-(2-oxo-2,3-dihydro-1H-benzo[d]imidazol-1-yl)piperidine-1-carboxylate hydrochloride | 50 μM |
| 72 | 3-(benzyl((1-methyl-1H-indol-2-yl)methyl)amino)propyl 4-(2-oxo-2,3-dihydro-1H-benzo[d]imidazol-1-yl)piperidine-1-carboxylate hydrochloride | 50 μM |
| 73 | 3-(benzyl(3-phenoxybenzyl)amino)propyl 4-(2-oxo-2,3-dihydro-1H-benzo[d]imidazol-1-yl)piperidine-1-carboxylate hydrochloride | 15 μM |
| 74 | 2-(benzyl(4-chlorobenzyl)amino)ethyl 4-(2-oxo-2,3-dihydro-1H-benzo[d]imidazol-1-yl)piperidine-1-carboxylate | 8 μM |
| 75 | 2-(benzyl(2-methoxybenzyl)amino)ethyl 4-(2-oxo-2,3-dihydro-1H-benzo[d]imidazol-1-yl)piperidine-1-carboxylate | 10 μM |
| 76 | 2-(benzyl(2-(benzyloxy)benzyl)amino)ethyl 4-(2-oxo-2,3-dihydro-1H-benzo[d]imidazol-1-yl)piperidine-1-carboxylate | 20 μM |
| 77 | 2-(benzyl(4-(benzyloxy)benzyl)amino)ethyl 4-(2-oxo-2,3-dihydro-1H-benzo[d]imidazol-1-yl)piperidine-1-carboxylate | 30 μM |

TABLE 1-continued

| Compound n° (Synthesis example if any) | Name of the tested compound | Inhibitory effect on MGDG synthesis in isolated spinach chloroplast envelope membranes |
|---|---|---|
| 78 | 2-(benzyl(2,6-difluorobenzyl)amino)ethyl 4-(2-oxo-2,3-dihydro-1H-benzo[d]imidazol-1-yl)piperidine-1-carboxylate | 8 μM |
| 79 | (S)-2-(benzyl(furan-2-ylmethyl)amino)propyl 4-(2-oxo-2,3-dihydro-1H-benzo[d]imidazol-1-yl)piperidine-1-carboxylate | 25 μM |
| 80 | 3-(benzyl(furan-3-ylmethyl)amino)propyl 4-(2-oxo-2,3-dihydro-1H-benzo[d]imidazol-1-yl)piperidine-1-carboxylate | 50 μM |
| 81 | 2-(benzyl(3-(benzyloxy)benzyl)amino)ethyl 4-(2-oxo-2,3-dihydro-1H-benzo[d]imidazol-1-yl)piperidine-1-carboxylate | 8 μM |
| 82 | (E)-2-(benzyl(cinnamyl)amino)ethyl 4-(2-oxo-2,3-dihydro-1H-benzo[d]imidazol-1-yl)piperidine-1-carboxylate | 50 μM |
| 83 | 3-(benzyl(4-chlorobenzyl)amino)propyl 4-(2-oxo-2,3-dihydro-1H-benzo[d]imidazol-1-yl)piperidine-1-carboxylate | 12 μM |
| 84 | 3-(benzyl(3-(benzyloxy)benzyl)amino)propyl 4-(2-oxo-2,3-dihydro-1H-benzo[d]imidazol-1-yl)piperidine-1-carboxylate | 45 μM |
| 85 | (S)-2-(benzyl(tert-butoxycarbonyl)amino)-4-methylpentyl 4-(2-oxo-2,3-dihydro-1H-benzo[d]imidazol-1-yl)piperidine-1-carboxylate | 10 μM |
| 86 | (S)-2-(benzyl(tert-butoxycarbonyl)amino)-3-phenylpropyl 4-(2-oxo-2,3-dihydro-1H-benzo[d]imidazol-1-yl)piperidine-1-carboxylate | 5 μM |
| 87 | (S)-2-(benzylamino)-4-methylpentyl 4-(2-oxo-2,3-dihydro-1H-benzo[d]imidazol-1-yl)piperidine-1-carboxylate | 45 μM |
| 88 | 2-(benzylamino)-3-phenylpropyl 4-(2-oxo-2,3-dihydro-1H-benzo[d]imidazol-1-yl)piperidine-1-carboxylate | 60 μM |
| 89 | 2-(benzyl(3-(benzyloxy)propyl)amino)propyl 4-(2-oxo-2,3-dihydro-1H-benzo[d]imidazol-1-yl)piperidine-1-carboxylate | 40 μM |

Example 3

Effect of Compounds of Formula (I) on Plant and Algae Growth

1) Assay of Properties of Compounds of Formula (I) by Measuring the Inhibition of Plant Growth.

1-a) Material and Method

Plant Growth Assays.

Seeds of *Arabidopsis thaliana*, ecotype Columbia, were washed in Barychlore 10%, v/v; Triton-X100 0.5%; ethanol 90% and sawn on agarose solid medium supplemented with Murashige and Skoog medium (400 μl Murashige and Skoog medium, sucrose 5 g/l, agar 15%) in Cellstar 48-well sterile microplates. Molecules solubilized in dimethylsulfoxide (DMSO) were supplied directly in the growth medium, at concentrations ranging from 0 to 200 μM. Final concentration of DMSO in solid medium was 10%. Seeds were activated at 4° C. during 48 h before transfer to growth chamber (humidity 80%; 20° C.; white light 150 μE.m-2.s−1) with a illumination cycle of 12 h light/12 h darkness. Three seeds were sawn per well. Experiments were repeated from 2 to 4 times. Growth of plants was then observed and visualized 25 days after sawing.

Control herbicides are Glyphosate and Triclosan.

1-b) Results

The obtained results are reported in FIG. 5 annexed.

FIG. 5 represents is a photograph of the microplates and shows the herbicidal effect of Glyphosate and Triclosan, two known herbicides compared to 4 compounds of formula (I) according to the invention (Compounds 17, 13, 16 and 23).

These results demonstrate that these for compounds all have an herbicide activity.

The following Table 2) gives examples of additional compounds according to invention that have been assayed in the same conditions and having inhibitory activity on plant growth.

TABLE 2

| Compound n° (Synthesis example if any) | Name of the tested compound | Inhibitory effect on plant growth (*Arabidopsis*) |
|---|---|---|
| A | Glyphosate | 25 μM |
| B | Triclosan | 10 μM |
| 7 | (S)-2-(dibenzylamino)propyl 4-(1,2-dihydro-2-oxobenzo[d]imidazol-3-yl)piperidine-1-carboxylate | 100 μM |

TABLE 2-continued

| Compound n° (Synthesis example if any) | Name of the tested compound | Inhibitory effect on plant growth (*Arabidopsis*) |
|---|---|---|
| 11 | 2-(dibenzylamino)ethyl 4-(1,2-dihydro-2-oxobenzo[d]imidazol-3-yl)piperidine-1-carboxylate | 25 μM |
| 10 | 3-(dibenzylamino)propyl 4-(1,2-dihydro-2-oxobenzo[d]imidazol-3-yl)piperidine-1-carboxylate | 50 μM |
| 9 | 2-(N-benzyl-N-methylamino)ethyl 4-(1,2-dihydro-2-oxobenzo[d]imidazol-3-yl)piperidine-1-carboxylate | 100 μM |
| 1 | (S)-2-(dibenzylamino)propyl 4-(1H-benzo[d]imidazol-1-yl)piperidine-1-carboxylate | 50 μM |
| 19 | O-2-(dibenzylamino)ethyl 4-(1,2-dihydro-2-oxobenzo[d]imidazol-3-yl)piperidine-1-carbothioate | 200-500 μM |
| 20 | O-2-(benzyloxy)ethyl 4-(1,2-dihydro-2-oxobenzo[d]imidazol-3-yl)piperidine-1-carbothioate | 200 μM |
| 2 | (S)-2-(dibenzylamino)propyl 4-(2,3-dihydro-2-oxoimidazo[4,5-b]pyridin-1-yl)piperidine-1-carboxylate | 50 μM |
| 13 | 1-benzhydrylazetidin-3-yl 4-(1,2-dihydro-2-oxobenzo[d]imidazol-3-yl)piperidine-1-carboxylate | 25 μM |
| 15 | 2-(1,3-dioxoisoindolin-2-yl)ethyl 4-(1,2-dihydro-2-oxobenzo[d]imidazol-3-yl)piperidine-1-carboxylate | 100 μM |
| 17 | 2-(ethyl(phenyl)amino)ethyl 4-(2-oxo-2,3-dihydro-1H-benzo[d]imidazol-1-yl)piperidine-1-carboxylate | 50 μM |
| 6 | (S)-2-(dibenzylamino)propyl 3-(1,2-dihydro-2-oxobenzo[d]imidazol-3-yl)pyrrolidine-1-carboxylate | 50 μM |
| 24 | 1-[1-(4-dibenzylamino-butyryl)-piperidin-4-yl]-1,3-dihydro-benzoimidazol-2-one | 200-500 μM |
| 23 | N-((S)-2-(dibenzylamino)propyl)-4-(1,2-dihydro-2-oxobenzo[d]imidazol-3-yl)piperidine-1-carbothioamide | 100 μM |
| 28 | 2-(N-(4-nitrobenzyl)-N-benzylamino)ethyl 4-(1,2-dihydro-2-oxobenzo[d]imidazol-3-yl)piperidine-1-carboxylate | 200-500 μM |
| 27 | 2-(dibenzylamino)propyl 4-(1,2-dihydro-2-oxobenzo[d]imidazol-3-yl)phenylcarbamate | 200 μM |
| 32 | (S)-3-(dibenzylamino)butyl 4-(1,2-dihydro-2-oxobenzo[d]imidazol-3-yl)piperidine-1-carboxylate | 25 μM |
| 33 | 2-(dibenzylamino)-2-methylpropyl 4-(1,2-dihydro-2-oxobenzo[d]imidazol-3-yl)piperidine-1-carboxylate | 100 μM |
| 38 | 3-(benzyl(4-nitrobenzyl)amino)propyl 4-(2-oxo-2,3-dihydro-1H-benzo[d]imidazol-1-yl)piperidine-1-carboxylate hydrochloride | 100 μM |
| 39 | (S)-2-(benzyl(4-methoxybenzyl)amino)propyl 4-(2-oxo-2,3-dihydro-1H-benzo[d]imidazol-1-yl)piperidine-1-carboxylate hydrochloride | 100 μM |
| 40 | 2-(benzyl(4-bromobenzyl)amino)ethyl 4-(2-oxo-2,3-dihydro-1H-benzo[d]imidazol-1-yl)piperidine-1-carboxylate hydrochloride | 100 μM |
| 42 | 3-(benzyl(4-methoxybenzyl)amino)propyl 4-(2-oxo-2,3-dihydro-1H-benzo[d]imidazol-1-yl)piperidine-1-carboxylate hydrochloride | 100 μM |
| 44 | 2-(benzyl(pyridin-4-ylmethyl)amino)ethyl 4-(2-oxo-2,3-dihydro-1H-benzo[d]imidazol-1-yl)piperidine-1-carboxylate | 100 μM |
| 45 | 2-(benzyl(4-fluorobenzyl)amino)ethyl 4-(2-oxo-2,3-dihydro-1H-benzo[d]imidazol-1-yl)piperidine-1-carboxylate hydrochloride | 50 μM |
| 46 | 2-(benzyl(3-phenylpropyl)amino)ethyl 4-(2-oxo-2,3-dihydro-1H-benzo[d]imidazol-1-yl)piperidine-1-carboxylate hydrochloride | 50 μM |
| 47 | 2-(benzyl(4-methoxybenzyl)amino)ethyl 4-(2-oxo-2,3-dihydro-1H-benzo[d]imidazol-1-yl)piperidine-1-carboxylate hydrochloride | 50 μM |
| 48 | 2-(benzyl(3-methoxybenzyl)amino)ethyl 4-(2-oxo-2,3-dihydro-1H-benzo[d]imidazol-1-yl)piperidine-1-carboxylate hydrochloride | 25 μM |
| 52 | (S)-2-(benzyl(3-phenylpropyl)amino)propyl 4-(2-oxo-2,3-dihydro-1H-benzo[d]imidazol-1-yl)piperidine-1-carboxylate hydrochloride | 100 μM |
| 58 | 3-(benzyl(pyridin-3-ylmethyl)amino)propyl 4-(2-oxo-2,3-dihydro-1H-benzo[d]imidazol-1-yl)piperidine-1-carboxylate hydrochloride | 50 μM |
| 59 | 3-(benzyl(pyridin-2-ylmethyl)amino)propyl 4-(2-oxo-2,3-dihydro-1H-benzo[d]imidazol-1-yl)piperidine-1-carboxylate hydrochloride | 50 μM |
| 60 | (S)-2-(benzyl(3-(benzyloxy)benzyl)amino)propyl 4-(2-oxo-2,3-dihydro-1H-benzo[d]imidazol-1-yl)piperidine-1-carboxylate hydrochloride | 100 μM |
| 64 | (S)-2-(benzyl(pyridin-2-ylmethyl)amino)propyl 4-(2-oxo-2,3-dihydro-1H-benzo[d]imidazol-1-yl)piperidine-1- | 100 μM |

TABLE 2-continued

| Compound n° (Synthesis example if any) | Name of the tested compound | Inhibitory effect on plant growth (*Arabidopsis*) |
|---|---|---|
| | carboxylate hydrochloride | |
| 65 | 2-(benzyl(tert-butoxycarbonyl)amino)ethyl 4-(2-oxo-2,3-dihydro-1H-benzo[d]imidazol-1-yl)piperidine-1-carboxylate | 25 μM |
| 66 | 3-(benzyl(thiophen-2-ylmethyl)amino)propyl 4-(2-oxo-2,3-dihydro-1H-benzo[d]imidazol-1-yl)piperidine-1-carboxylate hydrochloride | 50-100 μM |
| 67 | 3-(benzyl(4-fluorobenzyl)amino)propyl 4-(2-oxo-2,3-dihydro-1H-benzo[d]imidazol-1-yl)piperidine-1-carboxylate hydrochloride | 50 μM |
| 90 | 3-(benzyl(3-phenylpropyl)amino)propyl 4-(2-oxo-2,3-dihydro-1H-benzo[d]imidazol-1-yl)piperidine-1-carboxylate hydrochloride | 100 μM |
| 68 | 3-(benzyl(3-methoxybenzyl)amino)propyl 4-(2-oxo-2,3-dihydro-1H-benzo[d]imidazol-1-yl)piperidine-1-carboxylate hydrochloride | 50 μM |
| 69 | 3-(benzyl(3-chlorobenzyl)amino)propyl 4-(2-oxo-2,3-dihydro-1H-benzo[d]imidazol-1-yl)piperidine-1-carboxylate hydrochloride | 50-100 μM |
| 70 | 3-(benzyl(naphthalen-1-ylmethyl)amino)propyl 4-(2-oxo-2,3-dihydro-1H-benzo[d]imidazol-1-yl)piperidine-1-carboxylate hydrochloride | 100 μM |
| 75 | 2-(benzyl(2-methoxybenzyl)amino)ethyl 4-(2-oxo-2,3-dihydro-1H-benzo[d]imidazol-1-yl)piperidine-1-carboxylate | 50-100 μM |
| 78 | 2-(benzyl(2,6-difluorobenzyl)amino)ethyl 4-(2-oxo-2,3-dihydro-1H-benzo[d]imidazol-1-yl)piperidine-1-carboxylate | 100 μM |
| 80 | 3-(benzyl(furan-3-ylmethyl)amino)propyl 4-(2-oxo-2,3-dihydro-1H-benzo[d]imidazol-1-yl)piperidine-1-carboxylate | 100 μM |
| 82 | (E)-2-(benzyl(cinnamyl)amino)ethyl 4-(2-oxo-2,3-dihydro-1H-benzo[d]imidazol-1-yl)piperidine-1-carboxylate | 50-100 μM |
| 83 | 3-(benzyl(4-chlorobenzyl)amino)propyl 4-(2-oxo-2,3-dihydro-1H-benzo[d]imidazol-1-yl)piperidine-1-carboxylate | 50-100 μM |
| 89 | 2-(benzyl(3-(benzyloxy)propyl)amino)propyl 4-(2-oxo-2,3-dihydro-1H-benzo[d]imidazol-1-yl)piperidine-1-carboxylate | 100 μM |

2) Assay of Properties of Compounds of Formula (I) by Measuring the Inhibition of Green Algae Growth.

2-a) Material and Method

*Chlamydomonas reinhardtii* Growth Assay.

An axenic suspension of *Chlamydomonas reinhardtii* (10 μl) is introduced in a liquid TAP medium (Tris-Acetate-Phosphate medium, as described by Rochaix et al., (The Molecular Biology of Chloroplasts and Mitochondria in Chlamydomeonas; Advances in Photosynthesis, (1998) Vol. 7. Kluwer Academic Publishers, Dordrecht, The Netherlands) with or without compound according to the invention. The compounds to be tested have been solubilized in dimethylsulfoxide (DMSO) and supplied directly in the growth medium, at concentrations ranging from 0 to 200 μM. Final concentration of DMSO in medium was 10%. *Chlamydomonas* suspensions were then grown at 20° C., under continuous light (50 $\mu E.m^{-2}.s^{-1}$). Growth was assessed by counting the algae in a 40 μl aliquot using a Malassez cell and examining the cell vitality by standard microscopic methods.

Control herbicide is Triclosan.

2-b) Results

Figure 6:
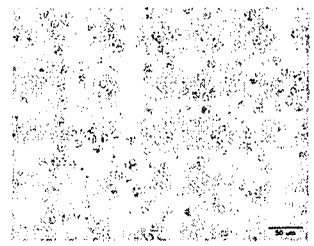
FIG. 6 shows the morphology of *Chlamydomonas* at day three (d=3) when incubated with each of Compounds (11), (20), (13) and (16).
Figure 6:
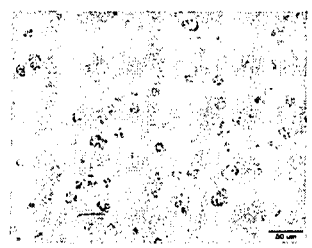
Figure 6:
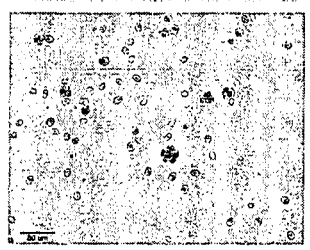
Figure 6:
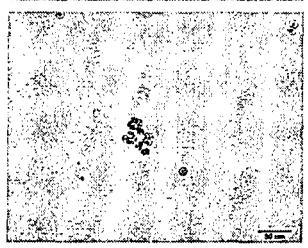
Figure 6:
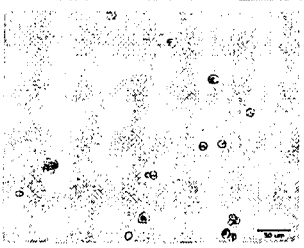

The corresponding results are reported on FIG. 6 annexed.

FIG. 6 is a photography showing the morphology of *Chlamydomonas* at day three (d=3) when incubated with compounds (11), (20), (13) or (16) according to the present Invention. In all cases, *Chlamydomonas* fails to divide, and shows aggregated cells which are unable to survive.

The following table 3 gives additional examples of compounds according to the present Invention that have been essayed in the same manner and that have inhibitory activity on green algae growth.

TABLE 3

| Compound n° (Synthesis example if any) | Name of the tested compound | Inhibitory effect on green algae growth (*Chlamydomonas*) |
|---|---|---|
| A | Triclosan | 1.2 μM |
| 11 | 2-(dibenzylamino)ethyl 4-(1,2-dihydro-2-oxobenzo[d]imidazol-3-yl)piperidine-1-carboxylate | 15 μM |
| 20 | O-2-(benzyloxy)ethyl 4-(1,2-dihydro-2-oxobenzo[d]imidazol-3-yl)piperidine-1-carbothioate | 100 μM |

TABLE 3-continued

| Compound n° (Synthesis example if any) | Name of the tested compound | Inhibitory effect on green algae growth (*Chlamydomonas*) |
|---|---|---|
| 13 | 1-benzhydrylazetidin-3-yl 4-(1,2-dihydro-2-oxobenzo[d]imidazol-3-yl)piperidine-1-carboxylate | 10 μM |
| 6 | (S)-2-(dibenzylamino)propyl 3-(1,2-dihydro-2-oxobenzo[d]imidazol-3-yl)pyrrolidine-1-carboxylate | 100 μM |
| 22 | (S)-2-(dibenzylamino)-3-phenylpropyl 4-(1,2-dihydro-1-methyl-2-oxobenzo[d]imidazol-3-yl)piperidine-1-carboxylate | 45 μM |
| 32 | 3-(dibenzylamino)butyl 4-(1,2-dihydro-2-oxobenzo[d]imidazol-3-yl)piperidine-1-carboxylate | 5 μM |
| 33 | 2-(dibenzylamino)-2-methylpropyl 4-(1,2-dihydro-2-oxobenzo[d]imidazol-3-yl)piperidine-1-carboxylate | 20 μM |
| 41 | (S)-2-(benzyl(4-bromobenzyl)amino)propyl 4-(2-oxo-2,3-dihydro-1H-benzo[d]imidazol-1-yl)piperidine-1-carboxylate hydrochloride | 5 μM |
| 44 | 2-(benzyl(pyridin-4-ylmethyl)amino)ethyl 4-(2-oxo-2,3-dihydro-1H-benzo[d]imidazol-1-yl)piperidine-1-carboxylate | 10 μM |
| 45 | 2-(benzyl(4-fluorobenzyl)amino)ethyl 4-(2-oxo-2,3-dihydro-1H-benzo[d]imidazol-1-yl)piperidine-1-carboxylate hydrochloride | 50-100 μM |
| 46 | 2-(benzyl(3-phenylpropyl)amino)ethyl 4-(2-oxo-2,3-dihydro-1H-benzo[d]imidazol-1-yl)piperidine-1-carboxylate hydrochloride | 50-100 μM |
| 47 | 2-(benzyl(4-methoxybenzyl)amino)ethyl 4-(2-oxo-2,3-dihydro-1H-benzo[d]imidazol-1-yl)piperidine-1-carboxylate hydrochloride | 50-100 μM |
| 48 | 2-(benzyl(3-methoxybenzyl)amino)ethyl 4-(2-oxo-2,3-dihydro-1H-benzo[d]imidazol-1-yl)piperidine-1-carboxylate hydrochloride | 50-100 μM |
| 58 | 3-(benzyl(pyridin-3-ylmethyl)amino)propyl 4-(2-oxo-2,3-dihydro-1H-benzo[d]imidazol-1-yl)piperidine-1-carboxylate hydrochloride | 20 μM |
| 59 | 3-(benzyl(pyridin-2-ylmethyl)amino)propyl 4-(2-oxo-2,3-dihydro-1H-benzo[d]imidazol-1-yl)piperidine-1-carboxylate hydrochloride | 50 μM |
| 65 | 2-(benzyl(tert-butoxycarbonyl)amino)ethyl 4-(2-oxo-2,3-dihydro-1H-benzo[d]imidazol-1-yl)piperidine-1-carboxylate | 30 μM |

The invention claimed is:

1. A compound of formula (I) below:

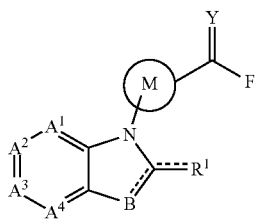

(I)

or an acid addition salt thereof, wherein:

$R^1$ represents a hydrogen atom, an oxygen atom or a sulphur atom;

$A^1$, $A^2$, $A^3$ and $A^4$, identical or different, represent N, —CH— or —CR$^2$— wherein $R^2$ represents a halogen atom or a group selected from alkoxy, alkyl, alkenyl, alkynyl, cycloalkyl, aryl, arylalkyl, heteroaryl and heteroalkyl groups, or a substituted group selected from alkoxy, alkyl, alkenyl, alkynyl, cycloalkyl, aryl, arylalkyl, heteroaryl or heteroalkyl groups, said substituent being one or more groups independently selected from halogen, trifluoromethyl, difluoromethyl, azido, alkyl, alkoxy, cyano and nitro, and when two adjacent cyclic atoms $A^1$, $A^2$, $A^3$ and $A^4$ represent —CR$^2$ or N, said two adjacent cyclic atoms may also form, together, a fused cycloalkyl, aryl or heteroaryl cyclic structure;

B represents —N—, —NR$^3$—, —S— or —O—, wherein $R^3$ represents hydrogen, an alkyl group or a group —COR$^4$ wherein $R^4$ represents an aryl or a heteroaryl group, said groups designated for $R^4$ being optionally substituted with one or more groups independently selected from halogen, trifluoromethyl, difluoromethyl, azido, alkyl, alkoxy, cyano and nitro;

the circled M represents a ring selected from the group consisting of the rings of following formula ($M_1$) to ($M_5$):

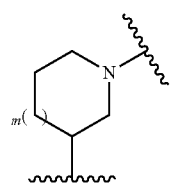

$M_1$

-continued

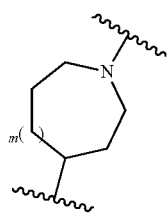
M₂

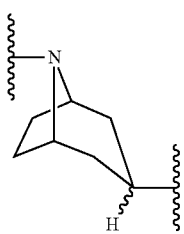
M₃

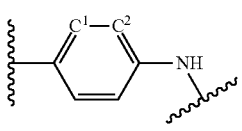
M₄

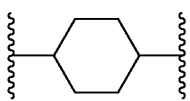
M₅ in which m is an integer equal to 0 or 1 and —C¹— and —C²—, identical or different, represent a nitrogen atom or —CR⁵— wherein R⁵ represents hydrogen, halogen or a group selected from alkoxy, alkyl, alkenyl, alkynyl, cycloalkyl, aryl, arylalkyl, heteroaryl and heteroalkyl groups, or a substituted group selected from alkoxy, alkyl, alkenyl, cycloalkyl, aryl, arylalkyl, heteroaryl or heteroalkyl groups, said substituent being one or more groups independently selected from halogen, trifluoromethyl, difluoromethyl, azido, alkyl, alkoxy, cyano and nitro, and when the two adjacent cyclic atoms —C¹— and —C² represent —CR⁵, they may also form, together, a fused cycloalkyl, aryl or heteroaryl cyclic structure;

Y represents an oxygen or a sulphur atom;

F' represents one of the following substructures of formula (F-1) to (F-3):

i)

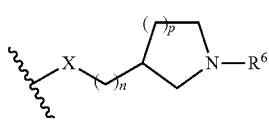
F-1 in which:
n and p can be equal or different and are integers equal to 0, 1, 2 or 3;
X represents an oxygen or a sulphur atom, —NH—, NR⁷ or —CHR⁷— in which R⁷ represents hydrogen, or an alkyl, alkenyl, aryl or heteroaryl group, or a substituted alkyl, alkenyl, aryl or heteroaryl group, said substituent being one or more groups independently selected from halogen, trifluoromethyl, difluoromethyl, azido, alkyl, alkoxy, cyano and nitro;

R⁶ represents an alkyl, alkenyl, alkynyl, cycloalkyl, aryl, arylalkyl, heteroaryl or heteroalkyl group, or a substituted alkyl, alkenyl, alkynyl, cycloalkyl, aryl, arylalkyl, heteroaryl or heteroalkyl group, said substituent being one or more groups independently selected from halogen, trifluoromethyl, difluoromethyl, azido, alkyl, alkoxy, cyano and nitro;

ii)

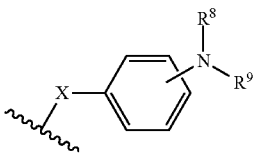
F-2 in which
X has the same definition as the one given for F-1 above;
R⁸ and R⁹, identical or different, independently represent hydrogen or an alkyl, alkenyl, alkynyl, cycloalkyl, aryl, arylalkyl, heteroaryl or heteroalkyl group, or a substituted alkyl, alkenyl, alkynyl, cycloalkyl, aryl, arylalkyl, heteroaryl or heteroalkyl, said substituent being one or more groups independently selected from halogen, trifluoromethyl, difluoromethyl, azido, alkyl, alkoxy, cyano and nitro;

iii)

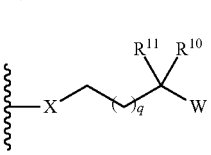
F-3 in which:
X has the same definition as the one given for F-1 above;
q is an integer equal to 0, 1, 2 or 3;
R¹⁰ and R¹¹, identical or different, independently represent hydrogen or an alkyl, alkyloxyalkyl, alkylthioalkyl, alkyloxyaryl, alkylthioaryl, alkenyl, alkynyl, cycloalkyl, aryl, arylalkyl, heteroaryl and heteroalkyl, or a substituted alkyl, alkyloxyalkyl, alkylthioalkyl, alkyloxyaryl, alkylthioaryl, alkenyl, alkynyl, cycloalkyl, aryl, arylalkyl, heteroaryl or heteroalkyl, said substituent being one or more groups independently selected from halogen, trifluoromethyl, difluoromethyl, azido, alkyl, alkoxy, aryloxy, thioalkyl, thiaryl, cyano and nitro;
W represents hydrogen or a radical R¹², OR¹², SR¹² or NR¹²R¹³ wherein R¹² and R¹³, identical or different, independently represent an alkyl, alkenyl, alkynyl, cycloalkyl, aryl, arylalkyl, heteroaryl or heteroalkyl group, or a substituted alkyl, alkenyl, alkynyl, cycloalkyl, aryl, arylalkyl, heteroaryl or heteroalkyl group, said substituent being one or more groups independently selected from halogen, trifluoromethyl, difluoromethyl, azido, alkyl, alkoxy, cyano and nitro; W may also represent a moiety selected in the group consisting of moieties of formula (W₁) to (W₃) below:

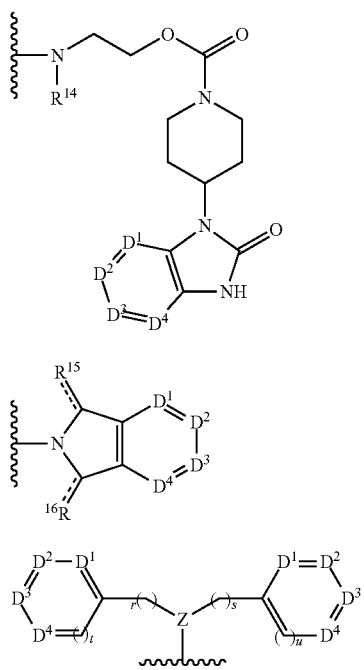

in which:
- $R^{14}$ represents hydrogen, an alkyl, alkenyl, alkynyl, cycloalkyl, aryl, arylalkyl, heteroaryl or heteroalkyl group, or a substituted alkyl, alkenyl, alkynyl, cycloalkyl, aryl, arylalkyl, heteroaryl or heteroalkyl, said substituent being one or more groups independently selected from halogen, trifluoromethyl, difluoromethyl, azido, alkyl, alkoxy, cyano and nitro;
- $R^{15}$ and $R^{16}$, identical or different, represent a hydrogen or oxygen atom,
- Z represents a nitrogen atom or a CH group;
- r and s, identical or different, are integers equal to 0, 1 or 2;
- t and u, identical or different, are integers equal to 0 or 1;
- $D^1$, $D^2$, $D^3$ and $D^4$, identical or different, represent a nitrogen atom or C—$R^{17}$, wherein $R^{17}$ represents hydrogen, halogen or an alkoxy, alkyl, alkenyl, alkynyl, cycloalkyl, aryl, arylalkyl, heteroaryl or heteroalkyl group, or a substituted group selected from alkoxy, alkyl, alkenyl, alkynyl, cycloalkyl, aryl, arylalkyl, heteroaryl or heteroalkyl groups, said substituent being one or more groups independently selected from halogen, trifluoromethyl, difluoromethyl, azido, alkyl, alkoxy, cyano and nitro, and when two adjacent cyclic atoms $D^1$, $D^2$, $D^3$ and $D^4$ represent —$CR^{17}$, said two adjacent cyclic atoms may also form, together, a fused cycloalkyl, aryl or heteroaryl cyclic structure; it being understood that in compounds of formula (I) in which W represents a moiety of formula ($W_3$), when t or u=0, $D^1$, $D^2$, $D^3$ and $D^4$ can also represent O, S or N—$R^{17}$ groups in which $R^{17}$ has the same definition as in —C—$R^{17}$.

2. The compound of claim 1, wherein alkyl groups are chosen among ($C_1$-$C_4$)alkyl groups and wherein alkoxy groups are chosen among linear and branched ($C_1$-$C_4$)alkoxy groups.

3. The compound of claim 2, wherein ($C_1$-$C_4$)alkyl groups are chosen among methyl, ethyl, n-propyl, isopropyl, n-butyl, tert-butyl and isobutyl radicals; whereas ($C_1$-$C_4$)alkoxy groups are chosen among methoxy, ethoxy, n-propyloxy, isopropyloxy, tert-butyloxy and isobutyloxy radicals.

4. The compound of claim 1, wherein halogen atoms are chosen among chlorine, fluorine, bromine and iodine.

5. The compound of claim 1, wherein heteroaryl groups represent pyridine, pyrrole, thiophene, imidazole, pyrazole, oxazole, isoxazole, thiazole, benzene, pyridine, pyrazine, pyrimidine, pyridazine, benzylcyclobutene, pentalene, benzofurane, isobenzofurane, indole, isoindole, benzothiophene, benzo[c]thiophene, benzimidazole, indazole, benzoxazole, benzisoxazole, benzothiazole, naphthalene, quinoline, isoquinoline, quinoxaline, quinazoline, cinnoline, purine, anthracene or acridine.

6. The compound of claim 1, wherein compounds of formula (I) are chosen among compounds in which $A_1$=$A^2$=$A^3$=$A^4$=a carbon atom or $A^1$=$A^2$=$A^3$=a carbon atom and $A^4$=a nitrogen atom.

7. The compound of claim 1, wherein compounds of formula (I) are chosen among compounds in which $C^1$=$C^2$=a carbon atom or $C^1$=a carbon atom and $C^2$=a nitrogen atom or $C^1$ and $C^2$ form together a fused arylic or heteroarylic moiety.

8. The compound of claim 1, wherein compounds of formula (I) are chosen among compounds in which B represents —$NR^3$— with $R^3$=a hydrogen atom.

9. The compound of claim 1, wherein said at least one compound of formula (I) is selected from the group consisting of:
- (S)-2-(dibenzylamino)propyl 4-(1,2-dihydro-2-oxobenzo[d]imidazol-3-yl)piperidine-1-carboxylate;
- (S)-2-(dibenzylamino)-3-phenylpropyl 4-(1,2-dihydro-2-oxobenzo[d]imidazol-3-yl)piperidine-1-carboxylate;
- 2-(dibenzylamino)ethyl 4-(1,2-dihydro-2-oxobenzo[d]imidazol-3-yl)piperidine-1-carboxylate;
- 3-(dibenzylamino)propyl 4-(1,2-dihydro-2-oxobenzo[d]imidazol-3-yl)piperidine-1-carboxylate;
- 2-(N-benzyl-N-methylamino)ethyl 4-(1,2-dihydro-2-oxobenzo[d]imidazol-3-yl)piperidine-1-carboxylate;
- (S)-2-(dibenzylamino)propyl 4-(1,2-dihydro-2-thioxobenzo[d]imidazol-3-yl)piperidine-1-carboxylate;
- (S)-2-(dibenzylamino)propyl 4-(1H-benzo[d]imidazol-1-yl)piperidine-1-carboxylate;
- O-2-(dibenzylamino)ethyl 4-(1,2-dihydro-2-oxobenzo[d]imidazol-3-yl)piperidine-1-carbothioate;
- O-2-(benzyloxy)ethyl 4-(1,2-dihydro-2-oxobenzo[d]imidazol-3-yl)piperidine-1-carbothioate;
- (S)-2-(dibenzylamino)propyl 4-(2,3-dihydro-2-oxoimidazo[4,5-b]pyridin-1-yl)piperidine-1-carboxylate;
- (S)-2-(dibenzylamino)propyl 4-(1,2-dihydro-2-oxo-1-(benzoyl)benzo[d]imidazol-3-yl)piperidine-1-carboxylate;
- (S)-2-(dibenzylamino)propyl 4-(1,2-dihydro-2-oxobenzo[d]imidazol-3-yl)azepane-1-carboxylate;
- 1-benzhydrylazetidin-3-yl 4-(1,2-dihydro-2-oxobenzo[d]imidazol-3-yl)piperidine-1-carboxylate;
- 3-(dimethylamino)phenyl 4-(1,2-dihydro-2-oxobenzo[d]imidazol-3-yl)piperidine-1-carboxylate;
- 2-(1,3-dioxoisoindolin-2-yl)ethyl 4-(1,2-dihydro-2-oxobenzo[d]imidazol-3-yl)piperidine-1-carboxylate;
- 2-(ethyl(phenyl)amino)ethyl 4-(2-oxo-2,3-dihydro-1H-benzo[d]imidazol-1-yl)piperidine-1-carboxylate;
- 3,3-diphenylpropyl 4-(1,2-dihydro-2-oxobenzo[d]imidazol-3-yl)piperidine-1-carboxylate;
- (S)-2-(dibenzylamino)propyl 3-(1,2-dihydro-2-oxobenzo[d]imidazol-3-yl)pyrrolidine-1-carboxylate;

(S)-2-(dibenzylamino)propyl 3-(2-oxo-2,3-dihydro-1H-benzo[d]imidazol-1-yl)-8-azabicyclo[3.2.1]octane-8-carboxylate;
1-[1-(4-dibenzylamino-butyryl)-piperidin-4-yl]-1,3-dihydro-benzoimidazol-2-one;
(S)-2-(dibenzylamino)-3-phenylpropyl 4-(1,2-dihydro-1-methyl-2-oxobenzo[d]imidazol-3-yl)piperidine-1-carboxylate;
N—((S)-2-(dibenzylamino)propyl)-4-(1,2-dihydro-2-oxobenzo[d]imidazol-3-yl)piperidine-1-carbothioamide;
N—((S)-2-(dibenzylamino)propyl)-4-(1,2-dihydro-2-oxobenzo[d]imidazol-3-yl)cyclohexanecarboxamide;
2,2-diphenylethyl 4-(1,2-dihydro-2-oxobenzo[d]imidazol-3-yl)piperidine-1-carboxylate;
2-(N-(4-nitrobenzyl)-N-benzylamino)ethyl 4-(1,2-dihydro-2-oxobenzo[d]imidazol-3-yl)piperidine-1-carboxylate;
2-(dibenzylamino)propyl 4-(1,2-dihydro-2-oxobenzo[d]imidazol-3-yl)phenylcarbamate;
(S)-2-(dibenzylamino)-3-methylbutyl 4-(1,2-dihydro-2-oxobenzo[d]imidazol-3-yl)piperidine-1-carboxylate;
(S)-2-(dibenzylamino)-4-methylpentyl 4-(2-oxo-2,3-dihydro-1H-benzo[d]imidazol-1-yl)piperidine-1-carboxylate;
2-(dibenzylamino)-3,3-dimethylbutyl 4-(1,2-dihydro-2-oxobenzo[d]imidazol-3-yl)piperidine-1-carboxylate;
3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
(S)-2-(dibenzylamino)-2-phenylethyl 4-(1,2-dihydro-2-oxobenzo[d]imidazol-3-yl)piperidine-1-carboxylate;
2-(N-benzyl-N-phenylamino)ethyl 4-(1,2-dihydro-2-oxobenzo[d]imidazol-3-yl)piperidine-1-carboxylate;
(S)-2-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-nitrobenzyl)amino)propyl 4-(2-oxo-2,3-dihydro-1H-benzo[d]imidazol-1-yl)piperidine-1-carboxylate
3-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-methoxybenzyl)amino)propyl 4-(2-oxo-2,3-dihydro-1H-benzo[d]imidazol-1-yl)piperidine-1-carboxylate;
2-(benzyl(4-bromobenzyl)amino)ethyl 4-(2-oxo-2,3-dihydro-1H-benzo[d]imidazol-1-yl)piperidine-1-carboxylate;
(S)-2-(benzyl(4-bromobenzyl)amino)propyl 4-(2-oxo-2,3-dihydro-1H-benzo[d]imidazol-1-yl)piperidine-1-carboxylate;
3-(benzyl(4-methoxybenzyl)amino)propyl 4-(2-oxo-2,3-dihydro-1H-benzo[d]imidazol-1-yl)piperidine-1-carboxylate;
(R)-2-(dibenzylamino)-3-phenylpropyl 4-(1,2-dihydro-2-oxobenzo[d]imidazol-3-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;
2-(benzyl(4-methoxybenzyl)amino)ethyl 4-(2-oxo-2,3-dihydro-1H-benzo[d]imidazol-1-yl)piperidine-1-carboxylate;
2-(benzyl(3-methoxybenzyl)amino)ethyl 4-(2-oxo-2,3-dihydro-1H-benzo[d]imidazol-1-yl)piperidine-1-carboxylate;
2-(benzyl(3-phenoxybenzyl)amino)ethyl 4-(2-oxo-2,3-dihydro-1H-benzo[d]imidazol-1-yl)piperidine-1-carboxylate;
2-(benzyl(3-chlorobenzyl)amino)ethyl 4-(2-oxo-2,3-dihydro-1H-benzo[d]imidazol-1-yl)piperidine-1-carboxylate;
(S)-2-(benzyl(4-fluorobenzyl)amino)propyl 4-(2-oxo-2,3-dihydro-1H-benzo[d]imidazol-1-yl)piperidine-1-carboxylate;
(S)-2-(benzyl(3-phenylpropyl)amino)propyl 4-(2-oxo-2,3-dihydro-1H-benzo[d]imidazol-1-yl)piperidine-1-carboxylate;
(S)-2-(benzyl(quinolin-4-ylmethyl)amino)propyl 4-(2-oxo-2,3-dihydro-1H-benzo[d]imidazol-1-yl)piperidine-1-carboxylate;
(S)-2-(benzyl(3-methoxybenzyl)amino)propyl 4-(2-oxo-2,3-dihydro-1H-benzo[d]imidazol-1-yl)piperidine-1-carboxylate;
(S)-2-(benzyl(3-phenoxybenzyl)amino)propyl 4-(2-oxo-2,3-dihydro-1H-benzo[d]imidazol-1-yl)piperidine-1-carboxylate;
(S)-2-(benzyl(3-chlorobenzyl)amino)propyl 4-(2-oxo-2,3-dihydro-1H-benzo[d]imidazol-1-yl)piperidine-1-carboxylate;
2-(benzyl(quinolin-4-ylmethyl)amino)ethyl 4-(2-oxo-2,3-dihydro-1H-benzo[d]imidazol-1-yl)piperidine-1-carboxylate;
3-(benzyl(pyridin-3-ylmethyl)amino)propyl 4-(2-oxo-2,3-dihydro-1H-benzo[d]imidazol-1-yl)piperidine-1-carboxylate;
3-(benzyl(pyridin-2-ylmethyl)amino)propyl 4-(2-oxo-2,3-dihydro-1H-benzo[d]imidazol-1-yl)piperidine-1-carboxylate;
(S)-2-(benzyl(3-(benzyloxy)benzyl)amino)propyl 4-(2-oxo-2,3-dihydro-1H-benzo[d]imidazol-1-yl)piperidine-1-carboxylate;
(S)-2-(benzyl(phenanthren-9-ylmethyl)amino)propyl 4-(2-oxo-2,3-dihydro-1H-benzo[d]imidazol-1-yl)piperidine-1-carboxylate;
(S)-2-(benzyl(naphthalen-1-ylmethyl)amino)propyl 4-(2-oxo-2,3-dihydro-1H-benzo[d]imidazol-1-yl)piperidine-1-carboxylate;
(S)-2-(benzyl(thiophen-2-ylmethyl)amino)propyl 4-(2-oxo-2,3-dihydro-1H-benzo[d]imidazol-1-yl)piperidine-1-carboxylate;
(S)-2-(benzyl(pyridin-2-ylmethyl)amino)propyl 4-(2-oxo-2,3-dihydro-1H-benzo[d]imidazol-1-yl)piperidine-1-carboxylate;
2-(benzyl(tert-butoxycarbonyl)amino)ethyl 4-(2-oxo-2,3-dihydro-1H-benzo[d]imidazol-1-yl)piperidine-1-carboxylate;
3-(benzyl(thiophen-2-ylmethyl)amino)propyl 4-(2-oxo-2,3-dihydro-1H-benzo[d]imidazol-1-yl)piperidine-1-carboxylate;
3-(benzyl(4-fluorobenzyl)amino)propyl 4-(2-oxo-2,3-dihydro-1H-benzo[d]imidazol-1-yl)piperidine-1-carboxylate;
3-(benzyl(3-methoxybenzyl)amino)propyl 4-(2-oxo-2,3-dihydro-1H-benzo[d]imidazol-1-yl)piperidine-1-carboxylate;

3-(benzyl(3-chlorobenzyl)amino)propyl 4-(2-oxo-2,3-dihydro-1H-benzo[d]imidazol-1-yl)piperidine-1-carboxylate;
3-(benzyl(naphthalen-1-ylmethyl)amino)propyl 4-(2-oxo-2,3-dihydro-1H-benzo[d]imidazol-1-yl)piperidine-1-carboxylate;
3-(benzyl(quinolin-4-ylmethyl)amino)propyl 4-(2-oxo-2,3-dihydro-1H-benzo[d]imidazol-1-yl)piperidine-1-carboxylate;
3-(benzyl((1-methyl-1H-indol-2-yl)methyl)amino)propyl 4-(2-oxo-2,3-dihydro-1H-benzo[d]imidazol-1-yl)piperidine-1-carboxylate;
3-(benzyl(3-phenoxybenzyl)amino)propyl 4-(2-oxo-2,3-dihydro-1H-benzo[d]imidazol-1-yl)piperidine-1-carboxylate;
2-(benzyl(4-chlorobenzyl)amino)ethyl 4-(2-oxo-2,3-dihydro-1H-benzo[d]imidazol-1-yl)piperidine-1-carboxylate;
2-(benzyl(2-methoxybenzyl)amino)ethyl 4-(2-oxo-2,3-dihydro-1H-benzo[d]imidazol-1-yl)piperidine-1-carboxylate;
2-(benzyl(2-(benzyloxy)benzyl)amino)ethyl 4-(2-oxo-2,3-dihydro-1H-benzo[d]imidazol-1-yl)piperidine-1-carboxylate;
2-(benzyl(4-(benzyloxy)benzyl)amino)ethyl 4-(2-oxo-2,3-dihydro-1H-benzo[d]imidazol-1-yl)piperidine-1-carboxylate;
2-(benzyl(2,6-difluorobenzyl)amino)ethyl 4-(2-oxo-2,3-dihydro-1H-benzo[d]imidazol-1-yl)piperidine-1-carboxylate;
(S)-2-(benzyl(furan-2-ylmethyl)amino)propyl 4-(2-oxo-2,3-dihydro-1H-benzo[d]imidazol-1-yl)piperidine-1-carboxylate;
3-(benzyl(furan-3-ylmethyl)amino)propyl 4-(2-oxo-2,3-dihydro-1H-benzo[d]imidazol-1-yl)piperidine-1-carboxylate;
2-(benzyl(3-(benzyloxy)benzyl)amino)ethyl 4-(2-oxo-2,3-dihydro-1H-benzo[d]imidazol-1-yl)piperidine-1-carboxylate;
(E)-2-(benzyl(cinnamyl)amino)ethyl 4-(2-oxo-2,3-dihydro-1H-benzo[d]imidazol-1-yl)piperidine-1-carboxylate;
3-(benzyl(4-chlorobenzyl)amino)propyl 4-(2-oxo-2,3-dihydro-1H-benzo[d]imidazol-1-yl)piperidine-1-carboxylate;
3-(benzyl(3-(benzyloxy)benzyl)amino)propyl 4-(2-oxo-2,3-dihydro-1H-benzo[d]imidazol-1-yl)piperidine-1-carboxylate;
(S)-2-(benzyl(tert-butoxycarbonyl)amino)-4-methylpentyl 4-(2-oxo-2,3-dihydro-1H-benzo[d]imidazol-1-yl)piperidine-1-carboxylate;
(S)-2-(benzyl(tert-butoxycarbonyl)amino)-3-phenylpropyl 4-(2-oxo-2,3-dihydro-1H-benzo[d]imidazol-1-yl)piperidine-1-carboxylate;
(S)-2-(benzylamino)-4-methylpentyl 4-(2-oxo-2,3-dihydro-1H-benzo[d]imidazol-1-yl)piperidine-1-carboxylate;
2-(benzylamino)-3-phenylpropyl 4-(2-oxo-2,3-dihydro-1H-benzo[d]imidazol-1-yl)piperidine-1-carboxylate;
2-(benzyl(3-(benzyloxy)propyl)amino)propyl 4-(2-oxo-2,3-dihydro-1H-benzo[d]imidazol-1-yl)piperidine-1-carboxylate;
3-(benzyl(3-phenylpropyl)amino)propyl 4-(2-oxo-2,3-dihydro-1H-benzo[d]imidazol-1-yl)piperidine-1-carboxylate and acid addition salts thereof.

10. A compound selected from the group consisting of:
(S)-2-(dibenzylamino)propyl 4-(1H-benzo[d]imidazol-1-yl)piperidine-1-carboxylate;
2-(ethyl(phenyl)amino)ethyl 4-(2-oxo-2,3-dihydro-1H-benzo[d]imidazol-1-yl)piperidine-1-carboxylate;
(S)-2-(dibenzylamino)propyl 4-(2,3-dihydro-2-oxoimidazo[4,5-b]pyridin-1-yl)piperidine-1-carboxylate;
1-benzhydrylazetidin-3-yl 4-(1,2-dihydro-2-oxobenzo[d]imidazol-3-yl)piperidine-1-carboxylate;
(S)-2-(dibenzylamino)-3-phenylpropyl 4-(1,2-dihydro-2-oxobenzo[d]imidazol-3-yl)piperidine-1-carboxylate;
2-(dibenzylamino)ethyl 4-(1,2-dihydro-2-oxobenzo[d]imidazol-3-yl)piperidine-1-carboxylate;
O-2-(dibenzylamino)ethyl 4-(1,2-dihydro-2-oxobenzo[d]imidazol-3-yl)piperidine-1-carbothioate;
2-(N-(4-nitrobenzyl)-N-benzylamino)ethyl 4-(1,2-dihydro-2-oxobenzo[d]imidazol-3-yl)piperidine-1-carboxylate;
1-[1-(4-dibenzylamino-butyryl)-piperidin-4-yl]-1,3-dihydro-benzoimidazol-2-one;
(S)-2-(dibenzylamino)propyl 4-(1,2-dihydro-2-oxobenzo[d]imidazol-3-yl)piperidine-1-carboxylate;
3-(dibenzylamino)propyl 4-(1,2-dihydro-2-oxobenzo[d]imidazol-3-yl)piperidine-1-carboxylate;
2-(1,3-dioxoisoindolin-2-yl)ethyl 4-(1,2-dihydro-2-oxobenzo[d]imidazol-3-yl)piperidine-1-carboxylate;
3,3-diphenylpropyl 4-(1,2-dihydro-2-oxobenzo[d]imidazol-3-yl)piperidine-1-carboxylate;
2-(dibenzylamino)propyl 4-(1,2-dihydro-2-oxobenzo[d]imidazol-3-yl)phenylcarbamate;
(S)-2-(dibenzylamino)propyl 4-(1,2-dihydro-2-oxo-1-(benzoyl)benzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
N—((S)-2-(dibenzylamino)propyl)-4-(1,2-dihydro-2-oxobenzo[d]imidazol-3-yl)piperidine-1-carbothioamide;
2,2-diphenylethyl 4-(1,2-dihydro-2-oxobenzo[d]imidazol-3-yl)piperidine-1-carboxylate;
(S)-2-(dibenzylamino)-3-phenylpropyl 4-(1,2-dihydro-1-methyl-2-oxobenzo[d]imidazol-3-yl)piperidine-1-carboxylate;
(S)-3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
3-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-methoxybenzyl)amino)propyl 4-(2-oxo-2,3-dihydro-1H-benzo[d]imidazol-1-yl)piperidine-1-carboxylate;
2-(benzyl(4-bromobenzyl)amino)ethyl 4-(2-oxo-2,3-dihydro-1H-benzo[d]imidazol-1-yl)piperidine-1-carboxylate;
3-(benzyl(4-methoxybenzyl)amino)propyl 4-(2-oxo-2,3-dihydro-1H-benzo[d]imidazol-1-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;

2-(benzyl(4-methoxybenzyl)amino)ethyl 4-(2-oxo-2,3-dihydro-1H-benzo[d]imidazol-1-yl)piperidine-1-carboxylate;

2-(benzyl(3-methoxybenzyl)amino)ethyl 4-(2-oxo-2,3-dihydro-1H-benzo[d]imidazol-1-yl)piperidine-1-carboxylate;

(S)-2-(benzyl(3-phenylpropyl)amino)propyl 4-(2-oxo-2,3-dihydro-1H-benzo[d]imidazol-1-yl)piperidine-1-carboxylate;

3-(benzyl(pyridin-3-ylmethyl)amino)propyl 4-(2-oxo-2,3-dihydro-1H-benzo[d]imidazol-1-yl)piperidine-1-carboxylate;

3-(benzyl(pyridin-2-ylmethyl)amino)propyl 4-(2-oxo-2,3-dihydro-1H-benzo[d]imidazol-1-yl)piperidine-1-carboxylate;

(S)-2-(benzyl(3-(benzyloxy)benzyl)amino)propyl 4-(2-oxo-2,3-dihydro-1H-benzo[d]imidazol-1-yl)piperidine-1-carboxylate;

(S)-2-(benzyl(pyridin-2-ylmethyl)amino)propyl 4-(2-oxo-2,3-dihydro-1H-benzo[d]imidazol-1-yl)piperidine-1-carboxylate;

2-(benzyl(tert-butoxycarbonyl)amino)ethyl 4-(2-oxo-2,3-dihydro-1H-benzo[d]imidazol-1-yl)piperidine-1-carboxylate;

3-(benzyl(thiophen-2-ylmethyl)amino)propyl 4-(2-oxo-2,3-dihydro-1H-benzo[d]imidazol-1-yl)piperidine-1-carboxylate;

3-(benzyl(4-fluorobenzyl)amino)propyl 4-(2-oxo-2,3-dihydro-1H-benzo[d]imidazol-1-yl)piperidine-1-carboxylate;

3-(benzyl(3-phenylpropyl)amino)propyl 4-(2-oxo-2,3-dihydro-1H-benzo[d]imidazol-1-yl)piperidine-1-carboxylate;

3-(benzyl(3-methoxybenzyl)amino)propyl 4-(2-oxo-2,3-dihydro-1H-benzo[d]imidazol-1-yl)piperidine-1-carboxylate;

3-(benzyl(3-chlorobenzyl)amino)propyl 4-(2-oxo-2,3-dihydro-1H-benzo[d]imidazol-1-yl)piperidine-1-carboxylate;

3-(benzyl(naphthalen-1-ylmethyl)amino)propyl 4-(2-oxo-2,3-dihydro-1H-benzo[d]imidazol-1-yl)piperidine-1-carboxylate;

2-(benzyl(2-methoxybenzyl)amino)ethyl 4-(2-oxo-2,3-dihydro-1H-benzo[d]imidazol-1-yl)piperidine-1-carboxylate;

2-(benzyl(2,6-difluorobenzyl)amino)ethyl 4-(2-oxo-2,3-dihydro-1H-benzo[d]imidazol-1-yl)piperidine-1-carboxylate;

3-(benzyl(furan-3-ylmethyl)amino)propyl 4-(2-oxo-2,3-dihydro-1H-benzo[d]imidazol-1-yl)piperidine-1-carboxylate;

(E)-2-(benzyl(cinnamyl)amino)ethyl 4-(2-oxo-2,3-dihydro-1H-benzo[d]imidazol-1-yl)piperidine-1-carboxylate;

3-(benzyl(4-chlorobenzyl)amino)propyl 4-(2-oxo-2,3-dihydro-1H-benzo[d]imidazol-1-yl)piperidine-1-carboxylate;

2-(benzyl(3-(benzyloxy)propyl)amino)propyl 4-(2-oxo-2,3-dihydro-1H-benzo[d]imidazol-1-yl)piperidine-1-carboxylate and acid addition salts thereof as herbicide.

11. A compound selected from the group consisting of:

2-(dibenzylamino)ethyl 4-(1,2-dihydro-2-oxobenzo[d]imidazol-3-yl)piperidine-1-carboxylate;

O-2-(benzyloxy)ethyl 4-(1,2-dihydro-2-oxobenzo[d]imidazol-3-yl)piperidine-1-carbothioate;

1-benzhydrylazetidin-3-yl 4-(1,2-dihydro-2-oxobenzo[d]imidazol-3-yl)piperidine-1-carboxylate;

(S)-2-(dibenzylamino)propyl 3-(1,2-dihydro-2-oxobenzo[d]imidazol-3-yl)pyrrolidine-1-carboxylate;

(S)-2-(dibenzylamino)-3-phenylpropyl 4-(1,2-dihydro-1-methyl-2-oxobenzo[d]imidazol-3-yl)piperidine-1-carboxylate;

3-(dibenzylamino)butyl 4-(1,2-dihydro-2-oxobenzo[d]imidazol-3-yl)piperidine-1-carboxylate;

2-(dibenzylamino)-2-methylpropyl 4-(1,2-dihydro-2-oxobenzo[d]imidazol-3-yl)piperidine-1-carboxylate;

(S)-2-(benzyl(4-bromobenzyl)amino)propyl 4-(2-oxo-2,3-dihydro-1H-benzo[d]imidazol-1-yl)piperidine-1-carboxylate;

2-(benzyl(pyridin-4-ylmethyl)amino)ethyl 4-(2-oxo-2,3-dihydro-1H-benzo[d]imidazol-1-yl)piperidine-1-carboxylate;

2-(benzyl(4-fluorobenzyl)amino)ethyl 4-(2-oxo-2,3-dihydro-1H-benzo[d]imidazol-1-yl)piperidine-1-carboxylate;

2-(benzyl(3-phenylpropyl)amino)ethyl 4-(2-oxo-2,3-dihydro-1H-benzo[d]imidazol-1-yl)piperidine-1-carboxylate;

2-(benzyl(4-methoxybenzyl)amino)ethyl 4-(2-oxo-2,3-dihydro-1H-benzo[d]imidazol-1-yl)piperidine-1-carboxylate;

2-(benzyl(3-methoxybenzyl)amino)ethyl 4-(2-oxo-2,3-dihydro-1H-benzo[d]imidazol-1-yl)piperidine-1-carboxylate;

3-(benzyl(pyridin-3-ylmethyl)amino)propyl 4-(2-oxo-2,3-dihydro-1H-benzo[d]imidazol-1-yl)piperidine-1-carboxylate;

3-(benzyl(pyridin-2-ylmethyl)amino)propyl 4-(2-oxo-2,3-dihydro-1H-benzo[d]imidazol-1-yl)piperidine-1-carboxylate;

2-(benzyl(tert-butoxycarbonyl)amino)ethyl 4-(2-oxo-2,3-dihydro-1H-benzo[d]imidazol-1-yl)piperidine-1-carboxylate and acid addition salts thereof as algaecide.

12. The compound of claim 1, wherein acid addition salts are selected from the group consisting of hydrochloride, hydrobromide, sulphate, bisulphate, phosphate, hydrogenophosphate, acetate, benzoate, succinate, fumarate, maleate, lactate, citrate, tartrate, gluconate, methanesulphonate, benzene-sulphonate and paratoluene-sulphonate.

13. A method for inhibiting growth of a plant or an algae comprising contacting a cell of a plant or an algae with a composition comprising at least one compound of claim 1.

14. The method of claim 13, wherein the composition is a herbicide composition and the at least one compound of formula (I) is selected from the group consisting of:

(S)-2-(dibenzylamino)propyl 4-(1H-benzo[d]imidazol-1-yl)piperidine-1-carboxylate;

2-(ethyl(phenyl)amino)ethyl 4-(2-oxo-2,3-dihydro-1H-benzo[d]imidazol-1-yl)piperidine-1-carboxylate;

(S)-2-(dibenzylamino)propyl 4-(2,3-dihydro-2-oxoimidazo[4,5-b]pyridin-1-yl)piperidine-1-carboxylate;

1-benzhydrylazetidin-3-yl 4-(1,2-dihydro-2-oxobenzo[d]imidazol-3-yl)piperidine-1-carboxylate;

(S)-2-(dibenzylamino)-3-phenylpropyl 4-(1,2-dihydro-2-oxobenzo[d]imidazol-3-yl)piperidine-1-carboxylate;

2-(dibenzylamino)ethyl 4-(1,2-dihydro-2-oxobenzo[d]imidazol-3-yl)piperidine-1-carboxylate;

O-2-(dibenzylamino)ethyl 4-(1,2-dihydro-2-oxobenzo[d]imidazol-3-yl)piperidine-1-carbothioate;

2-(N-(4-nitrobenzyl)-N-benzylamino)ethyl 4-(1,2-dihydro-2-oxobenzo[d]imidazol-3-yl)piperidine-1-carboxylate;

1-[1-(4-dibenzylamino-butyryl)-piperidin-4-yl]-1,3-dihydro-benzoimidazol-2-one;

(S)-2-(dibenzylamino)propyl 4-(1,2-dihydro-2-oxobenzo[d]imidazol-3-yl)piperidine-1-carboxylate;
3-(dibenzylamino)propyl 4-(1,2-dihydro-2-oxobenzo[d]imidazol-3-yl)piperidine-1-carboxylate;
2-(1,3-dioxoisoindolin-2-yl)ethyl 4-(1,2-dihydro-2-oxobenzo[d]imidazol-3-yl)piperidine-1-carboxylate;
3,3-diphenylpropyl 4-(1,2-dihydro-2-oxobenzo[d]imidazol-3-yl)piperidine-1-carboxylate;
2-(dibenzylamino)propyl 4-(1,2-dihydro-2-oxobenzo[d]imidazol-3-yl)phenylcarbamate;
(S)-2-(dibenzylamino)propyl 4-(1,2-dihydro-2-oxo-1-(benzoyl)benzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
N—((S)-2-(dibenzylamino)propyl)-4-(1,2-dihydro-2-oxobenzo[d]imidazol-3-yl)piperidine-1-carbothioamide;
2,2-diphenylethyl 4-(1,2-dihydro-2-oxobenzo[d]imidazol-3-yl)piperidine-1-carboxylate;
(S)-2-(dibenzylamino)-3-phenylpropyl 4-(1,2-dihydro-1-methyl-2-oxobenzo[d]imidazol-3-yl)piperidine-1-carboxylate;
(S)-3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
3-(benzyl(4-nitrobenzyl)amino)propyl 4-(2-oxo-2,3-dihydro-1H-benzo[d]imidazol-1-yl)piperidine-1-carboxylate;
(S)-2-(benzyl(4-methoxybenzyl)amino)propyl 4-(2-oxo-2,3-dihydro-1H-benzo[d]imidazol-1-yl)piperidine-1-carboxylate;
2-(benzyl(4-bromobenzyl)amino)ethyl 4-(2-oxo-2,3-dihydro-1H-benzo[d]imidazol-1-yl)piperidine-1-carboxylate;
3-(benzyl(4-methoxybenzyl)amino)propyl 4-(2-oxo-2,3-dihydro-1H-benzo[d]imidazol-1-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;
2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;
2-(benzyl(4-methoxybenzyl)amino)ethyl 4-(2-oxo-2,3-dihydro-1H-benzo[d]imidazol-1-yl)piperidine-1-carboxylate;
2-(benzyl(3-methoxybenzyl)amino)ethyl 4-(2-oxo-2,3-dihydro-1H-benzo[d]imidazol-1-yl)piperidine-1-carboxylate;
(S)-2-(benzyl(3-phenylpropyl)amino)propyl 4-(2-oxo-2,3-dihydro-1H-benzo[d]imidazol-1-yl)piperidine-1-carboxylate;
3-(benzyl(pyridin-3-ylmethyl)amino)propyl 4-(2-oxo-2,3-dihydro-1H-benzo[d]imidazol-1-yl)piperidine-1-carboxylate;
3-(benzyl(pyridin-2-ylmethyl)amino)propyl 4-(2-oxo-2,3-dihydro-1H-benzo[d]imidazol-1-yl)piperidine-1-carboxylate;
(S)-2-(benzyl(3-(benzyloxy)benzyl)amino)propyl 4-(2-oxo-2,3-dihydro-1H-benzo[d]imidazol-1-yl)piperidine-1-carboxylate;
(S)-2-(benzyl(pyridin-2-ylmethyl)amino)propyl 4-(2-oxo-2,3-dihydro-1H-benzo[d]imidazol-1-yl)piperidine-1-carboxylate;
2-(benzyl(tert-butoxycarbonyl)amino)ethyl 4-(2-oxo-2,3-dihydro-1H-benzo[d]imidazol-1-yl)piperidine-1-carboxylate;
3-(benzyl(thiophen-2-ylmethyl)amino)propyl 4-(2-oxo-2,3-dihydro-1H-benzo[d]imidazol-1-yl)piperidine-1-carboxylate;
3-(benzyl(4-fluorobenzyl)amino)propyl 4-(2-oxo-2,3-dihydro-1H-benzo[d]imidazol-1-yl)piperidine-1-carboxylate;
3-(benzyl(3-phenylpropyl)amino)propyl 4-(2-oxo-2,3-dihydro-1H-benzo[d]imidazol-1-yl)piperidine-1-carboxylate;
3-(benzyl(3-methoxybenzyl)amino)propyl 4-(2-oxo-2,3-dihydro-1H-benzo[d]imidazol-1-yl)piperidine-1-carboxylate;
3-(benzyl(3-chlorobenzyl)amino)propyl 4-(2-oxo-2,3-dihydro-1H-benzo[d]imidazol-1-yl)piperidine-1-carboxylate;
3-(benzyl(naphthalen-1-ylmethyl)amino)propyl 4-(2-oxo-2,3-dihydro-1H-benzo[d]imidazol-1-yl)piperidine-1-carboxylate;
2-(benzyl(2-methoxybenzyl)amino)ethyl 4-(2-oxo-2,3-dihydro-1H-benzo[d]imidazol-1-yl)piperidine-1-carboxylate;
2-(benzyl(2,6-difluorobenzyl)amino)ethyl 4-(2-oxo-2,3-dihydro-1H-benzo[d]imidazol-1-yl)piperidine-1-carboxylate;
3-(benzyl(furan-3-ylmethyl)amino)propyl 4-(2-oxo-2,3-dihydro-1H-benzo[d]imidazol-1-yl)piperidine-1-carboxylate;
(E)-2-(benzyl(cinnamyl)amino)ethyl 4-(2-oxo-2,3-dihydro-1H-benzo[d]imidazol-1-yl)piperidine-1-carboxylate;
3-(benzyl(4-chlorobenzyl)amino)propyl 4-(2-oxo-2,3-dihydro-1H-benzo[d]imidazol-1-yl)piperidine-1-carboxylate;
2-(benzyl(3-(benzyloxy)propyl)amino)propyl 4-(2-oxo-2,3-dihydro-1H-benzo[d]imidazol-1-yl)piperidine-1-carboxylate and acid addition salts thereof.

15. The method of claim 13, wherein the composition is an algaecide composition and the at least one compound of formula (I) is selected from the group consisting of:
2-(dibenzylamino)ethyl 4-(1,2-dihydro-2-oxobenzo[d]imidazol-3-yl)piperidine-1-carboxylate;
O-2-(benzyloxy)ethyl 4-(1,2-dihydro-2-oxobenzo[d]imidazol-3-yl)piperidine-1-carbothioate;
1-benzhydrylazetidin-3-yl 4-(1,2-dihydro-2-oxobenzo[d]imidazol-3-yl)piperidine-1-carboxylate;
(S)-2-(dibenzylamino)propyl 3-(1,2-dihydro-2-oxobenzo[d]imidazol-3-yl)pyrrolidine-1-carboxylate;
(S)-2-(dibenzylamino)-3-phenylpropyl 4-(1,2-dihydro-1-methyl-2-oxobenzo[d]imidazol-3-yl)piperidine-1-carboxylate;
3-(dibenzylamino)butyl 4-(1,2-dihydro-2-oxobenzo[d]imidazol-3-yl)piperidine-1-carboxylate;
2-(dibenzylamino)-2-methylpropyl 4-(1,2-dihydro-2-oxobenzo[d]imidazol-3-yl)piperidine-1-carboxylate;
(S)-2-(benzyl(4-bromobenzyl)amino)propyl 4-(2-oxo-2,3-dihydro-1H-benzo[d]imidazol-1-yl)piperidine-1-carboxylate;
2-(benzyl(pyridin-4-ylmethyl)amino)ethyl 4-(2-oxo-2,3-dihydro-1H-benzo[d]imidazol-1-yl)piperidine-1-carboxylate;

2-(benzyl(4-fluorobenzyl)amino)ethyl 4-(2-oxo-2,3-dihydro-1H-benzo[d]imidazol-1-yl)piperidine-1-carboxylate;
2-(benzyl(3-phenylpropyl)amino)ethyl 4-(2-oxo-2,3-dihydro-1H-benzo[d]imidazol-1-yl)piperidine-1-carboxylate;
2-(benzyl(4-methoxybenzyl)amino)ethyl 4-(2-oxo-2,3-dihydro-1H-benzo[d]imidazol-1-yl)piperidine-1-carboxylate;
2-(benzyl(3-methoxybenzyl)amino)ethyl 4-(2-oxo-2,3-dihydro-1H-benzo[d]imidazol-1-yl)piperidine-1-carboxylate;
3-(benzyl(pyridin-3-ylmethyl)amino)propyl 4-(2-oxo-2,3-dihydro-1H-benzo[d]imidazol-1-yl)piperidine-1-carboxylate;
3-(benzyl(pyridin-2-ylmethyl)amino)propyl 4-(2-oxo-2,3-dihydro-1H-benzo[d]imidazol-1-yl)piperidine-1-carboxylate;
2-(benzyl(tert-butoxycarbonyl)amino)ethyl 4-(2-oxo-2,3-dihydro-1H-benzo[d]imidazol-1-yl)piperidine-1-carboxylate and acid addition salts thereof.

* * * * *